(12) United States Patent
Matsuoka et al.

(10) Patent No.: US 7,612,070 B2
(45) Date of Patent: Nov. 3, 2009

(54) INDOLE DERIVATIVE HAVING HETEROCYCLE AND MONO- OR DIAZAINDOLE DERIVATIVE

(75) Inventors: Hiroharu Matsuoka, Gotenba (JP); Nobuaki Kato, Gotenba (JP); Tadakatsu Takahashi, Gotenba (JP); Noriaki Maruyama, Gotenba (JP); Takenori Ishizawa, Gotenba (JP); Yukio Suzuki, Gotenba (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 626 days.

(21) Appl. No.: 11/058,597

(22) Filed: Feb. 16, 2005

(65) Prior Publication Data

US 2005/0137202 A1    Jun. 23, 2005

Related U.S. Application Data

(62) Division of application No. 10/674,488, filed on Oct. 1, 2003, now Pat. No. 6,875,770, which is a division of application No. 09/701,188, filed as application No. PCT/JP99/02718 on May 25, 1999, now Pat. No. 6,673,797.

(30) Foreign Application Priority Data

May 26, 1998  (JP) ............................. 1998/143957
Nov. 13, 1998  (JP) ............................. 1998/323553

(51) Int. Cl.
*A61K 31/4985* (2006.01)
*C07D 487/02* (2006.01)
*A61K 31/40* (2006.01)
*C07D 401/04* (2006.01)

(52) U.S. Cl. ...................... 514/249; 544/350; 546/113; 548/469

(58) Field of Classification Search .................. 514/249; 544/350
See application file for complete search history.

(56) References Cited

U.S. PATENT DOCUMENTS

2007/0238735 A1* 10/2007 Garvey et al. ............ 514/252.1

FOREIGN PATENT DOCUMENTS

| EP | 0535925 A1 | 9/1992 |
|----|------------|--------|
| EP | 0846689 A1 | 12/1997 |
| JP | 10-077266 A | 3/1998 |
| WO | WO 96/06840 A1 | 3/1996 |
| WO | WO 97/30030 | 8/1997 |

OTHER PUBLICATIONS

Morissette et al. Advanced Drug Delivery Reviews 2004, 56, 275-300.*
Vippagunta et al. Advanced Drug Delivery Reviews 2001, 48, 3-26.*
Brideau et al. Inflammation Research 1996, 45, 68-74.*

* cited by examiner

*Primary Examiner*—Kortney L. Klinkel
(74) *Attorney, Agent, or Firm*—Browdy and Neimark, PLLC

(57) ABSTRACT

There is provided a compound represented by the general formula (1):

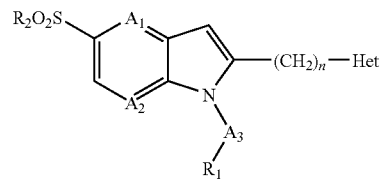

wherein Het represents an optional substituted heterocylic group $A_1$ and $A_2$ each independently represent —CH=, etc.; $A_3$ represents —CH$_2$—, etc.; $R_1$ represents a 4-fluorophenyl group, etc.; $R_2$ represents an alkyl group; n represents 0, 1 or 2, provided that when $A_1$ and $A_2$ both are —CH=, $A_3$ represents —CH$_2$— or —SO$_2$—, which is an indole derivative or a mono- or diazaindole derivative that has COX-2 inhibitory activity and is useful as a pharmaceutical, such as an anti-inflammatory agent, or addition salts thereof with a pharmaceutically acceptable acid or base, or hydrates thereof.

9 Claims, No Drawings

INDOLE DERIVATIVE HAVING HETEROCYCLE AND MONO- OR DIAZAINDOLE DERIVATIVE

CROSS-REFERENCE TO RELATED APPLICATIONS

The present application is a divisional of U.S. application Ser. No. 10/674,488 Oct. 1, 2003, now U.S. Pat. No. 6,875,770, which is a divisional application of Ser. No. 09/701,188 Nov. 27, 2000, now U.S. Pat. No. 6,673,797, which is a 371 of PCT/JP99/02718 May 25, 1999.

TECHNICAL FIELD

The present invention relates to an indole derivative and a mono- or diazaindole derivative that show an anti-inflammatory action and so forth and are useful as pharmaceuticals.

BACKGROUND ART

At present, the majority of medicines widely used as anti-inflammatory agents are non-steroid anti-inflammatory drugs (NSAIDs) that have, as the mechanism of action, an inhibitory action on cyclooxygenase (COX) that is involved in the biosynthesis of prostaglandin E2 (PGE2). However, since PGE2 synthesis activity is present in various tissues in the living body and governs the homeostasis thereof, various side effects are induced when NSAID is administered. For example, PGE2 demonstrates the action of maintaining blood flow in the stomach and kidneys, whereas administration of NSAIDs makes it difficult to maintain local blood flow, thereby causing gastric or renal disorders.

Under such circumstances, the presence of a COX isozyme has been confirmed. In order to distinguish it from the previously identified COX, the conventional type has been named COX-1, while the newly discovered isozyme has been named COX-2. In addition, this COX-2 has been clarified to be induced during inflammation and hardly be expressed at all under normal circumstances. It was also clarified that conventional NSAID are able to non-specifically inhibit both COX-1 and COX-2 enzymes. Therefore, the possibility arose of a compound having COX-2 inhibitory action being useful as a novel anti-inflammatory agent.

There are currently several compounds that are known to selectively inhibit only COX-2 without inhibiting COX-1 (Inflammation and Immunology, 3(1), 29-36, 1995; Bioorganic & Med. Chem. Lett. 5(8), 867-872, 1995, etc.). However, the actions of these compounds are not satisfactory and since some of them do not have an adequate water solubility or oral absorption, there is a need for a drug that demonstrates more effective COX-2 inhibitory action.

In addition, an indole derivative represented by the following formula:

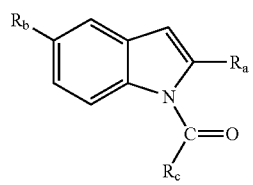

(wherein, Ra represents a hydrogen atom, a straight or branched alkyl group having 1 to 7 carbon atoms, a straight or branched alkenyl group having 2 to 7 carbon atoms, a straight or branched alkynyl group having 2 to 7 carbon atoms, a cycloalkenyl group having 4 to 6 carbon atoms, an aryl group, a heteroaryl group, an alkylcarbonyl group in which the alkyl moiety is a straight or branched alkyl group having 1 to 7 carbon atoms, an alkenylcarbonyl group in which the alkenyl moiety is a straight or branched alkenyl group having 2 to 7 carbon atoms, an alkynylcarbonyl group in which the alkynyl moiety is a straight or branched alkynyl group having 2 to 7 carbon atoms, or —$(CH_2)_m$-Rd, where m represents an integer of 0 to 3 and Rd represents a cycloalkyl group having 3 to 6 carbon atoms which may be substituted with a straight or branched alkyl group having 1 to 3 carbon atoms; Rb represents —$SO_2$—Re, where Re represents a straight or branched alkyl group having 1 to 3 carbon atoms; and Rc represents an aryl group which may have a substituent, a cycloalkyl group having 3 to 6 carbon atoms which may have a substituent, or a monocyclic heterocyclic group which may have a substituent) that selectively inhibits COX-2 is known from Japanese Patent Application Disclosure Hei No. 10-77266 (Japanese Patent Application Hei No. 9-24567).

The object of the present invention is to provide an indole derivative and a mono- or diazaindole derivative that have COX-2 inhibitory activity and are useful as pharmaceuticals, such as anti-inflammatory agents, etc.

As a result of conducting earnest research for the purpose of developing a compound that selectively or non-selectively inhibits COX-2 and has an anti-inflammatory action comparable to or higher than indometacin and other existing NSAIDs, the inventors of the present application found that a compound represented by the general formula (1) has an excellent anti-inflammatory action and/or improved water solubility, making it useful as a pharmaceutical, thereby leading to completion of the present invention on the basis of this finding.

DISCLOSURE OF THE INVENTION

Accordingly, the present invention relates to a compound represented by the general formula (1):

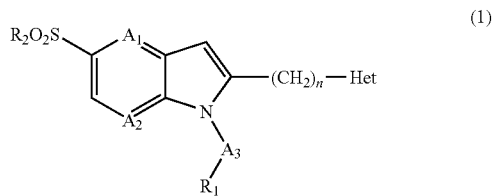

wherein Het represents a heterocyclic group which may be substituted;

$A_1$ and $A_2$ each independently represent —CH= or —N=;

$A_3$ represents —$CH_2$—, —(C=O)— or —$SO_2$—;

$R_1$ represents a group selected from the following formulae:

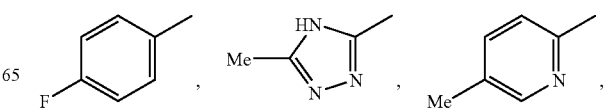

-continued

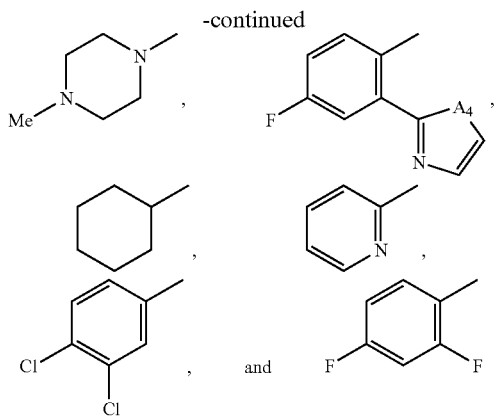

wherein $A_4$ represents —O—, —S— or —NH—;
$R_2$ represents a straight or branched alkyl group having 1 to 3 carbon atoms;
n represents 0, 1 or 2, provided that when both $A_1$ and $A_2$ are —CH═, $A_3$ represents —CH$_2$— or —SO$_2$—, or addition salts thereof with a pharmaceutically acceptable acid or base, or hydrates thereof.

BEST MODE FOR CARRYING OUT THE INVENTION

In the definition of the compound represented by the general formula (1), a straight or branched alkyl group having 1 to 3 carbon atoms includes a methyl group, an ethyl group, an n-propyl group and an i-propyl group.

A heterocyclic group, which may be substituted, represented by Het is a 4- to 10-membered, monocyclic or condensed ring aliphatic or aromatic group containing 1, 2, 3 or 4 hetero atoms, which may be identical or different, such as an oxygen atom, a nitrogen atom and a sulfur atom. The substituent of the heterocyclic group includes, for example, a halogen atom, a straight or branched alkyl group having 1 to 4 carbon atoms (the group may be further substituted with a halogen atom), a straight or branched alkoxyl group having 1 to 4 carbon atoms (the group may be further substituted with a halogen atom), an oxo group, —S(O)$_p$—R$_3$ (in which p is an integer of 0 to 2 and $R_3$ represents a straight or branched alkyl group having 1 to 3 carbon atoms), an amino group, a nitro group, a carboxyl group, —COOR$_4$ (in which $R_4$ represents a straight or branched alkyl group having 1 to 3 carbon atoms), —CONR$_5$R$_6$ (in which $R_5$ and $R_6$ may be the same or different and each represent a hydrogen atom or a straight or branched alkyl group having 1 to 3 carbon atoms), a cyano group and a hydroxyl group. Among them, a fluorine atom, a chlorine atom, a bromine atom, an iodine atom, a methyl group, an ethyl group, an n-propyl group, an i-propyl group, a t-butyl group, a trifluoromethyl group, a methoxy group, an ethoxy group, an oxo group, a methylthio group, a methanesulfonyl group, an ethanesulfonyl group, an amino group, a nitrogroup, a carboxyl group, a methoxycarbonyl group, a methylaminocarbonyl group, a cyano group and a hydroxyl group are preferred and the fluorine atom, the carboxyl group, the methyl group, the methoxycarbonyl group and the methylaminocarbonyl group are particularly preferred. The above heterocyclic group may be further substituted with 1 to 3, preferably 1 heterocyclic group. The heterocyclic group as the substituent in this case includes heterocyclic groups listed below, which may be substituted, represented by Het in the compound of the general formula (1). Among them, tetrazolyl (particularly 5-tetrazolyl) and triazolyl (particularly 1,2,3-triazol-4-yl and 1,2,4-triazol-3-yl) are preferred.

While the heterocyclic group in the definition of Het can be substituted with the above substituent, a nitrogen atom of the heterocyclic group can further be bonded with an oxygen atom to form N-oxide. Moreover, a nitrogen atom and a carbon atom of the heterocyclic group may be substituted with a straight or branched alkyl group having 1 to 4 carbon atoms. Such alkyl group includes a methyl group.

In the definition of the compound of the formula (1), Het is the heterocyclic group which may be substituted with the above substituent, that is, a 4- to 10-membered, monocyclic or condensed cyclic aliphatic or aromatic group containing 1, 2, 3 or 4 identical or different hetero atoms, such as an oxygen atom, a nitrogen atom and a sulfur atom, preferably a 4- to 6-membered monocyclic aliphatic or aromatic group containing 1, 2, 3 or 4 identical or different hetero atoms, such as an oxygen atom, a nitrogen atom and a sulfur atom.

Such heterocyclic group includes, for example, a group derived from a heterocyclic compound such as oxetane, furan, dihydrofuran, tetrahydrofuran, pyran, dihydropyran, tetrahydropyran, dioxole, thiophene, dihydrothiophene, tetrahydrothiophene, thiopyran, dihydrothiopyran, tetrahydrothiopyran, pyrrole, dihydropyrrole, pyrrolidine, pyridine, dihydropyridine, tetrahydropyridine, piperidine, pyrazole, 2-pyrazoline, pyrazolidine, imidazole, imidazolidine, pyrimidine, pyrazine, oxazoline, piperazine, 1,2,3-triazole, 1,2,4-triazole, tetrazole, isoxazole, 1,3-oxazole, 1,2,3-oxadiazole, 1,2,4-oxadiazole, 1,2,5-oxadiazole, 1,3,4-oxadiazole, 1,2-thiazole, 1,3-thiazole, 1,2,3-thiadiazole, 1,2,4-thiadiazole, 1,2,5-thiadiazole, 1,3,4-thiadiazole, 1,3-dioxolan, oxazolidine and morpholine. Among them, Het includes a 5- or 6-membered, monocyclic aliphatic heterocyclic group or aromatic heterocyclic group, which may be substituted with the above group, and contains 1, 2 or 3 identical or different hetero atoms selected from an oxygen atom, a nitrogen atom and a sulfur atom, and particularly includes a group which may be substituted with the above group, derived from furan, 1,3-thiazole, 1,3-oxazole, 1,3,4-oxadiazole, pyrimidine, tetrahydrofuran, 5,6-dihydropyran, pyridine, 1,2,4-triazole, 1,2,4-oxadiazole and tetrahydropyran.

Of Het having the heterocyclic group listed above, preferred is the compound of the general formula (1) in which Het is a 5- or 6-membered, monocyclic unsaturated aliphatic heterocyclic group or aromatic heterocyclic group, which may be substituted with the above group, and contains, identically or differently, 1, 2 or 3 nitrogen atoms and/or oxygen atoms and can further contain 1 sulfur atom, The compound of the general formula (1) in which Het is a group derived from furan, 1,3-thiazole, 1,3-oxazole, 1,3,4-oxadiazole, pyridine, pyrimidine or 5,6-dihydropyran, which may be substituted with the above group, is preferred in terms of activity. Of the compound of the above general formula (1), a compound in which the heterocyclic group of Het is substituted with a carboxyl group or a nitrogen atom of the nitrogen atom-containing heterocyclic group of Het is N-oxide is preferred in terms of water solubility or oral absorption.

Further, in a group: —(CH$_2$)$_n$— bonded to the above Het group, n represents 0, 1 or 2, preferably 0 or 1.

In the definition of the compound represented by the general formula (1), while $A_1$ and $A_2$ each independently represent —CH═ or —N═, $A_1$ is preferably —CH═.

Further, while $R_2$ represents a straight or branched alkyl group having 1 to 3 carbon atoms, the group includes a methyl group, an ethyl group, an n-propyl group and an i-propyl group. Among them, a methyl group is preferred.

Furthermore, while $A_3$ represents —$CH_2$—, —(C=O)— or —$SO_2$—, —$CH_2$— and —$SO_2$— are preferred and —$C_2$— is particularly preferred. When $A_1$ and $A_2$ both represent —CH=, $A_3$ represents —$CH_2$— or —$SO_2$—.

While $R_1$ is selected from 9 types of the group described in the definition of the general formula (1) as described above, particularly there may be mentioned a compound of the general formula (1) in which $R_1$ is a 4-fluorophenyl group.

In the compound of the general formula (1), a group: $R_1$-$A_3$— is preferably a 4-fluorobenzyl group.

Examples of —$(CH_2)_n$-Het in the general formula (1) of the compound according to the present invention are shown in the following Table 1 to 10:

TABLE 1

TABLE 1-continued

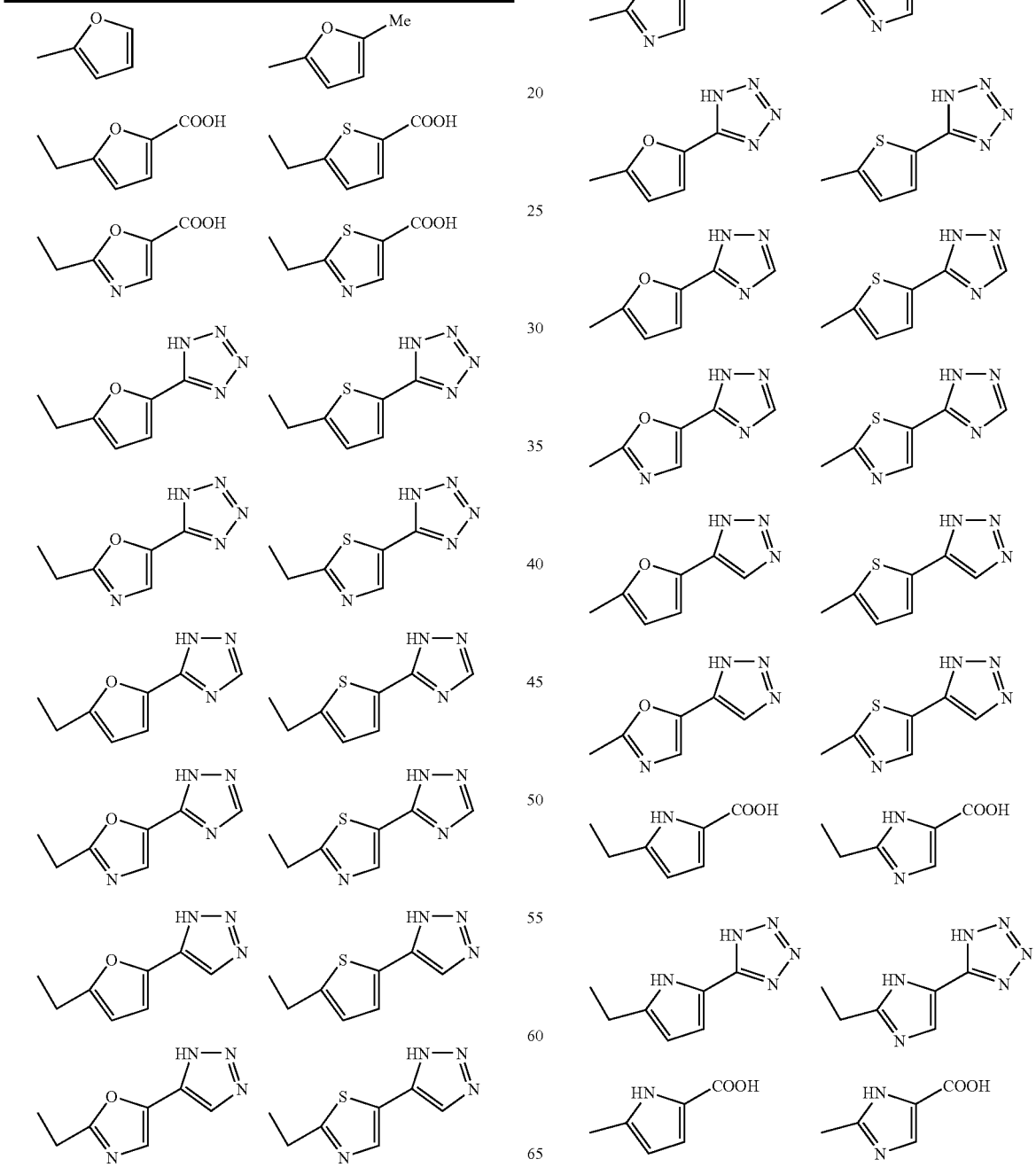

TABLE 1-continued
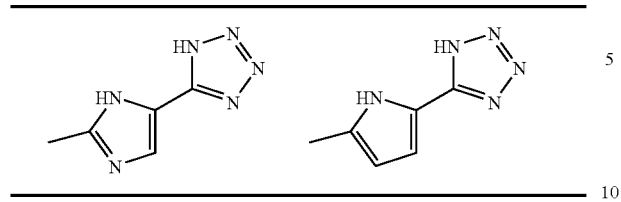
TABLE 2
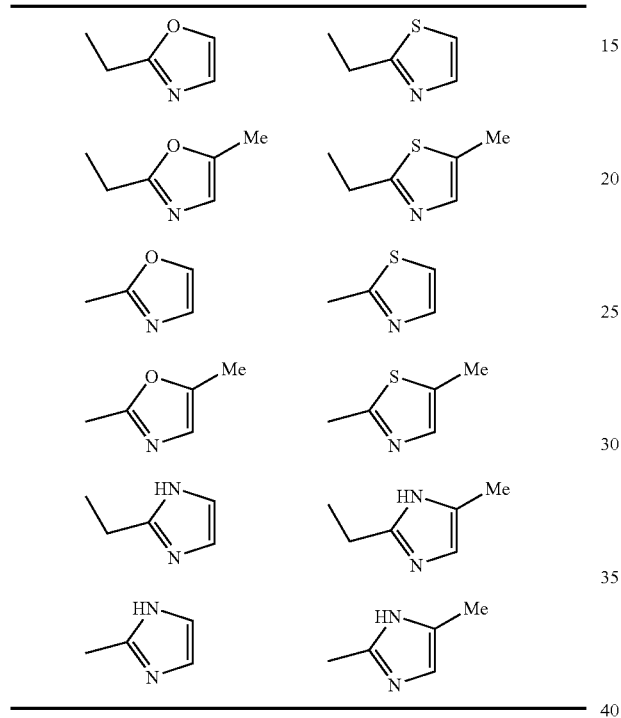
TABLE 3
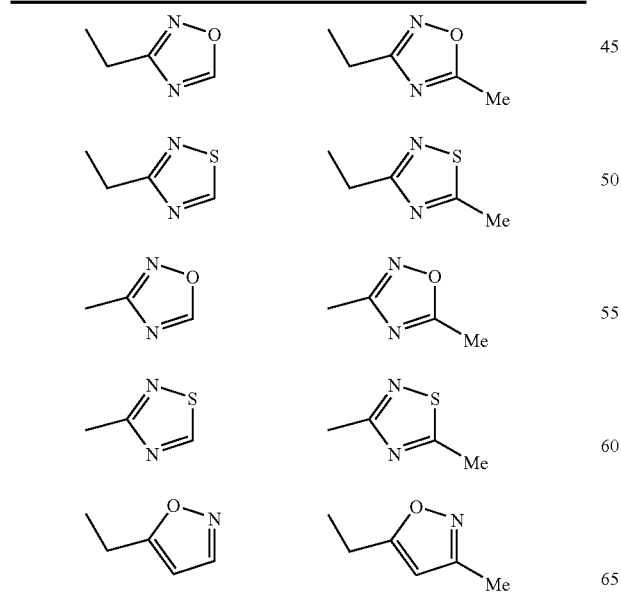
TABLE 3-continued
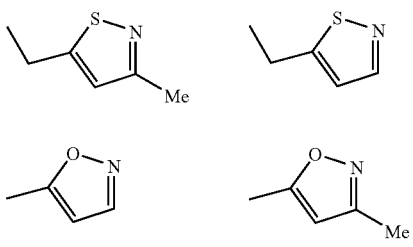
TABLE 4
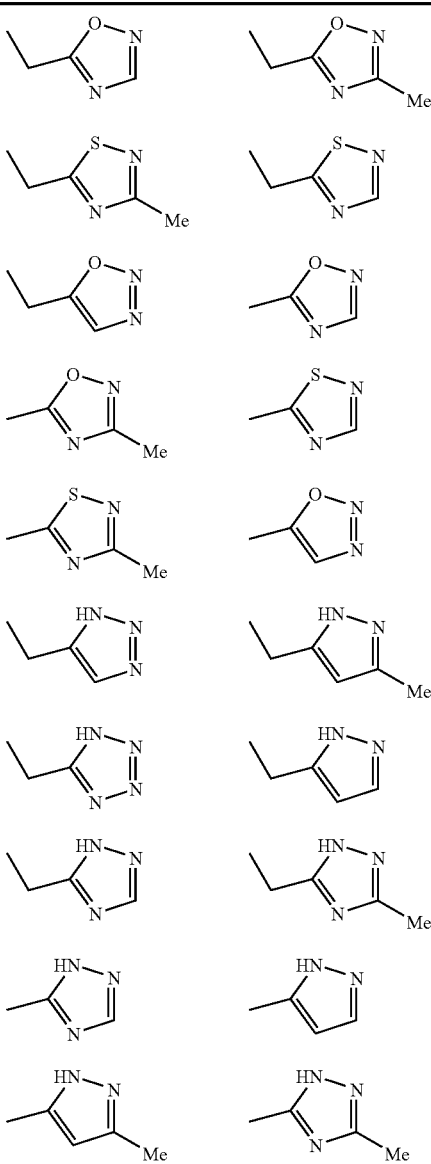

TABLE 4-continued
TABLE 5
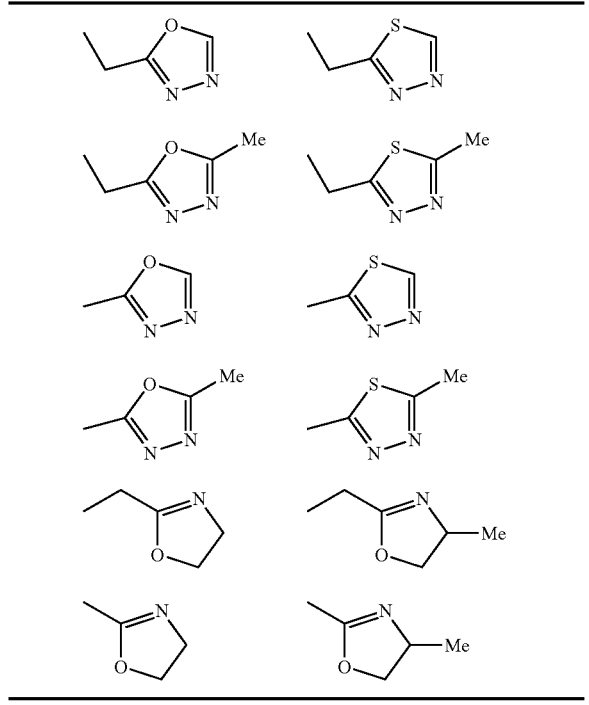
TABLE 6
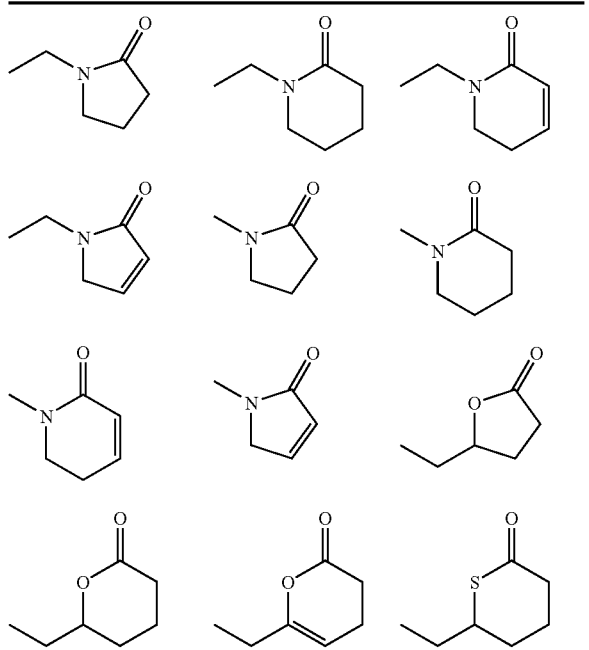
TABLE 6-continued
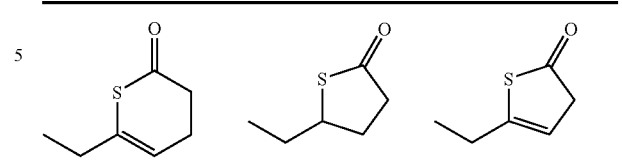
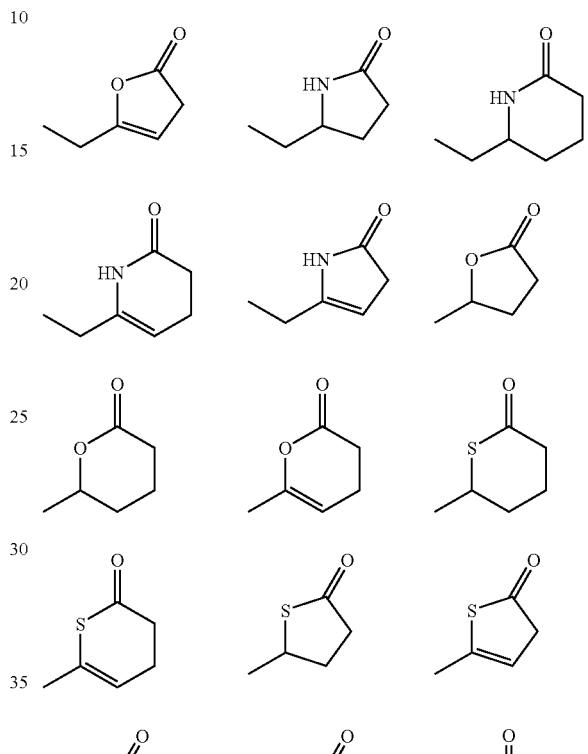
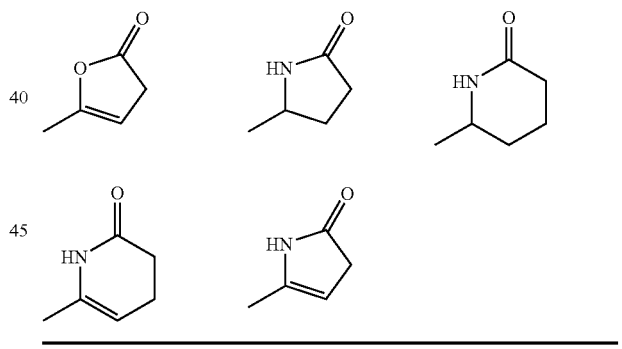
TABLE 7
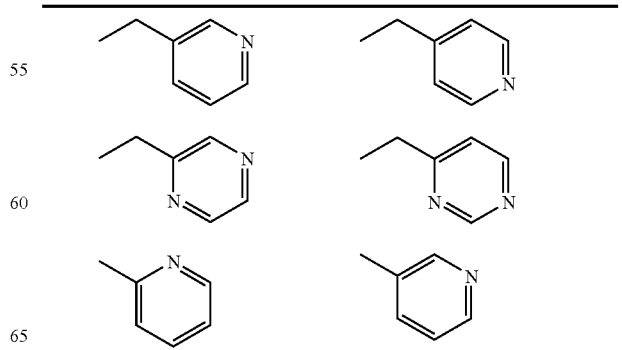

TABLE 7-continued

TABLE 8-continued

TABLE 8

TABLE 9

TABLE 10

TABLE 10-continued

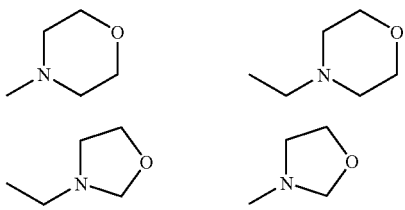

Preferred —(CH$_2$)$_n$-Het includes a 1,3-thiazol-2-yl group, a 1,3-oxazol-2-yl group, a 1,3,4-oxadiazol-2-yl group, a 2-furyl group, a 2-pyridyl group, a 2-pyrimidinyl group, a 5-methylfuran-2-yl group, a 2-tetrahydrofuranyl group, a 5,6-dihydro-2H-4-pyranyl group, a 5-methylaminocarbonylpyridin-2-yl group and a 5-fluoropyrimidin-4-yl group.

The compound represented by the general formula (1) preferably includes the following:

a compound selected from
2-(2-furyl)-1-(4-fluorobenzyl)-5-methanesulfonyl-1H-pyrrolo [2,3-b]pyridine;
1-(4-fluorobenzyl)-5-methanesulfonyl-2-(thiazol-2-yl)indole;
1-(4-fluorobenzyl)-2-(oxazol-2-yl)-5-methanesulfonyl-1H-pyrrolo[2,3-b]pyridine;
1-(4-fluorobenzyl)-5-methanesulfonyl-2-([1,3,4]oxadiazol-2-yl)indole;
5-methanesulfonyl-2-(2-pyridyl)-1-(4-fluorobenzyl)-1H-pyrrolo[2,3-b]pyridine;
1-(4-fluorobenzyl)-5-methanesulfonyl-2-(2-pyrimidinyl)-1H-pyrrolo[2,3-b]pyridine;
1-cyclohexylmethyl-5-methanesulfonyl-2-(2-pyrimidinyl)-1H-pyrrolo[2,3-b]pyridine;
2-(2-furanyl)-1-(4-fluorobenzyl)-5-methanesulfonyl-indole;
1-cyclohexylmethyl-2-(2-furanyl)-5-methanesulfonyl-indole;
2-(2-furanyl)-5-methanesulfonyl-1-(2-pyridylmethyl)-1H-pyrrolo[2,3-b]pyridine;
1-(4-fluorobenzyl)-5-methanesulfonyl-2-(5-methylfuran-2-yl)-1H-pyrrolo[2,3-b]pyridine;
2-(2-furanyl)-1-cyclohexylmethyl-5-methanesulfonyl-1H-pyrrolo[2,3-b]pyridine;
2-(2-tetrahydrofuranyl)-1-(4-fluorobenzyl)-5-methanesulfonyl-indole;
2-(5,6-dihydro-2H-4-pyranyl)-1-(4-fluorobenzyl)-5-methanesulfonyl-indole;
1-(4-fluorobenzyl)-5-methanesulfonyl-2-(5-methoxycarbonylpyridin-2-yl)indole;
1-(4-fluorobenzyl)-2-(5-carboxypyridin-2-yl)-5-methanesulfonylindole;
1-(4-fluorobenzyl)-5-methanesulfonyl-2-(5-methylaminocarbonylpyridin-2-yl)indole;
1-(4-fluorobenzyl)-5-methanesulfonyl-2-(3-pyridylmethyl)indole;
1-(4-fluorobenzyl)-5-methanesulfonyl-2-(3-pyridyl)indole;
1-(4-fluorobenzyl)-5-methanesulfonyl-2-(1-oxy-3-pyridyl)indole;
1-(4-fluorobenzenesulfonyl)-5-methanesulfonyl-2-(thiazol-2-yl)indole;
1-(4-fluorobenzyl)-5-methanesulfonyl-2-(5-methyl-[1,2,4]triazol-3-yl)indole;
1-(4-fluorobenzyl-5-methanesulfonyl-2-(3-methyl-[1,2,4]oxadiazol-5-yl)indole;
1-(4-fluorobenzyl)-5-methanesulfonyl-2-(5-methyl-[1,2,4]oxadiazol-3-yl)indole;
1-(4-fluorobenzyl)-5-methanesulfonyl-2-(tetrahydropyran-4-yl)indole;
5-methanesulfonyl-2-(1-oxy-2-pyridyl)-1-(4-fluorobenzyl)-1H-pyrrolo[2,3-b]pyridine;
1-(4-fluorobenzyl)-5-methanesulfonyl-2-(2-thiazolylmethyl)indole;
6-(1-(4-fluorobenzyl)-5-methanesulfonyl-1H-pyrrolo [2,3-b]pyridin-2-yl) nicotinic acid methylamide;
2-(2-carboxyfuran-5-yl)-1-(4-fluorobenzyl)-5-methanesulfonyl-indole;
2-(2-carboxyfuran-5-ylmethyl)-1-(4-fluorobenzyl)-5-methanesulfonylindole;
1-(4-fluorobenzyl)-5-methanesulfonyl-2-(4-pyridyl) indole;
1-(4-fluorobenzyl)-5-methanesulfonyl-2-(1-oxy-4-pyridyl) indole;
1-(4-fluorobenzyl)-5-methanesulfonyl-2-([1,3,4]oxadiazol-2-yl)-1H-pyrrolo[2,3-b]pyridine;
5-(4-fluorobenzyl)-2-methanesulfonyl-6-(thiazol-2-yl)-5H-pyrrolo[2,3-b]pyrazine;
5-(4-fluorobenzyl)-2-methanesulfonyl-6-(oxazol-2-yl)-5H-pyrrolo[2,3-b]pyrazine;
1-(4-fluorobenzyl)-5-methanesulfonyl-2-(5-fluoropyrimidin-4-yl)-1H-pyrrolo[2,3-b]pyridine; and
1-(2,4-difluorobenzyl)-5-methanesulfonyl-2-([1,3,4]oxadiazol-2-yl)-1H-pyrrolo[2,3-b]pyridine, or addition salts thereof with a pharmaceutically acceptable acid or base, or hydrates thereof.

Among the above compounds, 1-(4-fluorobenzyl)-5-methanesulfonyl-2-(thiazol-2-yl)indole; 1-(4-fluorobenzyl)-2-(oxazol-2-yl)-5-methanesulfonyl-1H-pyrrolo [2,3-b]pyridine; and 1-(4-fluorobenzyl)-5-methanesulfonyl-2-([1,3,4] oxadiazol-2-yl)indole and addition salts thereof with a pharmaceutically acceptable acid or base, and hydrates thereof are particularly preferred.

The compound of the present invention can be prepared by the method of the reaction scheme 1 or 2 described below or the methods which are suitably partially modified according to the desired compound to be prepared, or any other suitable methods, starting from known compounds. The compound of the present invention can be also obtained by suitably applying specific preparation methods described in Examples.

Of the compounds of the present invention, the compound in which A$_3$ is —CH$_2$— and n is 0 can be prepared based on the following reaction scheme 1 by using a reagent having a desired group.

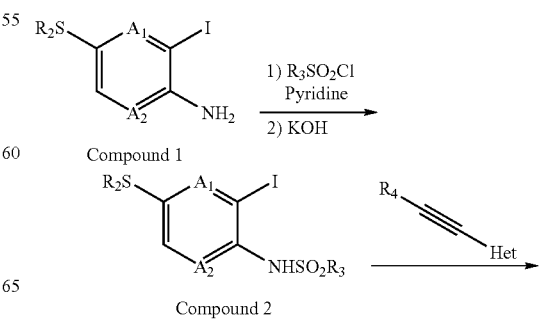

Reaction scheme 1

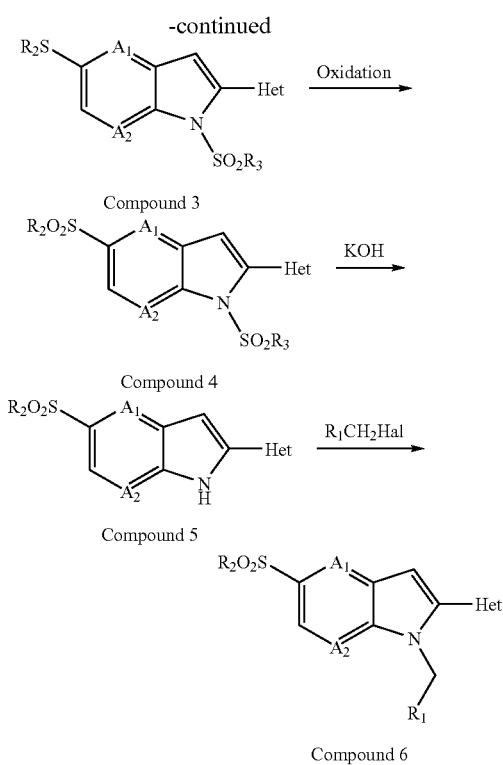

[wherein R₃ represents a methyl group, a phenyl group or a 4-methylphenyl group; R₄ represents a hydrogen atom or a trimethylsilyl group; Hal represents a halogen atom, such as a chlorine atom, a bromine atom and an iodine atom; and other symbols are as defined in the general formula (1)].

In the reaction scheme 1, the conversion of Compound 1 (for example, described in WO98/51,667 and Japanese Patent Application Disclosure Hei No. 11-29553, Example III-1) to Compound 2 can be carried out by reacting Compound 1 with a compound R₃SO₂Cl (in which R₃ represents a methyl group, a phenyl group or a 4-methylphenyl group) in the presence of a base, followed by base treatment and hydrolysis. The base employable with R₃SO₂Cl includes pyridine, 4-dimethylaminopyridine, triethylamine, tripropylamine, tributylamine and diisopropylethylamine, preferably pyridine. The reaction solvent employable includes dichloromethane, chloroform, 1,2-dichloroethane, benzene, toluene, xylene, tetrahydrofuran or 1,4-dioxane, whereas the reaction can be and is preferably carried out without any solvents. The reaction is carried out at 0 to 100° C., preferably 10 to 80° C. The base employable in hydrolysis includes potassium hydroxide, sodium hydroxide, lithium hydroxide, potassium carbonate, sodium carbonate and lithium carbonate, preferably potassium hydroxide. The reaction solvent employable in hydrolysis includes water, methanol, ethanol, isopropanol, tetrahydrofuran, 1, 4-dioxane and acetonitrile in a single form or a mixed solvent. A mixed solvent of water, methanol and 1,4-dioxane is preferably used. The reaction is carried out at 0, to 100° C., preferably 10 to 80° C.

The conversion of Compound 2 to Compound 3 can be carried out by reacting Compound 2 with an acetylene compound R₄—C≡C-Het (in which R₄ represents a hydrogen atom or a trimethylsilyl group) having the desired group Het in the presence of a palladium catalyst, a copper reagent and a base. The palladium catalyst employable includes bis(triphenylphosphine)palladium chloride, bis(triphenylphosphine)palladium acetate, bis(acetonitrile)palladium chloride and bis(benzonitrile)palladium chloride, preferably bis(triphenylphosphine)palladium chloride. The copper reagent employable includes copper(O), copper(II) acetate, copper(I) bromide, copper(II) bromide, copper(I) chloride, copper(II) chloride, copper(I) iodide, copper(II) iodide, copper(I) oxide, copper(II) oxide and copper(II) sulfate, preferably copper(I) iodide. The base employable includes triethylamine, tripropylamine, tributylamine, diisopropylethylamine, triisobutylamine, diethylamine, dipropylamine, dibutylamine, potassium carbonate, sodium carbonate, sodium hydrogencarbonate and potassium hydrogencarbonate, preferably triethylamine. The reaction solvent employable includes 1,4-dioxane, N,N-dimethylformamide, acetonitrile, N,N-dimethylacetamide, tetrahydrofuran, dimethoxyethane, benzene, toluene and dimethyl sulfoxide. The reaction can also be carried out using no solvents. The reaction is preferably carried out using 1,4-dioxane or N,N-dimethylformamide, or using no solvents. The reaction is carried out at 15 to 150° C., preferably 40 to 120° C.

The conversion of Compound 3 to Compound 4 can be carried out by oxidizing Compound 3. The oxidizing agent employable includes OXONE (registered trademark), m-chloroperbenzoic acid, magnesium monoperoxyphthalate and so forth. As the reaction solvent, there may be used tetrahydrofuran, ether, dimethoxyethane, 1,4-dioxane, dichloromethane, chloroform, methanol, ethanol, water and so forth singly or in a form of mixed solvent. When OXONE is used, a mixed solvent of tetrahydrofuran and water or of tetrahydrofuran, methanol and water is preferably employed; when m-chloroperbenzoic acid is used, dichloromethane is preferably employed; and when magnesium monoperoxyphthalate is used, a mixed solvent of dichloromethane and methanol is preferably employed. The reaction is carried out at −10 to 60° C., preferably 0 to 40° C.

The oxidizing reaction can be carried out at any steps in the reaction scheme 1 when it satisfies the condition that it is conducted before the step of base treatment (including the corresponding steps) in the conversion of Compound 4 to Compound 5 described later.

The conversion of Compound 4 to Compound 5 can be carried out by the base treatment of Compound 4 and elimination of the group —SO₂R₃. The base employable includes potassium hydroxide, sodium hydroxide, lithium hydroxide, potassium carbonate, sodium carbonate, lithium carbonate and so forth, preferably potassium hydroxide. As the reaction solvent, there may be used water, methanol, ethanol, isopropanol, tetrahydrofuran, 1,4-dioxane, acetonitrile and so forth singly or in a form of mixed solvent. Preferred is methanol alone; a mixed solvent of water and methanol; a mixed solvent of water, 1,4-dioxane and tetrahydrofuran; or a mixed solvent of water, methanol and tetrahydrofuran. The reaction is carried out at 0 to 100° C., preferably 15 to 100° C.

The elimination reaction of the group —SO₂R₃ can be carried out at any steps in the reaction scheme 1 if conditions are satisfied such that it is carried out after the step of oxidation (including the corresponding steps) in the conversion of Compound 3 to Compound 4 described before and before the step of introducing the group R₁CH₂— (including the corresponding steps) in the conversion of Compound 5 to Compound 6 described later. When the substituent at the position relative to the 5-position on the indole ring is R₂O₂S—, the elimination reaction may occur accompanied by other reactions.

The conversion of Compound 5 to Compound 6 can be carried out by the base treatment of Compound 5, which is subsequently followed by the treatment with the compound $R_1CH_2Hal$ having the desired group $R_1$ (in which Hal represents a halogen atom, such as a chlorine atom, a bromine atom and an iodine atom) to introduce the group $R_1CH_2$—. The base employable includes sodium hydride, potassium hydride, sodium methoxide, sodium ethoxide, potassium-t-butoxide, lithium diisopropylamide, lithium bis(trimethylsilyl)amide and so forth, preferably sodium hydride or lithium diisopropylamide. The reaction solvent employable includes N,N-dimethylformamide, N,N-dimethylacetamide, tetrahydrofuran, dimethoxyethane, dimethyl sulfoxide, ether and so forth, preferably N,N-dimethylformamide or tetrahydrofuran. The reaction is carried out at −78 to 50° C., preferably −78 to 30° C.

When the compound $R_1COHal$ or $R_1SO_2Hal$ is used instead of the compound $R_1CH_2Hal$, the compound of the general formula (1) (wherein $A_3$ represents —(C=O)— or —$SO_2$—) can be obtained. The base, the reaction solvent and reaction temperature employable here are similar to those used in the introduction of the group $R_1CH_2$—.

Of the compounds according to the present invention, the compound in which $A_3$ is —$CH_2$— and n is 1 can be prepared based on the following reaction scheme 2 by using the reagent having the desired group.

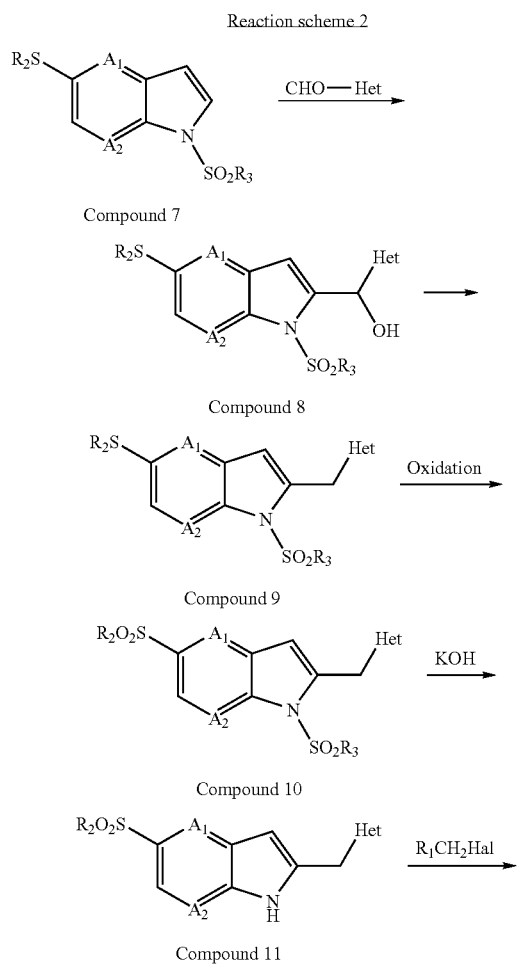

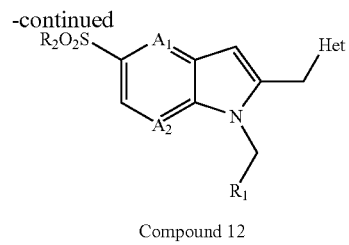

Compound 12

[wherein $R_3$ represents a methyl group, a phenyl group or a 4-methylphenyl group; Hal represents a halogen atom, such as a chlorine atom, a bromine atom and an iodine atom; and other symbols are as defined in the general formula (1)].

In the reaction scheme 2, conversion of Compound 7 (described in WO98/51667 and Example I-1 of Japanese Patent Application Disclosure Hei No. 11-29553) to Compound 8 can be carried out by reacting Compound 7, after the base treatment, with aldehyde CHO-Het having the desired group Het to bind the group Het to Compound 7 via a methylene group. The base employable includes lithium diisopropylamide, lithium bis(trimethylsilyl)amide, n-butyl lithium, sec-butyl lithium, tert-butyl lithium and so forth, preferably lithium diisopropylamide and n-butyl lithium. The reaction solvent employable includes tetrahydrofuran, ether and so forth, preferably tetrahydrofuran. The reaction is carried out at −78 to 50° C., preferably −78 to 30° C.

By using the compound having a formyl group at the position corresponding to the 2-position in the indole ring and the compound Het-Hal substituted with a halogen atom, such as a chlorine atom, a bromine atom and an iodine atom, Compound 8 can be also obtained by subjecting them to the steps similar to those of the conversion reaction of Compound 7 to Compound 8.

Further, the compound represented by the formula (1), wherein n is 2, can be obtained by using the compound CHO—$CH_2$-Het instead of the compound CHO-Het.

Furthermore, the compound represented by the formula (1), wherein n is 0, can be obtained by usingHet having the —(C=O)— partial structure instead of the compound CHO-Het.

The conversion of Compound 8 to Compound 9 can be carried out by oxidizing Compound 8 to be ketones, followed by reduction with hydrazine, or by catalytic reduction of Compound 8. The oxidizing agent employable for oxidization to allow Compound 8 to be ketones include Des Martin reagent (1,1,1-tris(acetyloxy)-1,1-dihydro-1,2-benziodoxol-3(1H)-one), manganese dioxide, chromic acid, pyridinium dichromate, pyridinium chlorochromate, the combination of dimethyl sulfoxide, oxalyl chloride and triethylamine and so forth, preferably Des Martin reagent (1,1,1-tris(acetyloxy)-1, 1-dihydro-1,2-benziodoxol-3(1H)-one) and manganese dioxide. The reaction solvent employable includes dichloromethane, chloroform, 1,2-dichloroethane, acetone and so forth, preferably dichloromethane. The reaction is carried out at −78 to 50° C., preferably −78 to 30° C. The reduction with hydrazine can be carried out in the presence of a base. The base employable includes potassium hydroxide, sodium hydroxide, lithium hydroxide and so forth, preferably potassium hydroxide. The reaction solvent employable includes ethylene glycol, ethanol, methanol, isopropanol and so forth, preferably ethylene glycol. The reaction is carried out at 15 to 150° C., preferably 40 to 120° C. The catalyst employable in the catalytic reduction includes palladium carbon, palladium hydroxide, palladium black and so forth, preferably palladium carbon. As the reaction solvent, ethanol, methanol, ethyl acetate and so forth are used in the presence or absence of acetic acid, and ethanol is preferably used in the presence of acetic acid. The reaction is carried out at 0 to 80° C., preferably 15 to 60° C. under a pressure of 1 to 5 atm, preferably 1 atm.

Conversion of Compound 9 to Compound 10 is carried out by oxidizing Compound 9. The oxidizing agent employable includes OXONE (registered trademark), m-chloroperbenzoic acid, magnesium monoperoxyphthalate and so forth. As the reaction solvent, there may be used tetrahydrofuran, ether, dimethoxyethane, 1,4-dioxane, dichloromethane, chloroform, methanol, ethanol, water and so forth singly or in the form of mixed solvent. When OXONE is used, a mixed solvent of tetrahydrofuran and water or of tetrahydrofuran, methanol and water is preferably employed; when m-chloroperbenzoic acid is used, dichloromethane is preferably employed, and when magnesium monoperoxyphthalate is used, a mixed solvent of dichloromethane and methanol is preferably employed. The reaction is carried out at −10 to 60° C., preferably 0 to 40° C.

The conversion step of Compound 8 to Compound 9 and that of Compound 9 to Compound 10 are interchangeable.

Conversion of Compound 10 to Compound 11 can be carried out by the base treatment of Compound 10. The base employable includes potassium hydroxide, sodium hydroxide, lithium hydroxide, potassium carbonate, sodium carbonate, lithium carbonate and so forth, preferably potassium hydroxide. As the reaction solvent, there may be used water, methanol, ethanol, isopropanol, tetrahydrofuran, 1,4-dioxane, acetonitrile and so forth singly or in the form of mixed solvent. Preferred is methanol alone, a mixed solvent of water and methanol; a mixed solvent of water, 1,4-dioxane and tetrahydrofuran; or a mixed solvent of water, methanol and tetrahydrofuran. The reaction is carried out at 0 to 100° C., preferably 15 to 100° C.

Conversion of Compound 11 to Compound 12 can be carried out by the base treatment of Compound 11, which is subsequently followed by the treatment with the compound $R_1CH_2Hal$ (in which Hal represents a halogen atom, such as a chlorine atom, a bromine atom and an iodine atom) having the desired group $R_1$. The base employable includes sodium hydride, potassium hydride, sodium methoxide, sodium ethoxide, potassium-t-butoxide, lithium diisopropylamide, lithium bis(trimethylsilyl)amide and so forth, preferably sodium hydride or lithium diisopropylamide. The reaction solvent employable includes N,N-dimethylformamide, N,N-dimethylacetamide, tetrahydrofuran, dimethoxyethane, dimethyl sulfoxide, ether and so forth, preferably N,N-dimethylformamide or tetrahydrofuran. The reaction is carried out at −78 to 50° C., preferably, −78 to 30° C.

When the compound $R_1COHal$ or $R_1SO_2Hal$ is used instead of the compound $R_1CH_2Hal$, the compound of the general formula (1) (wherein $A_3$ is —(C=O)— or —$SO_2$—, respectively) can be obtained. The base, the reaction solvent and reaction temperature employable here are similar to those used in the introduction of the group $R_1CH_2$—.

The heterocyclic group represented, by Het of Compound 6, or Compound 12 represented by the general formula (1) obtained in the reaction scheme 1 or 2, can be converted by the following methods.

The conversion of a double bond in Het to a single bond can be carried out by catalytic reduction of the compound having the double bond. The catalyst employable in the catalytic reduction includes palladium carbon, palladium hydroxide, palladium black and so forth, preferably palladium carbon. As the reaction solvent, there may be used ethanol, methanol, ethyl acetate, acetic acid and so forth singly or in the form of mixed solvent, preferabley ethanol. The reaction is carried out at 0 to 80° C., preferably 15 to 60° C.

Conversion of an alkyl ester to other alkyl esters in the case where Het has a substituent —$COOR_4$ (in which $R_4$ represents a straight or branched alkyl group having 1 to 3 carbon atoms) can be carried out by effecting a base on the alkyl ester in an alcohol having the desired alkyl group. The base employable includes potassium hydroxide, sodium hydroxide, lithium hydroxide, potassium carbonate, sodium carbonate, lithium carbonate and so forth, preferably potassium hydroxide. As the reaction solvent, there may be used methanol, ethanol, isopropanol, tetrahydrofuran, 1,4-dioxane, acetonitrile and so forth singly or in the form of mixed solvent, preferably methanol. The reaction is carried out at 0 to 100° C., preferably 15 to 100° C.

Conversion of an alkyl ester to a carboxylic acid in the case where Het has the substituent —$COOR_4$ can be carried out by effecting a base on the alkyl ester. The base employable includes potassium hydroxide, sodium hydroxide, lithium hydroxide, potassium carbonate, sodium carbonate, lithium carbonate and so forth, preferably potassium hydroxide and lithium hydroxide. As the reaction solvent, there may be used water, methanol, ethanol, isopropanol, tetrahydrofuran, 1,4-dioxane, acetonitrile and so forth singly or in the form of mixed solvent, preferabley methanol. The reaction is carried out at 0 to 100° C., preferably 15 to 100° C.

Conversion of a carboxyl group to the group —$CONR_4R_6$ in the case where Het has the substituent, a carboxyl group (in which $R_5$ and $R_6$ may be the same or different and each represent a hydrogen atom or a straight or branched alkyl group having 1 to 3 carbon atoms) can be carried out by converting the carboxyl group to an acid chloride, and subsequently reacting it with amine $HNR_5R_6$ having the desired group in the presence or absence of a base. The reagent employable for the conversion to the acid chloride includes thionyl chloride, oxalyl chloride, phosphorous oxychloride, phosphorous pentachloride and so forth, preferably thionyl chloride. The reaction is carried out at 0 to 120° C., preferably 20 to 100° C. The base employable in the reaction with amine includes triethylamine, diisopropylethylamine, pyridine and so forth, preferably triethylamine. As the reaction solvent employable in the reaction with amine, there may be used methanol, ethanol, tetrahydrofuran, dioxane, dimethoxyethane, dichloromethane, chloroform and so forth singly or in the form of mixed solvent, preferably tetrahydrofuran. The reaction is carried out at −10 to 50° C., preferably 0 to 30° C.

Further, the conversion of the carboxyl group to the group —$CONR_5R_6$ in the case where Het has the substituent, a carboxyl group can be carried out by treating the carboxyl group with a condensation agent and subsequently with amine $HNR_5R_6$ having the desired group. The condensation agent employable includes 1,1'-carbonyldiimidazole, benzotriazol-1-yloxy-tris(dimethylamino)phosphonium hexafluorophosphate, dicyclohexylcarbodiimide, diethyl cyanide phosphate and so forth, preferably 1,1'-carbonyldiimidazole or benzotriazol-1-yloxy-tris(dimethylamino)phosphonium hexafluorophosphate. As the reaction solvent, there may be used methanol, ethanol, tetrahydrofuran, dioxane, dimethoxyethane, dichloromethane, chloroform and so forth singly or in the form of mixed solvent, preferably tetrahydrofuran or dichloromethane. The reaction is carried out at −10 to 50° C., preferably 0 to 30° C.

Furthermore, the conversion of the carboxyl group to the group —$CONR_5R_6$ in the case where Het has the substituent, a carboxyl group can be carried by treating the carboxyl group with chlorocarbonate and a base and subsequently with an amine $HNR_5R_6$ having the desired group. The chlorocarbonate employable includes methyl chlorocarbonate, ethyl chlorocarbonate and so forth, preferably ethyl chlorocarbonate. The base employable includes triethylamine, diisopropylethylamine, pyridine and so forth, preferably triethylamine. As the reaction solvent, there may be used tetrahydrofuran, dioxane, dimethoxyethane, dichloromethane, chloroform and so forth sigly or in the form of mixed solvent, preferably tetrahydrofuran. The reaction is carried out at −10 to 50° C., preferably 0 to 30° C.

Conversion to pyridine N-oxide in the case where Het is a group derived from pyridine can be carried out by oxidizing the pyridine derivative. The oxidizing agent employable includes m-chloroperbenzoic acid, magnesium monoperoxyphthalate and so forth. As the reaction solvent, there may be used dichloromethane, chloroform, 1,2-dichloroethane, methanol, ethanol and so forth singly or in the form of mixed solvent. When m-chloroperbenzoic acid is used, dichloromethane is preferably employed, and when magnesium monoperoxyphthalate is used, a mixed solvent of dichloromethane and methanol is preferably employed. The reaction is carried out at −10 to 60° C., preferably 0 to 40° C.

The reagent used in the above reaction schemes 1 and 2 is known or can be synthesized according to the known methods or methods which can be easily attained by those skilled in the art from the known methods. Further, they can be also synthesized by referring to the method described in Examples of the present application.

The compound of the present invention has a cyclooxygenase 2 (COX-2) inhibitory action and is useful as an anti-inflammatory agent. The compound of the present invention can be administered orally or parenterally. The dosage is 3 to 150 mg/kg per day for an oral administration and 1 to 50 mg/kg per day for a parenteral administration.

When the compound is administered as a pharmaceutical, it can be prepared using usual formulation techniques and used in a dosage form of solid or liquid, such as tablets, capsules, powders, granules, suppositories, solution, suspension or emulsion.

Further, in this case, additive components which are customarily used for pharmaceutical preparations such as excipients, disintegrators, lubricants, binders, preservatives, stabilizers, osmotic pressure regulating agents and so forth can be used.

An example of these additive components include, glucose, lactose, starches, carboxymethylcellulose, magnesium stearate, talc, liquid paraffin, polyvinyl alcohol, vegetable oil, polyalkylene glycol and so forth. Other pharmaceutical ingredients can be also included.

The preparation of the compound of the present invention will be described below in more details based on Examples.

EXAMPLE 1

2-(2-Furyl)-1-(4-fluorobenzyl)-5-methanesulfonyl-1H-pyrrolo[2,3-b]pyridine

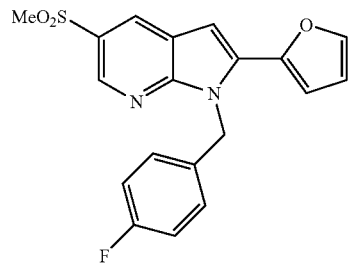

(1) Preparation of 2-benzenesulfonylamino-3-iodo-5-methylthiopyridine

To a solution of 2-amino-3-iodo-5-methylthiopyridine (7.63 g) in pyridine (30 ml), benzenesulfonyl chloride (7.9 ml) was added at 15 to 30° C. under nitrogen atmosphere and the mixture was stirred at 60° C. for 15 hours. The reaction solution was then poured into a saturated aqueous sodium hydrogencarbonate solution, extracted with dichloromethane, dried over anhydrous magnesium sulfate, filtered and concentrated under reduced pressure. A solution of the resulting crude bis(benzenesulfonyl) product in a mixture of methanol/dioxane (1:1, 200 ml) was added a 1N aqueous potassium hydroxide solution (64 ml) at 15 to 30° C. and the mixture was stirred at 60° C. for 1 hour. The reaction solution was then poured into a saturated aqueous sodium hydrogencarbonate solution, extracted with dichloromethane, dried over anhydrous magnesium sulfate, filtered and concentrated under reduced pressure. The resulting residue was separated using silica gel column chromatography (methanol:chloroform=1:50) to obtain 6.4 g (56%) of the desired product as a white powder.

$^1$H-NMR (CDCl$_3$) δ: 2.41 (3H, s), 7.47-7.69 (3H, m), 7.90 (1H, brs), 8.13 (4H, m).

(2) Preparation of 2-(2-furyl)-5-methylthio-1-benzenesulfonyl-1H-pyrrolo[2,3-b]pyridine To a solution of 2-benzenesulfonylamino-3-iodo-5-methylthiopyridine (1.60 g) in dioxane (40 ml), 2-ethynylfuran (725 mg), bis(triphenylphosphine) palladium chloride (138 mg), copper(I) iodide (75 mg) and triethylamine (598 mg) were added successively and the mixture was stirred in a sealed tube at 60° C. for 1 hour. After cooling, the reaction solution was poured into water, extracted with dichloromethane, dried over, anhydrous magnesium sulfate, filtered and concentrated under reduced pressure. The resulting residue was separated using silica gel column chromatography (hexane:ethyl acetate=4:1) to obtain 1.24 g (85%) of the desired product as a brown oil.

¹H-NMR (CDCl₃) δ: 2.50 (3H, s), 6.56-6.58 (1H, m), 6.65 (1H, s), 6.79 (1H, d, J=3.3 Hz), 7.43-7.59 (3H, m), 7.62 (1H, s), 7.74 (1H, d, J=2.3 Hz), 8.13 (2H, d, J=7.6 Hz), 8.44 (1H, d, J=2.0 Hz).

(3) Preparation of 2-(2-furyl)-5-methanesulfonyl-1-benzenesulfonyl-1H-pyrrolo[2,3-b]pyridine To a solution of the compound obtained in the step of Example 1 (2) (1.24 g) in a mixture of dichloromethane/methanol (5:1, 120 ml), magnesium monoperoxyphthalate hexahydrate (5.17 g, 80% purity) was added at 0° C. and the mixture was stirred at 0° C. for 30 minutes and at 15 to 30° C. for 1 hour. The reaction solution was then poured into a saturated aqueous sodium hydrogencarbonate solution, extracted with dichloromethane, dried over anhydrous magnesium sulfate, filtered and concentrated under reduced pressure. The resulting residue was separated using silica gel column chromatography (hexane:ethyl acetate 1:1) to obtain 0.89 g (66%) of the desired product as a brown oil.

¹H-NMR (CDCl₃) δ: 3.12 (3H, s), 6.60-6.62 (1H, m), 6.84 (1H, s), 6.86 (1H, d, J=3.3 Hz), 7.51-7.68 (4H, m), 8.26 (2H, d, J=7.26 Hz), 8.40. (1H, d, J=2.3 Hz), 8.99. (1H, d, J=2.0 Hz).

(4) Preparation of 2-(2-furyl)-5-methanesulfonyl-1H-pyrrolo [2,3-b]pyridine

To a solution of the compound obtained in the step of Example 1 (3) (675 mg) in a mixture of tetrahydrofuran/dioxane (5:1, 120 ml), a 1N aqueous potassium hydroxide solution (5 ml) was added-and the mixture was stirred at 60° C. for 15 hours. The reaction solution was then poured into water, extracted with ethyl-acetate, dried over anhydrous magnesium sulfate, filtered and concentrated under reduced pressure to obtain 431 mg. (98%) of the desired product as a brown powder.

¹H-NMR (CDCl₃) δ: 3.17 (3H, s), 6.61-6.62 (1H, m), 6.83 (1H, d, J-1.7 Hz), 6.87 (1H, d, J=3.3,Hz), 7.65 (1H, d, J=1.3 Hz), 8.46 (1H, d, J=2.0 Hz), 8.93 (1H, d, J=1.7 Hz), 11.23 (1H, brs).

(5) Preparation of 2-(2-furyl)-5-methanesulfonyl-1-(4-fluorobenzyl)-1H-pyrrolo[2,3-b]pyridine To a solution of the compound obtained in the step of Example 1 (4) (200 mg) in dimethylformamide (20 ml), sodium hydride (45.8 mg, 60% purity) was added at 0° C. under nitrogen atmosphere, the mixture was stirred for 30 minutes. Subsequently, to the mixture was added 4-fluorobenzyl bromide (288 mg), followed by stirring for 1 hour. The reaction solution was then poured into a saturated aqueous sodium hydrogencarbonate solution and extracted with ethyl acetate. The organic layer was washed with water and a saturated aqueous NaCl solution, dried over anhydrous magnesium sulfate, filtered and concentrated under reduced pressure. The resulting residue was separated using silica gel thin-layer chromatography (methanol:chloroform 1:5.0) to obtain 239 mg (85%) of the desired product as a white powder.

¹H-NMR (CDCl₃) δ: 3.15 (3H, s), 5.82 (2H, s), 6.49-6.51 (1H, m), 6.59 (1H, d, J=3.3 Hz), 6.93-7.07 (5H, m), 7.57 (1H, d, J=1.3 Hz), 8.47 (1H, d, J=2.3 Hz), 8.85 (1H, d, J=2.0 Hz).

EXAMPLE 2

1-(4-Fluorobenzyl)-5-methanesulfonyl-2-(thiazol-2-yl)indole

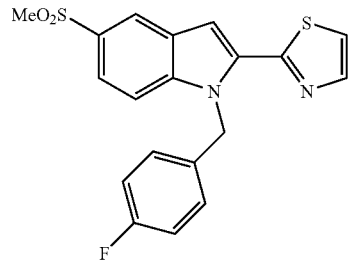

(1) Preparation of 1-benzenesulfonyl-5-methythioindole-2-carboxamide

To a solution of 1-benzenesulfonyl-5-methylthioindole (2 g) in tetrahydrofuran (70 ml), n-butyl lithium (5 ml, 1.59M) was added dropwise at −78° C. under nitrogen atmosphere, the mixture was stirred at the same temperature for 30 minutes, followed by drwopise addition of hexamethylphosphoric triamide (2.3 ml), and the mixture was stirred at the same temperature for 10 minutes. The stirred reaction mixture was heated to 15 to 30° C. over 30 minutes while carbon dioxide gas was blown therein at −78° C. To the reaction mixture was added 1N hydrochloric acid and the resulting mixture was extracted with ethyl acetate. The organic layer was washed with water and dried. The solvent was distilled off under reduced pressure. The resulting residue was separated using silica gel column chromatography (dichloromethane methanol:acetic acid=100:5:1) to obtain a crude product (4 g). To absolution of the resulting crude 1-benzenesulfonyl-5-methylthioindole-2-carboxylic acid (4 g) in tetrahydrofuran (70 ml) was added triethylamine (1.84 ml) and ethyl chlorocarbonate (1 ml) under ice-cooling, the mixture was stirred at the same temperature for 30 minutes, followed by addition of aqueous ammonia (2 ml) at the same temperature. The mixture was stirred for 15 minutes. The reaction mixture was diluted with ethyl acetate, washed with water and dried. The solvent was distilled off under reduced pressure. The resulting residue was recrystallized (hexane/ethyl acetate) to obtain 1.08 g of the desired product as a white powder.

¹H-NMR (CDCl₃) δ: 2.50 (3H, 5), 5.7-5.9 (1H, m), 6.2-6.4 (1H, m), 7.03 (1H, s), 7.3-7.5 (4H, m), 7.55 (1H, t, J=7.3 Hz), 7.93 (2H, d, J=7.3 Hz), 8.05 (1H, d, J=8.6 Hz).

(2) Preparation of 1-benzenesulfonyl-5-methylthioindole-2-carbothioamide

To a solution of the compound obtained in the step of Example 2 (1) (1.08 g) in tetrahydrofuran (30 ml), a Lawesson's reagent (0.9 g) was added and the mixture was heated under reflux for 2 hours. The solvent was distilled off under reduced pressure, and the resulting residue was separated using silica gel column chromatography (dichloromethane) to obtain the desired product (1.1 g) as a yellow powder.

¹H-NMR (CDCl₃) δ: 2.48 (3H, s), 7.2-7.4 (5H, m), 7.4-7.6 (2H, m), 7.71 (2H, d, J=7.6 Hz), 7.8-7.9 (1H, m), 8.08 (1H, d, J=8.6 Hz).

(3) Preparation of 1-benzenesulfonyl-5-methylthio-2-(thiazol-2-yl)indole

A mixture of the compound obtained in the step of Example 2 (2) (50 mg), bromoacetaldehyde dimethylacetal (0.04 ml), p-toluenesulfonic acid (1 mg) and acetic acid (0.5 ml) was stirred at 100° C. for 1 hour. The reaction mixture was concentrated under reduced pressure, diluted with ethyl acetate, washed with water and dried. The solvent was distilled off under reduced pressure. The resulting residue was separated using silica gel column chromatography (hexane:ethyl acetate=1:1) to obtain the desired product (42 mg) as a brown oil.

$^1$H-NMR (CDCl$_3$) δ: 2.50 (3H, s), 6.87 (1H, s), 7.30-7.42 (4H, m), 7.51 (1H, t, J=7.3 Hz), 7.59 (1H, d, J=3.0 Hz), 7.82 (2H, d, J=7.6 Hz), 7.97 (1H, d, J=3.0 Hz), 8.11 (1H, d, J=8.6 Hz).

(4) Preparation of 1-benzenesulfonyl-5-methanesulfonyl-2-(thiazol-2-yl)indole To a mixture of the compound obtained in the step of Example 2 (3) (42 mg), tetrahydrofuran (1 ml) and water (0.5 ml), OXONE (150 mg) was added under ice-cooling and the mixture was stirred for 30 minutes and at 15 to 30° C. for 1.5 hours. To the reaction mixture was added a saturated aqueous sodium hydrogencarbonate solution and the resulting mixture was extracted with ethyl acetate. The organic layer was washed with water and dried. The solvent was distilled off under reduced pressure. The resulting residue was separated using silica gel column chromatography (hexane:ethyl acetate=1:1) to obtain the desired product (39 mg) as a colorless oil.

$^1$H-NMR; (CDCl$_3$) δ: 3.09 (3H, s), 7.03 (1H, s), 7.47 (2H, t, J=7.3 Hz), 7.59 (1H, t, J=7.3 Hz), 7.63 (1H, d, J=3.3 Hz), 7.9-8.0 (3H, m), 8.01 (1H, d, J=3.3 Hz), 8.19 (1H, d, J=1.7 Hz), 8.39 (1H, d, J=8.9 Hz).

(5) Preparation of 5-methanesulfonyl-2-(thiazol-2-yl)indole

To absolution of the compound obtained in the step of Example 2 (4) (39 mg) in methanol (1 ml), a 1N aqueous potassium hydroxide solution (0.2 ml) was added at 15 to 30° C. and the mixture was stirred at 60° C. for 1 hour. To the reaction mixture was added 2N hydrochloric acid and the mixture was extracted with ethyl acetate. The organic layer was washed with water and dried. The solvent was distilled off under reduced pressure to obtain the desired product (27 mg).

$^1$H-NMR (CDCl$_3$) δ: 3.10 (3H, s), 7.16 (1H, s), 7.43 (1H, d, J=3.3 Hz), 7.56 (1H, d, J=8.6 Hz), 7.78 (1H, dd, J=1.3, 8.6 Hz), 7.85 (1H, d, J=3.3 Hz), 8.29 (1H, s), 10.57 (1H, brs).

(6) Preparation of 1-(4-fluorobenzyl)-5-methanesulfonyl-2-(thiazol-2-yl)indole To a solution of the compound obtained in the step of Example 2 (5) (27 mg) in dimethylformamide (1 ml), sodium hydride (10 mg, 60% purity) and 4-fluorobenzyl bromide (0.025 ml) was added under ice-cooling and the mixture was stirred at the same temperature for 30 minutes. To the reaction mixture was added a saturated aqueous ammonium chloride solution and the mixture was extracted with ethyl acetate. The organic layer was washed with water and dried. The solvent was distilled off under reduced pressure. The resulting residue was separated using silica gel column chromatography (hexane:ethyl acetate=1:1) to obtain the desired product (23 mg) as a white powder $^1$H-NMR (CDCl$_3$) δ: 3.09 (3H, s), 6.05 (2H, S), 6.93 (2H, m), 7.06 (2H, m), 7.20 (1H, s), 7.39 (1H, d, J=3.3 Hz), 7.43 (1H, d, J=8.9 Hz), 7.75 (1H, dd, J=2.0, 8.9 Hz), 7.88 (1H, d, J=3.3 Hz), 8.31 (1H, d, J=2.0 Hz).

EXAMPLE 3

1-(4-Fluorobenzyl)-2-(oxazol-2-yl)-5-methanesulfonyl-1H-pyrrolo[2,3-b]pyridine

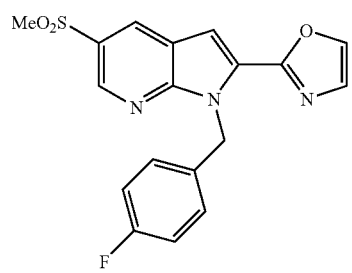

(1) Preparation of 1-benzenesulfonyl-2-(oxazol-2-yl)-5-methylthio-1H-pyrrolo[2,3-b]pyridine To a mixture of oxazole (7.6 g) and tetrahydrofuran (130 ml), 1.61M n-butyl lithium hexane solution (65 ml) was added at −78° C. under nitrogen atmosphere and the mixture was stirred for 40 minutes. To the reaction mixture was further added a mixture of triethyltin bromide (28.9 g) and tetrahydrofuran (50 ml) at −78° C. and the mixture was stirred as such at −78° C. for 1 hour, at 0° C. for 3 hours and at 15 to 30° C. for 2 hours. The reaction mixture was concentrated under reduced pressure and hexane (200 ml) was added to the residue. The precipitated insolubles were filtered off through Celite. The filtrate was concentrated under reduced pressure. The residue was subjected to distillation under reduced pressure to obtain 19.45 g of the fraction of 105 to 112° C. at 6 mmHg. To the resulting fraction was added dichloromethane and a mixture of bromine (3.7 ml) and dichloromethane (230 ml) was added thereto at 0° C. The mixture was stirred as such at 0° C. for 30 minutes and at 15 to 30° C. for 30 minutes. The reaction mixture was concentrated at normal pressure to obtain 37.71 g of the mixture containing 2-bromoxazole as a residue. 10 liters of acetylene gas was dissolved in diethyl ether (400 ml) under nitrogen atmosphere, 1.53 M n-butyl lithium hexane solution (100 ml) was added thereto at −78° C. and the mixture was stirred for 20 minutes. Subsequently, to the mixture was added a mixture of diethyl ether (80 ml) and the mixture containing 2-bromoxazole (37.71 g) at −78° C. and the mixture was stirred as such at −78° C. for 30 minutes and at −20° C. for 90 minutes. The insolubles were filtered off through Celite and the filtrate was concentrated under normal pressure. To the resulting residue were added dioxane (100 ml), 2-benzenesulfonylamino-3-iodo-5-methylthiopyridine (6 g), triethylamine (2 ml), cuprous iodide (0.1 g) and bis (triphenylphosphine) palladium chloride (0.35 g) and the mixture was stirred at 60° C. for 9 hours. To the reaction mixture were added dichloromethane and a saturated aqueous sodium hydrogencarbonate solution, and the mixture was filtered through Celite. The filtrate was extracted with dichloromethane, washed with a saturated aqueous NaCl solution, dried over sodium sulfate and concentrated under reduced pressure. The resulting residue was subjected to silica gel column chromatography (hexane:ethyl acetate=1:1) to obtain 0.70 g of the desired product.

$^1$H-NMR (CDCl$_3$) δ: 2.51 (3H, s), 6.94 (1H, s), 7.37 (1H, d, J=0.7 Hz), 7.46-7.62 (3H, m), 7.81 (1H, d, J=2.3 Hz), 7.91 (1H, d, J=0.7 Hz), 8.22-8.27 (2H, m), 8.49 (1H, d, J=2.3 Hz).

(2) Preparation of 1-benzenesulfonyl-2-(oxazol-2-yl)-5-methanesulfonyl-1H-pyrrolo[2,3-b]pyridine A mixture of 1-benzenesulfonyl-2-(oxazol-2-yl)-5-methylthio-1H-pyrrolo[2,3-b]pyridine (28 mg), magnesium monoperoxyphtalate hexahydrate (116 mg, 80% purity), dichloromethane (1.2 ml) and methanol (0.5 ml) was stirred at 0° C. for 30 minutes. To the reaction mixture was added a saturated aqueous sodium hydrogencarbonate solution, and the mixture was extracted with dichloromethane, washed with a saturated aqueous NaCl solution, dried over sodium sulfate and concentrated under reduced pressure. The resulting residue was subjected to silica gel column chromatography (hexane:ethyl acetate=1:3) to obtain 14 mg of the desired product.

$^1$H-NMR (CDCl$_3$) δ: 3.14 (3H, s), 7.13 (1H, s), 7.42 (1H, s), 7.54-7.70 (3H, m), 7.95 (1H, s), 8.35-8.40 (2H, m), 8.50. (H, d, J=2.3 Hz), 9.06 (1H, d, J=2.3 Hz).

(3) Preparation of 2-(oxazol-2-yl)-5-methanesulfonyl-1H-pyrrolo [2,3-b]pyridine

A mixture of 1-benzenesulfonyl-2-(oxazol-2-yl)-5-methanesulfonyl-1H-pyrrolo[2,3-b]pyridine (0.359 g), potassium hydroxide (0.34 g) and methanol (30 ml) was stirred at 15 to 30° C. for 30 minutes. To the reaction mixture was added water, the resulting mixture was extracted with dichloromethane, washed with a saturated aqueous NaCl solution, dried over sodium sulfate and concentrated under reduced pressure. The resulting residue was subjected to silica gel column chromatography (hexane:ethyl acetate 1:1) to obtain 0.19 g of the desired product.

$^1$H-NMR (DMSO-d$_6$) δ: 3.30 (3H, s), 7.31 (1H, d, J=2.0 Hz), 7.51 (1H, s), 8.35 (1H, s),8.63 (1H, d, J=2.3 Hz), 8.81.1 (1H, d, J=2.3 Hz), 13.30 (1H, s).

(4) Preparation of 1-(4-fluorobenzyl)-2-(oxazol-2-yl)-5-methanesulfonyl-1H-pyrrolo[2,3-b]pyridine A mixture of 2-(oxazol-2-yl)-5-methanesulfonyl-1H-pyrrolo[2,3-b]pyridine (0.19 g), 4-fluorobenzyl bromide (0.16 g), sodium hydride (32 mg, 60% purity), and dimethylformamide (10 ml) was stirred at 15 to 30° C. for 30 minutes. To the reaction mixture was added water, and the precipitated crystals were filtered off and dissolved in ethyl acetate. The solution was dried over sodium sulfate and concentrated under reduced pressure. The resulting residue (0.14 g) was recrystallized (ethyl acetate/hexane) to obtain 92 mg of the desired product.

mp: 200-201° C. MS: 371 (M$^+$) $^1$H-NMR (CDCl$_3$) δ: 3.16 (3H, s), 6.18 (2H, s), 6.91 (2H, t, J=8.6 Hz), 7.28-7.35 (3H, m), 7.77 (1H, d, J=0.6 Hz), 8.55 (1H, d, J=2.3 Hz), 8.95 (1H, d, J=2.3 Hz).

EXAMPLE 4

1-(4-Fluorobenzyl)-5-methanesulfonyl-2-([1,3,4] oxadiazol-2-yl)indole

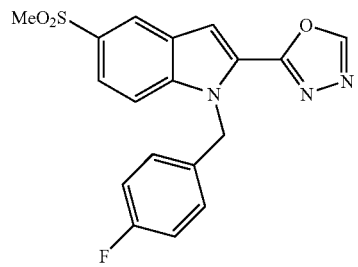

(1) Preparation of 1-benzenesulfonyl-5-methylthio-2-([1,3,4]oxadiazol-2-yl)-1H-indole To a solution of 1-benzenesulfonyl-5-methylthio-1H-indole-2-carboxylic acid methyl ester (370 mg) in ethanol (12 ml), hydrazine monohydrate (0.55 ml) was added at 15 to 30° C. and the mixture was heated under reflux for 13 hours. Further, to the mixture was added hydrazine monohydrate (0.55 ml) and the mixture was heated under reflux for 5 hours. The reaction solution was concentrated under reduced pressure. To the resulting residue was added water, and the insolubles were filtered off and washed with water and ether. To the filtered crude product was added formic acid (9 ml) and the mixture was heated under reflux for 1 hour. The reaction solution was concentrated under reduced pressure. To the resulting residue was added ethyl acetate and the insolubles were filtered off and washed with ethyl acetate. The filtrate was concentrated under reduced pressure to obtain 330 mg of the crude product of 1-benzenesulfonyl-5-methylthio-1H-indole-2-carboxylic acid-N'-formylhydrazide. A mixture solution of 509 mg of the crude product thus obtained and phosphorus oxychloride (15 ml) was stirred at 15 to 30° C. for 6 hours. The reaction solution was concentrated under reduced pressure. The resulting residue was separated using silica gel column chromatography (ethyl acetate:hexane 1:2) to obtain 265 mg of the desired product.

$^1$H-NMR (CDCl$_3$) δ: 2.51 (3H, s), 7.14 (1H, s), 7.3-7.6 (5H, m), 7.76-7.80 (2H, m), 8.08 (1H, d, J=8.57 Hz), 8.66 (1H, s);

MS (M+): 371.

(2) Preparation of 1-benzenesulfonyl-5-methanesulfonyl-2-([1,3,4]oxadiazol-2-yl)indole To a solution of the compound obtained in Example 4 (1) (265 mg) in tetrahydrofuran (7 ml), an aqueous solution (3.5 ml) of OXONE (registered trademark) (970 mg) was added dropwise and the mixture was stirred at 0° C. for 4 hours. To the reaction solution was added water, the mixture was extracted with ethyl acetate, dried over anhydrous magnesium sulfate, filtered and concentrated under reduced pressure. The resulting residue was separated using silica gel column chromatography (hexane:ethyl acetate=1:1) to obtain 262 mg of the desired product.

$^1$H-NMR (CDCl$_3$) δ: 3.09 (3H, s), 7.31 (1H, s), 7.4-8.0 (5H, m), 8.02 (1H, dd, J=1.65, 8.91 Hz), 8.26 (1H, d, J=1.32° Hz), 8.36 (1H, d, J=8.91 Hz), 8.69 (1H, s).

(3) Preparation of 1-(4-fluorobenzyl)-5-methanesulfonyl-2-([1,3,4]oxadiazol-2-yl)indole To a solution of the compound obtained in Example 4 (2) (262 mg) in methanol (10 ml), a 1N aqueous potassium hydroxide solution (2 ml) was added at 15 to 30° C. and the mixture was stirred at 15 to 30° C. for 1 hour. The reaction solution was concentrated under reduced pressure. To the resulting residue were added water and ethyl acetate and the insolubles were filtered off. The filtrate was extracted with ethyl acetate. The organic layer was washed with a saturated aqueous NaCl solution, dried over anhydrous sodium sulfate and filtered to obtain the crude product (200 mg) of 5-methanesulfonyl-2-([1,3,4]oxadiazol-2-yl)-1H-indole.

To a solution of the crude product (200 mg) of 5-methansulfonyl-2-([1,3,4]oxadiazol-2-yl)-1H-indole in N,N-dimethylformamide (8 ml), 60% sodium hydride (40 mg) was added at 0° C. under nitrogen atmosphere and the mixture was stirred for 5 minutes, followed by addition of 4-fluorobenzyl bromide (215 mg), and the mixture was stirred for 3 hours. To the reaction solution was then added water and the mixture was extracted with ethyl acetate. The organic layer was washed with a saturated aqueous NaCl solution, dried over anhydrous sodium sulfate, filtered and concentrated under reduced pressure. The resulting residue was separated using silica gel column chromatography (hexane:ethyl acetate=1:2) to obtain 67 mg of the desired product as a white powder.

$^1$H-NMR (CDCl$_3$) δ: 3.11 (3H, s), 6.08 (2H, s), 6.8-7.2 (4H, m), 7.47 (1H, s), 7.54 (1H, d, J=8.91 Hz), 7.85 (1H, dd, J=8.91, 1.65 Hz), 8.41 (1H, d, J=1.65 Hz), 8.50 (1H, s); MS (M+): 371.

EXAMPLE 5

5-Methanesulfonyl-2-(2-pyridyl)-1-(4-fluorobenzyl)-1H-pyrrolo [2,3-b]pyridine

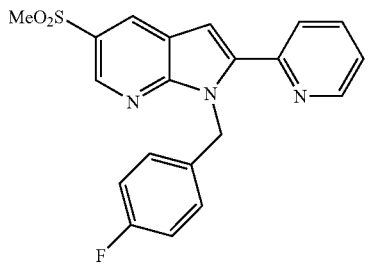

(1) Preparation of 2-benzenesulfonylamino-5-methylthio-3-iodo-pyridine

2-Amino-5-methylthio-3-iodo-pyridine (2.95 g) and benzenesulfonyl chloride (2.35 g) were dissolved in pyridine (11.1 ml) and the solution was stirred at 60° C. for 15 hours. The reaction solution was poured into water, extracted with chloroform, washed with a saturated aqueous NaCl solution, dried over anhydrous sodium sulfate, filtered and concentrated under reduced pressure. The resulting residue was separated using silica gel column chromatography (chloroform:methanol=50:1) to obtain 2.55 g of the desired product as a pale yellow crystal.

$^1$H-NMR (CDCl$_3$) δ: 2.41 (1H,s), 7.4-7.7 (4H, m), 7.91 (1H, s), 8.07 (1H, s), 8.13 (2H, d, J=7.3 Hz).

(2) Preparation of 1-benzenesulfonyl-5-methylthio-2-(2-pyridyl)-1H-pyrrolo[2,3-b]pyridine A suspension of the compound obtained in Example 5 (1) (100 mg), 2-ethynylpyridine (30.4 mg), bis(triphenylphosphine) palladium(II) dichloride (17.3 mg) and cuprous iodide (4.7 mg) in triethylamine (2.5 ml) was stirred in a sealed tube at 100° C. for 1 hour. After completion of the reaction, the reaction suspension was poured into water, extracted with methylene chloride, washed with a saturated aqueous NaCl solution, dried over anhydrous sodium sulfate, filtered and concentrated under reduced pressure. The resulting residue was separated using silica gel preparative thin-layer chromatography (hexane:ethyl acetate=1:1) to obtain 71.9 mg of the desired product as a colorless oil.

$^1$H-NMR (CDCl$_3$) δ: 2.50(3H, s), 6.69 (1H, s), 7.3-7.7 (4H, m), 7.68 (1H, d, J=7.8 Hz), 7.76 (1H, d, J=1.9 Hz), 7.83 (1H, m), 8.16 (2H, d, J=7.3 Hz), 8.44 (1H, d, J=1.9 Hz), 8.72 (1H, d, J=4.3 Hz).

(3) Preparation of 1-benzenesulfonyl-5-methanesulfonyl-2-(2-pyridyl)-1H-pyrrolo[2,3-b]pyridine To a solution of the compound obtained in Example 5 (2) (1.00 g) in chloroform (7 ml), m-chloroperbenzoic acid (1.36 g) was added at 0° C. and the mixture was stirred at the same temperature for 1 hour. After completion of the reaction, the reaction solution was poured into a saturated aqueous sodium hydrogencarbonate solution, extracted with chloroform, washed with a saturated aqueous NaCl solution, dried over anhydrous sodium sulfate, filtered and concentrated under reduced pressure. The resulting residue was separated using silica gel column chromatography (chloroform methanol 50:1) to obtain 1.00 g of the desired product as a white crystal.

$^1$H-NMR (CDCl$_3$) δ: 3.13 (3H, s), 6.82 (1H, s), 7.3-7.8 (5H, m), 7.87 (1H, m), 8.34 (2H, d, J=7.3 Hz), 8.42 (1H, d, J=1.9 Hz), 8.76 (1H, d, J=4.6 Hz), 9.01 (1H, d, J=1.9 Hz).

(4) Preparation of 5-methanesulfonyl-2-(2-pyridyl)-1H-pyrrolo[2,3-b]pyridine To a solution of the compound obtained in Example 5 (3) (3.8 mg) in methanol (0.5 ml), a 1N aqueous potassium hydroxide solution (2 ml) was added and the mixture was heated under reflux for 2 hours. After completion of the reaction, the reaction solution was poured into water, extracted with chloroform, washed with a saturated aqueous NaCl solution, dried over anhydrous sodium sulfate, filtered and concentrated under reduced pressure. The residue was poured into a phosphorate buffer (pH 7.0), extracted with dichloromethane, washed with a saturated aqueous NaCl solution, dried over anhydrous sodium sulfate, filtered and concentrated under reduced pressure. The resulting residue was separated using silica gel preparative thin-layer chromatography (chloroform:methanol 50:1) to obtain 2.4 mg of the desired product as a white powder.

$^1$H-NMR (CDCl$_3$) δ: 3.16 (3H, s), 7.10 (1H, s), 7.2-7.4 (1H, m), 7.7-8.9 (2H, m), 8.52 (1H, d, J=1.8 Hz), 8.71 (1H, d, J=4.6 Hz), 8.97 (1H, d, J=1.8 Hz), 0.95 (1H, bs).

(5) Preparation of 5-methanesulfonyl-2-(2-pyridyl)-1-(4-fluorobenzyl)-1H-pyrrolo[2,3-b]pyridine To a solution of the compound obtained in Example 5 (4) (2.3 mg) in N,N-dimethylformamide (0.5 ml), 60% sodium hydride. (0.5 mg) was added at 0° C. and the mixture was stirred at the same temperature for 15 minutes. p-Fluorobenzyl bromide. (2.4 mg) was then added thereto at 0° C. and the mixture was stirred at 15 to 30° C. for 1 hour. The reaction solution was poured into a saturated aqueous sodium hydrogencarbonate solution, extracted with toluene, dried over anhydrous sodium sulfate, filtered and concentrated under reduced pressure. The resulting residue was separated using silica gel preparative thin-layer chromatography (chloroform:methanol=100:1) to obtain 1.7 mg of the desired product as a white powder.

$^1$H-NMR (CDCl$_3$) δ: 3.16 (3H, s), 6.17 (2H, s), 6.81 (2H, m), 6.9-7.1 (3H, m), 7.2-7.4 (1H, m), 7.5-7.9 (2H, m), 8.51 (1H, d, J=2.0 Hz), 8.72 (1H, d, J=3.8 Hz), 8.91 (1H, d, J=2.0 Hz);

Fab-Ms: 382 (M+1).

EXAMPLE 6

1-(4-Fluorobenzyl)-5-methanesulfonyl-2-(2-pyrimidinyl)-1H-pyrrolo[2,3-b]pyridine

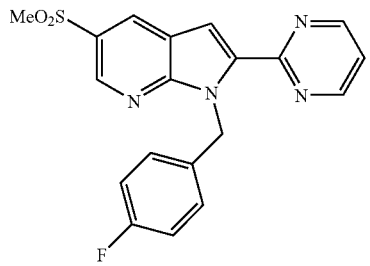

(1) Preparation of 1-benzenesulfonyl-5-methylthio-2-(2-pyrimidinyl)-1H-pyrrolo[2,3-b]pyridine A suspension of 2-benzenesulfonylamino-5-methylthio-3-iodo-pyridine (1.53 g), 2-ethynylpyrimidine (768 mg), bistriphenylphosphine palladium dichloride (259 mg) and cuprous iodide (70.3 mg) in triethylamine (37 ml) was stirred in a sealed tube at 100° C. for 1.5 hours. After cooling, the reaction solution was poured into water, extracted with chloroform, dried over anhydrous sodium sulfate, filtered and concentrated under reduced pressure. The resulting residue was separated using silica gel column chromatography (hexane:ethyl acetate=1:1) to obtain 1.21 g of the desired product as a white crystal.

$^1$H-NMR (CDCl$_3$) δ: 2.52 (3H, s), 6.95 (1H, s); 7.33 (1H, t, J=4.8 Hz), 7.5-7.7 (3H, m), 7.83 (1H, d, J=2.6 Hz), 8.39 (2H, d, J=6.9 Hz), 8.48 (1H, d, J=2.6), 8.87 (2H, d, J=4.8 Hz).

(2) Preparation of 1-benzenesulfonyl-5-methanesulfonyl-2-(2-pyrimidinyl)-1H-pyrrolo[2,3-b]pyridine To a solution of the compound obtained in Example 6 (1) (1.10 g) in chloroform (30 ml), m-chloroperbenzoic acid (1.56 g) was added at 0° C. and the mixture was stirred at 0° C. for 1.5 hours. The reaction solution was then poured into a saturated aqueous sodium hydrogencarbonate solution extracted with chloroform, dried over anhydrous sodium sulfate, filtered and concentrated under reduced pressure. The resulting residue was separated using silica gel column chromatography (chloroform methanol 20:1) to obtain 1.10 g of the desired product as a white powder.

$^1$H-NMR (CDCl$_3$) δ: 3.14 (3H, s), 7.11 (1H, s), 7.40 (1H, t, J=4.9 Hz), 7.5-7.8 (3H, m), 8.4-8.6 (3H, m), 8.92 (2H, d, J=4.9 Hz), 9.05 (1H, d, J=1.1 Hz).

(3) Preparation of 5-methanesulfonyl-2-(2-pyrimidinyl)-1H-pyrrolo[2,3-b]pyridine To a suspension of the compound obtained in Example 6 (2) (1.10 g) in methanol (24 ml), a 1N aqueous potassium hydroxide solution (4.8 ml) was added and the mixture was stirred at 15 to 30° C. for 1 hour. The mixture was further heated under reflux for 15 minutes. After completion of the reaction, the reaction solution was poured into water, extracted with chloroform, washed with a saturated aqueous NaCl solution, dried over anhydrous sodium sulfate, filtered and concentrated under reduced pressure. The resulting residue was washed with methanol/water and filtered off. Further, the unnecessary substances in the aqueous layer during extraction were filtered off, and they were combined and heated to dryness to obtain 417 mg of the desired product as a white powder.

$^1$H-NMR (DMSO-d$_6$) δ: 3.31 (3H, s), 7.50 (1H, t, J=4.9 Hz), 7.54 (1H, s), 8.65 (1H, d, J=2.2 Hz), 8.81 (1H, d, J=2.2 Hz), 8.95 (2H, d, J=4.9 Hz), 13.0 (1H, brs).

(4) Preparation of 1-(4-fluorobenzyl)-2-(2-pyrimidinyl)-5-methanesulfonyl-1H-pyrrolo[2,3-b]pyridine To a solution of the compound obtained in Example 6 (3) (3.0 mg) in N,N-dimethylformamide (0.5 ml), 60% sodium hydride (0.7 mg) was added at 0° C. under nitrogen atmosphere and the mixture was stirred at the same temperature for 15 minutes. 4-Fluorobenzyl bromide (3.1 mg) was then added thereto at 0° C. and the mixture was stirred at 15 to 30° C. for 1 hour. After completion of the reaction, the reaction solution was poured into a saturated aqueous sodium hydrogencarbonate solution and extracted with toluene. The organic layer was washed with a saturated aqueous NaCl solution, dried over anhydrous sodium sulfate, filtered and concentrated under reduced pressure. The resulting residue was separated using silica gel preparative thin-layer chromatography (methanol:chloroform=1:20) to obtain 2.4 mg of the desired product as a white crystal.

$^3$H-NMR (CDCl$_3$) δ: 3.17 (3H, s), 6.33 (2H, s), 6.86 (2H, t, J=8.6 Hz), 7.0-7.2 (2H, m), 7.22 (1H, t, J=5.4 Hz), 7.67 (1H, s), 8.59 (1H, d, J=2.1 Hz), 8.79 (2H, d, J=5.4 Hz), 8.95 (1H, d, J=2.1 Hz).

EXAMPLE 7

1-Cyclohexylmethyl-5-methanesulfonyl-2-(2-pyrimidinyl)-1H-pyrrolo[2,3-b]pyridine

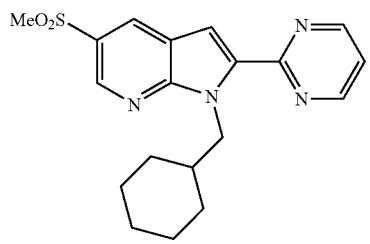

To a suspension of 5-methanesulfonyl-2-(2-pyrimidinyl)-1H-pyrrolo[2,3-b]pyridine (150 mg) in N,N-dimethylformamide (5.5 ml), 60% sodium hydride (32.8 mg) was added at 0° C. under nitrogen atmosphere and the mixture was stirred at the same temperature for 30 minutes. Subsequently, to the mixture was added cyclohexylmethyl bromide (154 mg) at 0° C. and the mixture was stirred at 60° C. for 2 hours, followed by addition of cyclohexylmethyl bromide (77 mg) and stirring of the mixture at the same temperature for 1 hour. Further, to the mixture was added cyclohexylmethyl bromide (77 mg) and the mixture was stirred at 60° C. for 15 hours. Subsequently, the reaction solution was poured into a saturated aqueous sodium hydrogencarbonate solution and extracted with chloroform. The organic layer was washed with a saturated aqueous NaCl solution, dried over anhydrous sodium sulfate, filtered and concentrated under reduced pressure. The resulting residue was separated using silica gel preparative thin-layer chromatography (methanol:chloroform=1:20) and further recrystallized, (chloroform/hexane) to obtain 109 mg of the desired product as a white needle-like crystal.

$^1$H-NMR (CDCl$_3$) δ: 0.8-1.2 (4H, m), 1.2-1.9 (7H, m), 3.17 (3H, s), 4.97 (2H, d, J=7.3), 7.1-7.4 (1H, m), 7.58 (1H, s), 8.54 (1H, d, J=2.4 Hz), 8.85 (2H, d, J=4.5 Hz), 8.91 (1H, d, J=2.4 Hz).

EXAMPLE 8

2-(2-Furanyl)-1-(4-fluorobenzyl)-5-methanesulfonyl-1H-indole

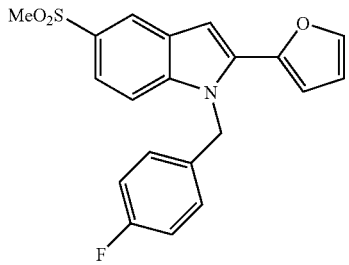

(1) Preparation of 2,2-dimethyl-N-(2-iodo-4-methylthiophenyl)propionamide

To a solution of 4-methylthioaniline (25 g) in pyridine (250 ml), pivaloyl chloride (26.2 ml) was added at 15 to 30° C. and the mixture was stirred for 15 hours. The reaction solution was then concentrated under reduced pressure, poured into a saturated aqueous sodium hydrogencarbonate solution, extracted with ethyl acetate, dried over anhydrous magnesium sulfate, filtered and concentrated under reduced pressure. A solution of the resulting residue (20 g) in tetrahydrofuran, (400 ml) was added t-butyl lithium (175 ml, 1.64 M) under nitrogen atmosphere at −78° C. and the mixture was stirred at −78° C. for 15 minutes and then heated to 0° C. The reaction mixture was cooled again to −78° C., and to the mixture was added a solution of iodine (27.3 g) in tetrahydrofuran (100 ml). After the mixture was stirred for 30 minutes, it was heated to 15 to 30° C. The reaction solution was then poured into a saturated aqueous ammonium chloride solution, extracted with ethyl acetate, dried over anhydrous magnesium sulfate, filtered and concentrated under reduced pressure. The resulting residue was separated using silica gel column chromatography (hexane:ethyl acetate=9:1) to obtain 19 g of the desired product as a white powder.

$^1$H-NMR (CDCl$_3$) δ: 1.36 (9H, s), 2.46 (3H, s), 7.25 (1H, dd, J=8.9, 2.0 Hz), 7.66 (1H, d, J=2.0 Hz), 7.72 (1H, brs), 8.18 (1H, d, J=8.9 Hz).

(2) Preparation of 2,2-dimethyl-N-(2-iodo-4-methanesulfonylphenyl)propionamide

To a solution of 2,2-dimethyl-N-(2-iodo-4-methylthiophenyl)propionamide in a mixture of tetrahydrofuran/water mixture (2:1, 210 ml), OXONE (registered trademark) (22.0 mg) was added and the mixture was stirred at 15 to 30° C. for 2 hours. After completion of the reaction, the reaction solution was poured into a saturated aqueous sodium hydrogencarbonate solution, extracted with ethyl acetate, washed with a saturated aqueous NaCl solution, dried over anhydrous sodium sulfate, filtered and concentrated under reduced pressure. The resulting residue was recrystallized (ethyl acetate/n-hexane) to obtain 5.22 g of the desired product as a white crystal.

$^1$H-NMR (CDCl$_3$) δ: 1.39 (9H, s), 3.05 (3H, s), 7.90 (1H, dd, J=2.1 Hz; 8.6 Hz), 8.08 (1H, brs), 8.33 (1H, d, J=2.1 Hz), 8.59 (1H, d, J=8.6 Hz).

(3) Preparation of 2-iodo-methanesulfonylaniline

To a solution of the compound obtained in Example, 8 (2) (100 mg) in methanol (2.6 ml), a 1N aqueous potassium hydroxide solution (0.55 ml) was added and the mixture was heated under reflux for 1 hour. The reaction solution was then concentrated under reduced pressure. The resulting residue was dissolved in chloroform, washed with water and a saturated aqueous NaCl solution successively, dried over anhydrous sodium sulfate, filtered, concentrated under reduced pressure and dried under reduced pressure to obtain 74.6 mg of the desired product as a white crystal.

$^1$H-NMR (CDCl$_3$) δ: 3.02 (3H, s), 4.68 (2H, brs), 6.77 (1H, d, J=8.6 Hz), 7.67 (1H, dd, J=2.0 Hz, 8.6 Hz), 8.18 (1H, d, J=2.0 Hz).

(4) Preparation of 1-bisbenzenesulfonylamino-2-iodo-4-methanesulfonylbenzene

To a solution of the compound obtained in Example 8 (3) (2.20 g) in pyridine (7.4 ml), benzenesulfonyl chloride (1.57 g) was added and the mixture was stirred at 15 to 30° C. for 1 hour and at 60° C. for 1 hour. Further, to the mixture was added benzenesulfonyl chloride (1.57 g) and the mixture was stirred at 60° C. for 15 hours, and: then poured into a saturated aqueous ammonium chloride solution. The precipitates were filtered off, washed with water and ether successively and dried under reduced pressure to obtain 4.22 g of the desired products as a white crystal.

$^1$H-NMR (CDCl$_3$) δ: 3.13 (3H, s), 7.1-7.4 (4H, t, J=7.7 Hz), 7.74 (2H, t, J=7.6 Hz), 7.90 (1H, d, J=8.1 Hz), 8.00 (4H, d, J=8.1 Hz), 8.43 (1H, s).

(5) Preparation of 1-benzenesulfonylamino-2-iodo-4-methanesulfonylbenzene

To a suspension of the compound obtained in Example 8 (4) (4.90 g) in 1,4-dioxane (85 ml), a 1N aqueous potassium hydroxide solution (21.2 ml) was added and the mixture was stirred at 100° C. for 1 hour. After completion of the reaction, the reaction solution was concentrated under reduced pressure, poured into a saturated aqueous NaCl solution, extracted with tetrahydrofuran, dried over anhydrous sodium sulfate, filtered and concentrated under reduced pressure. The resulting residue was separated using silica gel column chromatography (chloroform methanol=10:1) to obtain 3.47 g of the desired product in a colorless amorphous form.

$^1$H-NMR (CDCl$_3$) δ: 3.03 (3H, s), 7.51 (2H, t, J=7.6 Hz), 7.22 (1H, brs), 7.62 (1H, t, J=7.0 Hz), 7.76 (1H, d, J=8.6 Hz), 7.8-8.0 (3H, m), 8.23 (1H, d, J=1.9 Hz).

(6) Preparation of 2-(2-furanyl)-5-methanesulfonylindole

To a suspension of the compound obtained in Example 8 (5) (2.00 g), bistriphenylphosphine palladium dichloride (321 mg), cuprous iodide (87.0 mg) and triethylamine (1.38 g) in N,N-dimethylformamide (46 ml), a solution of 2-ethynylfuran (842 mg) in N,N-dimethylformamide (46 ml) was slowly added dropwise under nitrogen atmosphere and the mixture was stirred at 60° C. for 3 hours. The reaction solution was then poured into water, extracted with chloroform, washed with a saturated aqueous NaCl solution, dried over anhydrous sodium sulfate, filtered and concentrated under reduced pressure. The resulting residue was separated using silica gel column chromatography (methanol:chloroform=1:100). To a solution of the obtained colorless amorphous compound (1.10 g) in methanol (28 ml) was added a 1N aqueous potassium hydroxide solution (5.52 ml) and the mixture was stirred at 60° C. for 1 hour. After completion of the reaction, the reaction solution was concentrated under reduced pressure. The resulting residue was poured into water, extracted with chloroform, washed with a saturated aqueous NaCl solution, dried over anhydrous sodium sulfate, filtered and concentrated under reduced pressure. The resulting residue was separated using silica gel preparative thin-layer chromatography (methanol chloroform=1:20) to obtain 350 mg of the desired product as a brown crystal.

$^1$H-NMR (CDCl$_3$) δ: 3.09 (3H, s), 6.5-6.6 (1H, m), 6.75 (1H, d, J=3.2 Hz), 6.85. (1H, s), 7.4-7.6 (2H, m), 7.72 (1h, dd, J=1.8 Hz, 8.5 Hz), 8.23 (1H, s), 8.85 (1H, brs).

(7) Preparation of 2-(2-furanyl)-1-(4-fluorobenzyl)-5-methanesulfonylindole

To a solution of the compound obtained in Example 8 (6) (150 mg) in N,N-dimethylformamide (6 ml), 60% sodium hydride (34.4 mg) was added at 0° C. under-nitrogen atmosphere, and the mixture was stirred for 15 minutes. To the mixture was added 4-fluorobenzyl bromide (160 mg), followed by stirring for 2 hours. After completion of the reaction, the reaction solution was poured into a saturated aqueous ammonium chloride solution, extracted with toluene, washed with a saturated aqueous NaCl solution, dried over anhydrous sodium sulfate, filtered and concentrated under reduced pressure. The resulting residue was separated using silica gel column chromatography (methanol:chloroform=1:100) and silica gel preparative thin-layer chromatography (methanol:chloroform=1:100) to obtain 130 mg of the desired product as a pale brown oil.

$^1$H-NMR (CDCl$_3$) δ: 3.09 (3H, s), 5.58 (2H, s), 6.4-6.6 (1H, m), 6.54 (H, d, J=3.5 Hz), 6.9-7.1 (5H, m), 7.36 (1H, d, J=8.8 Hz), 7.53 (1H, d, J=1.4 Hz), 7.71 (1H, dd, J=1.8 Hz, 8.8 Hzt), 8.28 (1H, d, J=1.8 Hz).

EXAMPLE 9

1-Cyclohexylmethyl-2-(2-furanyl)-5-methanesulfonylindole

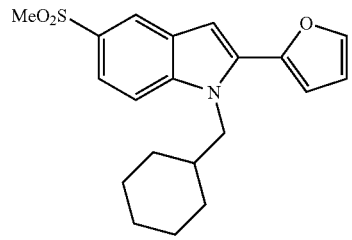

To a solution of 2-(2-furanyl)-5-methanesulfonylindole (150 mg) in N,N-dimethylformamide (6 ml), 60% sodium hydride (34.4 mg) was added at 0° C. under nitrogen atmosphere and the mixture was stirred for 15 minutes. Subsequently, cyclohexylmethyl bromide (205 mg) was added to the mixture, followed by stirring for 3 hours. After completion of the reaction, the reaction solution was poured into a saturated aqueous ammonium chloride solution, extracted with toluene, washed with a saturated aqueous NaCl solution, dried over anhydrous sodium sulfate, filtered and concentrated under reduced pressure. The resulting residue was separated using silica gel column chromatography (methanol:chloroform 1:100) to obtain 164 mg of the desired product as a pale yellow oil.

$^1$H-NMR (CDCl$_3$) δ: 0.8-1.3 (4H, m), 1.4-2.0 (7H, m), 3.10 (3H, s), 4.24 (2H, d, J=7.3 Hz), 6.5-6.7. (1H, m), 6.67 (1H, d, J=3.5 Hz), 6.89 (1H, s), 7.47 (1H, d, J=8.6 Hz), 7.57 (1H, d, J=1.4 Hz), 7.72 (1H, dd, J=1.8 Hz, 8.6 Hz), 8.23 (1H, d, J=1.5 Hz).

EXAMPLE 10

2-(2-Furanyl)-5-methanesulfonyl-1-(2-pyridylmethyl)-1H-pyrrolo[2,3-b]pyridine

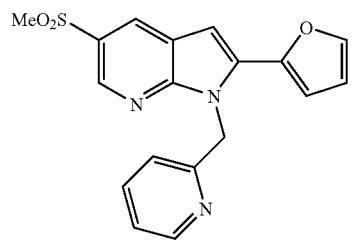

To a solution of 2-(2-furanyl)-5-methanesulfonyl-1H-pyrrolo[2,3-b]pyridine (140 mg) in N,N-dimethylformamide (5 ml), 60% sodium hydride (53.6 mg) was added at 0° C. under nitrogen atmosphere and the mixture was stirred for 30 minutes. Subsequently, 2-picolyl chloride hydrochloride (105 mg) was added thereto, followed by stirring at 15 to 30° C. for 15 hours. The reaction solution was then poured into a saturated aqueous sodium hydrogencarbonate solution, extracted with toluene, washed with a saturated aqueous NaCl solution, dried over anhydrous magnesium sulfate, filtered and concentrated under reduced pressure. The resulting residue was separated using silica gel column chromatography (ethyl acetate:n-hexane 1:1). The resulting crystal was further recrystallized from methanol to obtain 69.3 mg (37%) of the desired product as a pale yellow needle-like crystal.

$^1$H-NMR (CDCl$_3$) δ: 3.16 (3H, s), 5.96 (2H, s), 6.4-6.6 (1H, m), 6.70 (1H, d, J=3.8 Hz), 6.77 (1H, d, J=8.1 Hz), 6.99 (1H, s), 7.16 (1H, t, J=7.6 Hz), 7.50 (H, 6), 7.54 (1H, t, J=7.3 Hz), 8.49 (1H, d, J=2.0 Hz), 8.59 (1H, d, J=4.9 Hz), 8.84 (1H, d, J=2.0 Hz).

EXAMPLE 11 b 1-(4-Fluorobenzyl)-5-methanesulfonyl-2-(5-methylfuran-2-yl)-1H-pyrrolo[2,3-b]pyridine

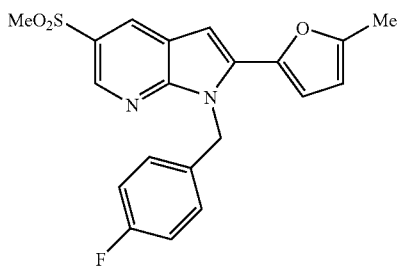

(1) Preparation of 1-benzenesulfonyl-2-(5-methylfuran-2-yl)-5-methylthio-1H-pyrrolo[2,3-b]pyridine To a solution of 2-benzenesulfonylamino-5-methylthio-3-iodopyridine (203 mg) in 1,4-dioxane (5 ml), 2-ethynyl-5-methylfuran (160 mg), bistriphenylphosphine palladium dichloride (18 mg), cuprous iodide (10 mg) and triethylamine (75 mg) were added successively and the mixture was stirred in a sealed tube at 60° C. for 1 hour. After cooling, the reaction solution was poured into water, extracted with dichloromethane, dried over anhydrous magnesium sulfate, filtered and-concentrated under reduced pressure. The resulting residue was separated using silica gel preparative thin-layer chromatography (hexane:ethyl acetate=5:1) to obtain 169 mg of the desired products as a brown oil.

$^1$H-NMR (CDCl$_3$) δ: 2.41 (3H, s), 2.50 (3H, s), 6.15 (1H, d, J=2.3 Hz), 6.61° (1H, s), 6.69 (1H, d, J=3.3 Hz), 7.41-7.64 (3H, m), 7.72 (1H, d, J=2.0 Hz), 8.10-8.19 (2H, m), 8.42 (1H, d, J=2.3 Hz).

(2) Preparation of 1-benzenesulfonyl-5-methanesulfonyl-2-(5-methylfuran-2-yl)-1H-pyrrolo[2,3-b]pyridine To a solution of the compound obtained in Example 11' (1) (169 mg), in a mixture of dichloromethane/methanol (5:1, 16 ml), magnesium monoperoxyphthalate (679 mg, 80% purity) was added at 0° C. and the mixture was stirred at the same temperature for 30 minutes and at 15 to 30° C. for 1 hour. The reaction solution was then poured into a saturated aqueous sodium hydrogencarbonate solution, extracted with chloroform, dried over anhydrous magnesium sulfate, filtered and concentrated under reduced pressure. The resulting residue was separated using silica gel preparative thin-layer chromatography (hexane chloroform:acetone=6:3:1) to obtain 121 mg of the desired product as a yellow oil.

$^1$H-NMR (CDCl$_3$) δ: 2.44 (3H, s), 3.13 (3H, s), 6.18(1H, d, J=3.0 Hz), 6.76 (1H, d, J=3.3 Hz), 6.79 (1H, s), 7.50-7.66 (3H, m), 8.20-8.28 (2H, m), 8.37 (1H, d, J=2.0 Hz), 8.97 (1H, d, J=2.0 Hz).

(3) Preparation of 5-methanesulfonyl-2-(5-methylfuran-2-yl)-1H-pyrrolo[2,3-b]pyridine To a mixture solution of the compound obtained in Example 11 (2) (421 mg) in methanol (60 ml), a 1N aqueous potassium hydroxide solution (3 ml) was added and the mixture was stirred at 60° C. for 1 hour. The reaction solution was then concentrated under reduced pressure. The residue was washed with water and ether and dried to obtain 252 mg of the desired product as a yellow powder.

$^1$H-NMR (DMSO-d$_6$) δ: 2.39 (3H, s), 3.28 (3H, s), 6.31 (1H, d, J=2.6 Hz), 6.82 (1H, s), 7.01 (1H, d, J=3.0 Hz), 8.43 (1H, d, J=2.0 Hz) 8.66 (1H, d, J=2.0 Hz), 12.75 (1H, brs).

(4) Preparation of 1-(4-fluorobenzyl)-5-methanesulfonyl-2-(5-methylfuran-2-yl)-1H-pyrrolo[2,3-b]pyridine To a solution of the compound obtained in Example 11' (3) (20,mg) in N,N-dimethylformamide (2 ml), 60% sodium hydride (4.4 mg) was added at 0° C. under nitrogen atmosphere and the mixture was stirred for 30 minutes, followed by addition of 4-fluorobenzyl bromide (2.6 mg), and the reaction mixture was stirred for further 30 minutes. The reaction solution was then poured into a saturated aqueous sodium hydrogencarbonate solution and extracted with toluene. The organic layer was washed with water and a saturated aqueous NaCl solution, dried over anhydrous magnesium sulfate, filtered and concentrated under reduced pressure. The resulting residue was separated using silica gel preparative thin-layer chromatography (hexane:ethyl acetate 1:1) to obtain 18 mg of the desired product as a yellow powder.

$^1$H-NMR (CDCl$_3$) δ: 2.38 (3H, s), 3.15 (3H, s), 5.79 (2H, s), 6.08 (1H, d, J=3.3 Hz), 6.46 (1H, d, J=3.3 Hz), 6.86 (1H, s), 6.92-7.18 (4H, m), 8.43 (1H, d, J=2.0 Hz), 8.82 (1H, d, J=2.3 Hz).

EXAMPLE 12

2-(2-Furanyl)-1-cyclohexylmethyl-5-methanesulfonyl-1H-pyrrolo [2,3-b]pyridine

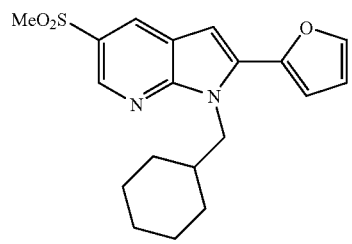

To a solution of 2-(2-furanyl)-5-methanesulfonyl-1H-pyrrolo [2,3-b]pyridine (5.5 mg) in N,N-dimethylformamide (0.5 ml), 60% sodium hydride (1.3 mg) was added at 0° C. under nitrogen atmosphere and the mixture was-stirred for 30 minutes, followed by addition of bromomethylcyclohexane (7.4 mg), and the reaction mixture was stirred at 15 to 30° C. for 5 hours and at 60° C. for 1 hour. The reaction solution was then poured into a saturated aqueous ammonium chloride solution, and extracted with ethyl acetate. The organic layer was washed with water and a saturated aqueous NaCl solution, dried over anhydrous magnesium sulfate, filtered and concentrated under reduced pressure. The resulting residue was separated using silica gel preparative thin-layer chromatography (hexane:ethyl acetate=1:1) to obtain 4.5 mg of the desired product as a white powder.

$^1$H-NMR (CDCl$_3$) δ: 1.00-1.20 (4H, m), 1.42-1.51 (2H, m), 1.57-1.75 (4H, m), 1.78-1.93 (1H, m), 3.15 (3H, s), 4.48 (2H, d, J=7.4 Hz), 6.58-6.60 (1H, m), 6.76 (1H, d, J=3.6 Hz), 6.86 (1H, s), 7.60 (1H, d, J=1.6 Hz), 8.41 (1H, d, J=2.2 Hz), 8.82 (1H, d, J=2.2 Hz).

EXAMPLE 13

2-(2-Tetrahydrofuranyl)-1-(4-fluorobenzyl)-5-methanesulfonyl-indole

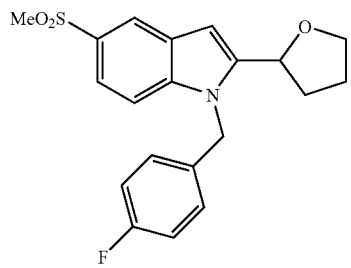

(1) Preparation of 2-(2-tetrahydrofuranyl)-5-methanesulfonyl-1-benzenesulfonylindole To a solution of 1-benzenesulfonylamino-2-iodo-4-methanesulfonylbenzene (256 mg) in 1,4-dioxane (6 ml), 2-ethynyltetrahydrofuran (169 mg), bistriphenylphosphine palladium dichloride (21 mg), cuprous iodide (11 mg) and triethylamine (89 mg) were added successively and the mixture was stirred in a sealed tube at 60° C. for 3 hours. After cooling the reaction solution was poured into water, extracted with dichloromethane, dried over anhydrous magnesium sulfate, filtered and concentrated under reduced pressure. The resulting residue was separated using silica gel preparative thin-layer chromatography (hexane:ethyl acetate=1:1) to obtain 218 mg of the desired product in a white amorphous form.

$^1$H-NMR (CDCl$_3$) δ: 1.90-2.20 (3H, m), 2.50-2.65 (1H, m), 3.06 (3H, s), 3.90-4.00 (1H, m), 4.08-4.18 (1H, m), 5.58 (1H, m), 6.78 (1H, s), 7.42-7.57 (3H, m), 7.78-7.83 (3H, m), 8.07 (1H, d, J=1.3 Hz), 8.28 (1H, d, 8.9 Hz).

(2) Preparation of 2-(2-tetrahydrofuranyl)-5-methanesulfonyl-1H-indole

To a solution of the compound obtained in Example 13 (1) (210 mg) in a mixture of tetrahydrofuran/methanol (2:1, 15 ml), a 1N aqueous potassium hydroxide solution (1.6 ml) was added and the mixture was stirred at 100° C. for 2 hours. The reaction solution was then poured into water, extracted with dichloromethane, dried over anhydrous magnesium sulfate, filtered and concentrated under reduced pressure. The resulting residue was separated using silica gel preparative thin-layer chromatography (hexane ethyl acetate=1:1) to obtain 113 mg of the desired product as a white powder.

$^1$H-NMR (CDCl$_3$) δ: 2.00-2.15 (3H, m), 2.32-2.48 (1H, m), 3.07 (3H, s), 3.90-4.16 (2H, m), 5.11-5.20 (1H, m), 6.45 (1H, s), 7.45 (1H, d, J=8.6 Hz), 7.68 (1H, d, J=8.3 Hz), 8.19 (1H, s), 8.92 (1H, brs).

(3) Preparation of 2-(2-tetrahydrofuranyl)-5-methanesulfonyl-1-(4-fluorobenzyl)-1H-indole To a solution of the compound obtained in Example 13: (2) (113 mg) in N,N-dimethylformamide (5 ml), 60% sodium hydride (25.6 mg) was added under nitrogen atmosphere at 0° C. and the mixture was stirred for 30 minutes, followed by addition of 4-fluorobenzyl bromide (121 mg), and the mixture was stirred for 1 hour. The reaction solution was then poured into a saturated aqueous ammonium chloride solution and extracted with ethyl acetate. The organic layer was washed with water and a saturated aqueous NaCl solution, dried over anhydrous magnesium sulfate, filtered and concentrated under reduced pressure. The resulting residue was separated using silica gel preparative thin-layer chromatography (hexane:ethyl acetate-=1:1) to obtain 139 mg of the desired product as a white powder.

$^1$H-NMR (CDCl$_3$) δ: 1.35-1.95 (4H, m), 3.06 (3H, s), 3.82-4.02 (2H, m), 4.97 (1H, t, J=6.6 Hz), 5.43-5.60 (2H, m), 6.66 (1H, s), 6.95-6.98 (4H, m), 7.29 (1H, d, J=8.6 Hz), 7.66 (1H, dd, J=8.6, 1.7 Hz), 8.24 (1H, d, J=1.3 Hz).

EXAMPLE 14

2-(5,6-Dihydro-2H-4-pyranyl)-1-(4-fluorobenzyl)-5-methanesulfonyl-indole

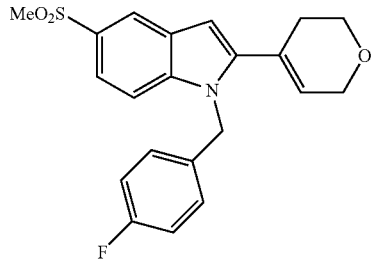

(1) Preparation of 2-(4-hydroxytetrahydro-4H-4-pyranyl)-5-methylthio-1-benzenesulfonylindole To a solution of 5-methylthiol-1-benzenesulfonylindole (200 mg) in tetrahydrofuran. (5 ml), n-butyl lithium (0.49 ml, 1.61 M) was added at −78° C. under nitrogen atmosphere and the mixture was stirred at −78° C. for 30 minutes, followed by addition of hexamethylphosphoric triamide (0.23 ml), and the mixture was stirred for 15 minutes. Subsequently, tetrahydro-4H-pyran-4-one (0.12 ml) was added thereto and the mixture was stirred at −78° C. for 15 minutes and heated to 15 to 30° C. The reaction solution was then poured into a saturated aqueous ammonium chloride solution, extracted with dichloromethane, dried over anhydrous magnesium sulfate, filtered and concentrated under reduced pressure. The resulting residue was separated using silica gel preparative thin-layer chromatography. (hexane:ethyl acetate=1:1) and (methanol:chloroform=1:20) to obtain 39 mg of the desired product as a colorless oil.

$^1$H-NMR (CDCl$_3$) δ: 2.10-2.22 (2H, m), 2.37-2.55 (5H, m), 3.79-4.10 (4H, m), 4.80 (1H, s), 6.66 (1H, s), 7.16. (1H dd, J=8.6, 1.7 Hz), 70.30-7.49 (4H, m); 7.77-7.89. (3H, m).

(2) Preparation of 2-(5,6-dihydro-2H-4-pyranyl)-1-benzenesulfonyl-5-methylthioindole To a solution of the compound obtained in Example 14 (1) (39 mg) in benzene (10 ml), p-toluenesulfonic acid monohydrate (3.7 mg) was added and the mixture was heated under reflux for 1 hour. The reaction solution was then poured into a saturated aqueous sodium hydrogencarbonate solution, extracted with dichloromethane, dried over anhydrous magnesium sulfate, filtered and concentrated under reduced pressure to obtain 33.7 mg of the desired product as a colorless oil.

$^1$H-NMR (CDCl$_3$) δ: 2.49 (3H, s), 2.55-2.65 (2H, m), 3.97 (2H, t, J=5.3 Hz), 4.35 (2H, m), 5.79 (1H, s), 6.37. (H, s), 7.22-7.36 (4H, m), 7.45-7.50 (1H, m), 7.61 (2H, d, J=7.3 Hz), 8.09 (1H, d, J=8.6 Hz).

(3) Preparation of 2-(5,6-dihydro-2H-4-pyranyl)-1-benzenesulfonyl-5-methanesulfonylindole To a solution of the compound obtained in Example 14 (2) (33.7 mg) in a mixture of tetrahydrofuran/water (3:1, 4 ml), OXONE (registered trademark) (134 mg) was added at 15 to 30° C. and the mixture was stirred for 15 hours. The reaction solution was then poured into water, extracted with dichloromethane, dried over anhydrous magnesium sulfate, filtered and concentrated under reduced pressure. The resulting residue was separated using silica gel preparative thin-layer chromatography (hexane:ethyl acetate=1:1) to obtain 28.8 mg of the desired product as a white powder.

$^1$H-NMR (CDCl$_3$) δ: 2.56 (2H, m), 3.07 (3H, s), 3.98 (2H, t, J=5.3 Hz), 4.35 (2H, d, J=2.3 Hz), 5.80 (1H, s), 6.54 (1H, s), 7.39 (2H, t, J=7.6 Hz), 7.54 (1H, t, J=7.3 Hz), 7.65 (2H, d, J=7.3 Hz), 7.86 (1H, dd, J=8.6, 1.7,Hz), 8.05 (1H, d, J=1.3 Hz), 8.37 (1H, d, J=8.6 Hz).

(4) Preparation of 2-(5,6-dihydro-2H-4-pyranyl)-5-methanesulfonylindole

To a solution of the compound obtained in Example 14 (3) (28.8 mg) in methanol (3 ml), a 1N aqueous potassium hydroxide solution (0.69 ml) was added and the mixture was stirred at 100° C. for 1 hour. The reaction solution was then poured into a saturated aqueous sodium hydrogencarbonate solution, extracted with dichloromethane, dried over anhydrous magnesium sulfate, filtered and concentrated under reduced pressure to obtain 16.5 mg of the desired product as a white powder.

$^1$H-NMR (CDCl$_3$) δ: 3.97; (2H, t, J=5.6 Hz), 4.38 (2H, d, J=2.6 Hz), 6.17 (1H, s), 6.60 (1H, s), 7.45 (1H, d, J=8.6 Hz), 7.72 (1H dd, J=8.6, 1.7 Hz), 8.20 (1H, s), 8.48 (1H brs).

(5) Preparation of 2-(5,6-dihydro-2H-4-pyranyl)-1-(4-fluorobenzyl)-5-methanesulfonyl-indole To a solution of the compound obtained in Example 14 (4) (16.5 mg) in N,N-dimethylformamide (3 ml), 60% sodium hydride (3.6 mg) was added under nitrogen atmosphere at 0° C. and the mixture was stirred for 30 minutes, followed by additin of 4-fluorobenzyl bromide (22.7 mg), and the mixture was stirred at 15 to 30° C. for 15 hours. The reaction solution was then poured into a saturated aqueous ammonium chloride solution and extracted with ethyl acetate. The organic layer was washed with water and a saturated aqueous NaCl solution, dried over anhydrous magnesium sulfate, filtered and concentrated under reduced pressure. The resulting residue was separated using silica gel preparative thin-layer chromatography (hexane:ethyl acetate=1:1) to obtain 18.4 mg of the desired product as a white powder.

$^1$H-NMR (CDCl$_3$) δ: 2.42-2.44 (2H, m), 3.07 (3H, s), 3.90 (2H, t, J=5.3 Hz), 4.26 (2H, d, J=2.6 Hz), 5.42 (2H, s), 5.84 (1H, s), 6.64 (1H, s), 6.93-7.04 (4H, m), 7.24 (1H, d, J=9.2 Hz), 7.67 (1H, dd, J=8.9, 10.7 Hz), 8.25 (1H, d, J=1.3 Hz).

EXAMPLE 15

1-(4-Fluorobenzyl)-5-methanesulfonyl-2-(5-methoxycarbonylpyridin-2-yl)indole

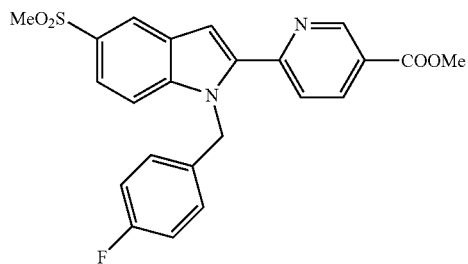

(1) Preparation of 5-ethoxycarbonyl-2-trimethylsilylethynylpyridine

To a solution of 6-chloronicotinic acid ethyl ester (1.92 g) in N,N-dimethylformamide (1 ml), trimethylsilylacetylene (2.0 g), bistriphenylphosphine palladium dichloride (210 mg), cuprous iodide (60 mg) and triethylamine (1.2 g) were added successively and the mixture was stirred in a sealed tube at 100° C. for 2 hours. After cooling, the reaction solution was poured into a saturated aqueous sodium hydrogencabonate solution, extracted with ethyl acetate, dried over anhydrous magnesium sulfate, filtered and concentrated under reduced pressure. The resulting residue was separated using silica gel column chromatography (hexane:ethyl acetate=10:1) to obtain 2.38 g of the desired product as a brown oil.

$^1$H-NMR (CDCl$_3$) δ: 0.29 (9H, s), 1.41 (3H, t, J=7.3 Hz), 4.42. (2H, q, J.=7.3 Hz), 7.52 (1H, d, J=7.9 Hz), 8.25 (1H, dd, J=2.0, 7.9 Hz), 9.15 (1H, d, J=1.7 Hz).

(2) Preparation of 1-benzenesulfonyl-2-(5-ethoxycarbonylpyridin-2-yl)-5-methanesulfonylindole A mixture of 5-ethoxycarbonyl-2-trimethylsilylethynylpyridine (3.80 g), 2-benzenesulfonylamino-3-iodo-5-methanesulfonylbenzene (3.50 g), potassium acetate (6.00 g), cuprous iodide (75 i mg), dichlorobis(triphenylphosphine) palladium (0.27 g) and N,N-dimethylformamide (10 ml) was stirred under nitrogen atmosphere at 100° C. for 8 hours. To the reaction solution was then added water and ethyl acetate. The insolubles were filtered off. The filtrate was extracted with ethyl acetate and washed with a saturated aqueous NaCl solution, dried over anhydrous sodium sulfate, filtered and concentrated under reduced pressure. The resulting residue was subjected to silica gel column chromatography (methanol:dichloromethane=1:100) to obtain 1.22 g of the desired product.

$^1$H-NMR (CDCl$_3$) δ: 1.46 (3H, t, J=7.2 Hz), 3.09 (3H, s), 4.48 (2H, q, J=7.2 Hz), 7.01 (1H, s), 7.40-7.47 (2H, m), 7.53-7.59 (1H, m), 7.76-7.80 (3H, m), 7.93 (1H, dd, J=1.7, 8.9 Hz), 8.16 (1H, d, J=1.7 Hz), 8.37 (1H, d, J=8.9 Hz), 8.32 (1H, dd, J=2.0, 8.2 Hz), 9.28 (1H, d, J=1.7 Hz).

(3) Preparation of 2-(5-ethoxycarbonylpyridin-2-yl)+ 1-(4-fluorobenzyl)-5-methanesulfonylindole A mixture of 1-benzenesulfonyl-2-(5-ethoxycarbonylpyridin-2-yl)-5-methanesulfonylindole (1.22 g), potassium hydroxide (0.33 g) and ethanol (120 ml) was stirred at 15 to 30° C. for 3 hours under nitrogen atmosphere. To the reaction solution was added water and, the mixture was neutralized with hydrochloric acid. The precipitated crystal was filtered off. To the resulting crude crystal were added 60%.sodium hydride (90 mg), 4-fluorobenzyl bromide (0.51 g) and N,N-dimethylformamide (20 ml) and the mixture was stirred at 15 to 30° C. for 30 minutes. To the reaction solution was then added water and the insolubles were filtered off. The filtrate was extracted with ethyl acetate, washed with a saturated aqueous NaCl solution, dried over anhydrous sodium sulfate, filtered and concentrated under reduced pressure. The resulting residue was subjected to silica gel column, chromatography (hexame:ethyl acetae=1:1) to obtain 0.68 g of the desired product.

$^1$H-NMR (CDCl$_3$) δ: 1.42 (3H, t, J=7.3 Hz), 3.10 (3H, s), 4.43 (2H, q, J=7.3 Hz), 6.03 (2H, s), 6.87-7.02 (4H, m), 7.20 (1H, s), 7.46 (1H, d, J=8.9 Hz), 7.76 (1H, dd, J=2.0, 8.9 Hz), 7.84 (1H, d, J=8.3 Hz), 8.33-8.36 (2H, m), 9.22 (1H, d, J=2.0 Hz).

(4) Preparation of 1-(4-fluorobenzyl)-5-methanesulfonyl-2-(5-methoxycarbonylpyridin-2-yl)indole A mixture of 2-(5-ethoxycarbonylpyridin-2-yl)-1-(4-fluorobenzyl)-5-methanesulfonylindole (0.68 g), potassium hydroxide (0.24 g) and methanol (45 ml) was stirred at 15 to 30° C. for 30 minutes under nitrogen atmosphere. To the reaction solution was added water and the mixture was neutralized with hydrochloric acid. The precipitated crystal was filtered off. The resulting crude crystal was recrystallized (methanol) to obtain 0.44 g of the desired product.

$^1$H-NMR (DMSO-d$_6$) δ: 3.21 (3H, s), 3.90 (3H, s), 6.15 (2H, s), 7.02 (4H, d, J=8.2 Hz), 7.54 (1H, s), 7.74 (1H, dd, J=1.7, 8.9 Hz), 7.84 (1H, d, J=8.9 Hz), 8.13 (1H, d, J=8.3 Hz), 8.29 (1H, d, J=1.7 Hz), 8.36 (1H, dd, J=2.0, 8.3 Hz), 9.14 (1H, d, J=2.0 Hz).

EXAMPLE 16

1-(4-Fluorobenzyl)-2-(5-carboxypyridin-2-yl)-5-methanesulfonylindole

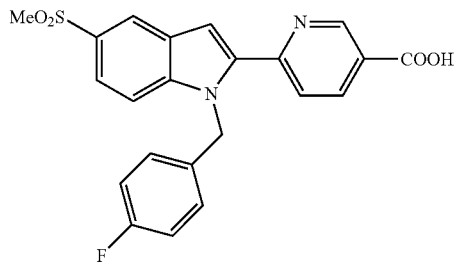

A mixture of 1-(4-fluorobenzyl)-5-methanesulfonyl-2-(5-methoxycarbonylpyridin-2-yl)indole (0.37 g), potassium hydroxide (0.12 g) and methanol (40 ml) was heated under reflux for 3 hours under nitrogen atmosphere. To the reaction solution was added water and the mixture was neutralized with hydrochloric acid. The precipitated crystal was filtered off. The resulting crude crystal was recrystallized (ethanol) to obtain 0.35 g of the desired product.

$^1$H-NMR (DMSO-d$_6$) δ: 3.21 (3H, s), 6.15 (2H, s), 7.03 (4H, d, J=7.3 Hz), 7.51 (1H, s), 7.73 (1H, dd, J=1.7, 8.9 Hz) 7.82 (1H, d, J=8.9 Hz), 8.09 (1H, d, J=8.2-Hz), 8.28 (1H, d, J=1.7 Hz), 8.34 (1H, dd, J=2.0, 8.2 Hz), 9.11 (1H, d, J=2.0 Hz), 13.38-13.50 (1H, brs).

EXAMPLE 17

1-(4-Fluorobenzyl)-5-methanesulfonyl-2-(5-methylaminocarbonylpyridin-2-yl)indole

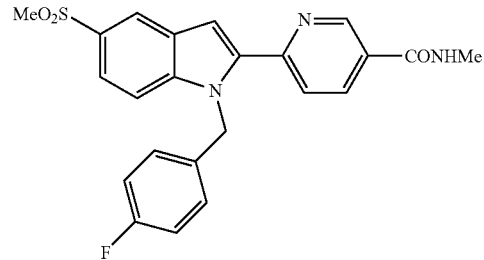

A mixture of 1-(4-fluorobenzyl)-2-(5-carboxypyridin-2-yl)-5-methanesulfonylindole (20 mg), N,N'-carbonyldiimidazole (10 mg) and tetrahydrofuran (1 ml) was stirred at 15 to 30° C. for 10 minutes under nitrogen atmosphere, followed by addition of a 40% methylamine/methanol solution (0.1 ml), and the mixture was further stirred at 15 to 30° C. for 10 minutes. The reaction solution was then concentrated under reduced pressure. The resulting residue was subjected to silica gel column chromatography (hexane:ethyl acetate=1:5) to obtain 13 mg of the desired product.

$^1$H-NMR (DMSO-d$_6$) δ: 2.82 (3H, d, J=4.6 Hz), 3.20 (3H, s), 6.13 (2H, s), 7.03 (4H, d, J=7.9 Hz), 7.47 (1H, s), 7.73 (1H, dd, J=1.7, 8.9 Hz), 7.80 (1H, d, J=8.9 Hz), 8.07 (1H, d, J=8.3 Hz), 8.25-8.28 (2H, m), 8.65-8.75 (1H, m), 9.04 (1H, d, J=1.7 Hz).

EXAMPLE 18

1-(4-Fluorobenzyl)-5-methanesulfonyl-2-(3-pyridylmethyl)indole

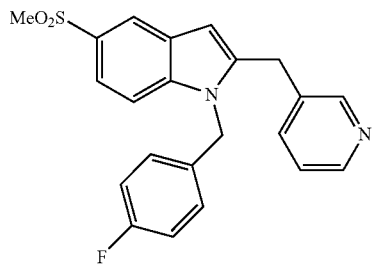

(1) Preparation of 1-benzenesulfonyl-5-methylthio-2-(3-pyridynylhydroxymethyl)indole To a mixture of 1-benzenesulfonyl-5-methylthioindole (0.91 g) and tetrahydrofuran (8 ml), a lithium diisopropylamide solution (3.22 mol) was added dropwise at −78° C. under nitrogen atmosphere, followed by stirring for 30 minutes and further stirring with heating to 0° C. for 30 minutes. A mixture of nicotinic aldehyde (0.42 g) and tetrahydrofuran (2 ml) was added dropwise at −78° C., followed by stirring for 18 hours while slowly heating to 15 to 30° C. To the reaction solution was added a saturated aqueous sodium hydrogencarbonate solution, and the mixture was extracted with dichloromethane, dried over anhydrous sodium sulfate, filtered and concentrated under reduced pressure. The resulting residue was subjected to silica gel column chromatography (hexane ethyl acetate=1:3) to obtain 0.70 g of the desired product.

$^1$H-NMR (CDCl$_3$) δ: 2.46 (3H, s), 3.95-4.08 (1H, brs), 6.14 (1H, s), 6.40 (1H, t), 7.23-7.33 (3H, m), 7.39-7.46 (2H, m), 7.53-7.59 (1H, m), 7.72-7.81 (3H, m), 8.00 (1H, d, J=8.6 Hz), 8.54-8.57 (2H, m).

(2) Preparation of 1-(4-fluorobenzyl)-5-methanesulfonyl-2-nicotinoylindole

A mixture of 1-benzenesulfonyl-5-methylthio-2-(3-pyridinylhydroxymethyl)indole (0.38 g), Dess Martin reagent (1,1,1-tris(acetyloxy)-1,1-dihydro-1,2-benziodoxol-3(1H)-one) (0.60 g) and dichloromethane (40 ml) was stirred at 15 to 30° C. for 10 minutes under nitrogen atmosphere. To the reaction solution was added a saturated aqueous sodium hydrogencarbonate solution, and the mixture was extracted with dichloromethane, dried over anhydrous sodium sulfate, filtered and concentrated under reduced pressure. To the resulting residue were added m-chloroperbenzoic acid (0.50 g) and dichloromethane (20 ml) and the mixture was stirred at 15 to 30° C. for 20 minutes. To the reaction solution was added a saturated aqueous sodium hydrogencarbonate solution, and the mixture was extracted with dichloromethane, dried over anhydrous sodium sulfate, filtered and concentrated under reduced pressure. To the resulting residue were added potassium hydroxide (0.14 g) and ethanol (20 ml) and the mixture was stirred at 70° C. for 20 minutes. To the reaction solution was added ice-water and the precipitated crystal was filtered off. To the resulting crude crystal were added 60% sodium hydride (44 mg), 4-fluorobenzyl bromide (0.19 g) and N,N-dimethylformamide (5 ml) and the mixture was stirred at 15 to 30° C. for 12 hours. To the reaction solution was then added water and the insolubles were filtered off. The filtrate was extracted with ethyl acetate, washed with a saturated aqueous NaCl solution, dried over anhydrous sodium, sulfate, filtered and concentrated under reduced pressure. The resulting residue was subjected to silica gel column chromatography (hexane:ethyl acetate=1:3) to obtain 0.10 g of the desired product.

$^1$H-NMR (CDCl$_3$) δ:3.10 (3H, s), 5.86-(2H, s), 6.94-7.16 (4H, m), 7.24 (1H, s), 7.49 (1H; dd, J=5.0, 7.9 Hz), 7.58 (1H, d, J=8.9 Hz), 7.,91 (1H, dd, J=1.7, 8.9 Hz), 8.17 (1H, dt, J=2.0, 7.9 Hz), 8.41 (1H, d, J=1.7 Hz), 8.86 (1H, dd, J=2.0, 5.0 Hz), 9.09 (1H, d, J=2.0 Hz).

(3) Preparation of 1-(4-fluorobenzyl)-5-methanesulfonyl-2-(3-pyridylmethyl)indole 1-(4-fluorobenzyl)-5-methanesulfonyl-2-nicotinoylindole (0.14 g), hydrazine monohydrate (0.17 g), potassium hydroxide (0.05 g) and ethylene glycol (3 ml) were added under nitrogen atmosphere and the mixture was stirred at 110° C. for 8 hours. To the reaction solution was added water; and the mixture was extracted with dichloromethane, washed with a saturated aqueous NaCl solution, dried over anhydrous sodium sulfate, filtered and concentrated under reduced pressure. The resulting residue was subjected to siilica gel column chromatography (hexane:ethyl acetate=1:3) to obtain 13 mg of the desired product.

$^1$H-NMR (CDCl$_3$) δ: 3.08 (3H, s), 4.05 (2H, s), 5.25 (2H, s), 6.46 (1H, s), 6.79-6.98 (4H, m), 7.21 (1H, dd, J=4.6, 7.9 Hz), 7.32 (1H, d, J=8.6 Hz), 7.43 (1H, dt, J=2.0, 7.9 Hz), 7.69 (1H, dd, J=1.7, 8.6 Hz), 8.22° (1H, d, J=1.7 Hz), 8.45 (1H, d, J=1.7 Hz), 8.45-8.50 (2H, m).

EXAMPLE 19

1-(4-Fluorobenzyl)-5-methanesulfonyl-2-(3-pyridyl)indole

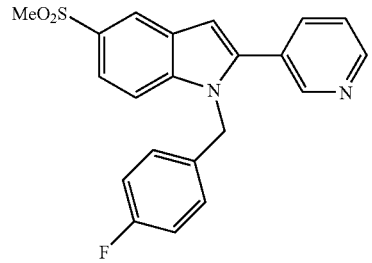

(1) Preparation of 1-benzenesulfonyl-5-methanesulfonyl-2-(3-pyridyl)indole

A mixture of 3-trimethylsilylethynylpyridine (1.07 g), 2-benzenesulfonylamino-3-iodo-5-methanesulfonylbenzene (1.75 g), potassium acetate (1.60 g), cuprous iodide (60 mg), dichlorobis(triphenylphosphine)palladium (0.20 g) and 1,4-dioxane (4 ml) was stirred at 100° C. for 12 hours under nitrogen atmosphere. To the reaction solution were added water and ethyl acetate. The insolubles were filtered off. The filtrate was extracted with ethyl acetate, dried over anhydrous sodium sulfate, filtered and concentrated under reduced pressure. The resulting residue was subjected to silica gel column chromatography (hexane:ethyl acetate=1:3) to obtain 1.04 g of the desired product.

$^1$H-NMR (CDCl$_3$) δ: 3.11 (3H, s), 6.73 (1H, s), 7.33-7.71 (6H, m), 7.90 (1H, dt, J=2.0, 7.6 Hz), 7.96 (1H, dd, J=1.7, 8.9 Hz), 8.15 (1H, d, J=2.0 Hz), 8.52-8.55 (2H, m), 8.71-8.73 (1H, m).

(2) Preparation of 1-(4-fluorobenzyl)-5-methanesulfonyl-2-(3-pyridyl)indole A mixture of 1-benzenesulfonyl-5-methanesulfonyl-2-(3-pyridyl)indole (1.00 g), potassium hydroxide (0.32 g), 1,4-dioxane (20 ml) and ethanol (20 ml) was stirred at 15 to 30° C. for 3 hours under nitrogen atmosphere. To the reaction solution was added water and the mixture was neutralized with hydrochloric acid. The precipitated crystal was filtered off. To the resulting crude crystal were added 60% sodium hydride (80 mg), 4-fluorobenzyl bromide (0.34 g) and N,N-dimethylformamide (8 ml) and the mixture was stirred at 15 to 30° C. for 1 hour. To the reaction solution was then added water, and the mixture was extracted with ethyl acetate, washed with a saturated aqueous sodium hydrogencarbonate solution, dried over anhydrous sodium sulfate, filtered and concentrated under reduced pressure. The resulting residue was subjected to silica gel colmn chromatography (hexane:ethyl acetate=1:3) to obtain 0.42 g of the desired product.

$^1$H-NMR (CDCl$_3$) δ: 3.11 (3H, s), 5.38 (2H, s), 6.85 (1H, s), 6.87-7.01 (5H, m), 7.34-7.38 (2H, m), 7.68 (1H, dt, J=2.0, 7.9 Hz), 7.74 (1H, dd, J=1.7, 8.9 Hz), 8.34 (1H, d, J=1.7 Hz), 8.60-8.85 (2H, m).

EXAMPLE 20

1-(4-Fluorobenzyl)-5-methanesulfonyl-2-(1-oxy-3-pyridyl)indole

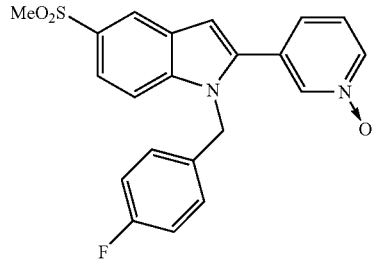

1-(4-fluorobenzyl)-5-methanesulfonyl-2-(3-pyridyl)indole (0.28 g), m-chloroperbenzoic acid (0.34 g) and dichloromethane (20 ml) were added under nitrogen atmosphere and the mixture was stirred at 15 to 30° C. for 26 hours. To the reaction solution were added sodium thiosulfate and potassium carbonate, and the mixture was filtered and concentrated under reduced pressure. The resulting residue was subjected to silica gel column chromatography (dichloromethane:methanol=20:1) to obtain 46;mg of the desired product.

$^1$H-NMR (CDCl$_3$) δ: 3.10 (3H, s) 5.41 (2H, s), 6.86-7.03 (5H, m), 7.24 (1H, dt, J=1.3, 7.9 Hz), 7.27-7.39 (2H, m), 7.77 (1H, dd, J=1.7, 8.9 Hz), 8.22-8.35 (3H, m).

EXAMPLE 21

1-(4-Fluorobenzenesulfonyl)-5-methanesulfonyl-2-(thiazol-2-yl)indole

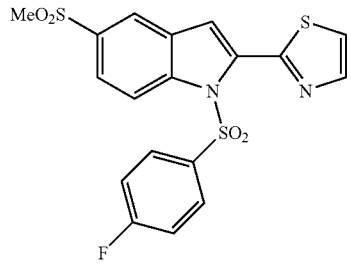

To a mixture of 5-methanesulfonnyl-2-(thiazol-2-yl)indole (50 mg) and-N,N-dimethylformamide (1.8 ml), 60% sodium hydride (10 mg) was added at 0° C. and the mixture was stirred at the same temperature for 15 minutes. To the reaction mixture was added 4-fluorobenzenesulfonyl chloride (52 mg) at 0° C. and the mixture was stirred at 15 to 30° C. for 1 hour. The reaction mixture was diluted with ethyl acetate, washed with a saturated aqueous sodium hydrogencarbonate solution, water and a saturated aqueous NaCl solution successively, dried over sodium sulfate and concentrated under reduced pressure. The resulting residue was subjected to silica gel column chromatography (hexane:ethyl acetate=1:1) to obtain 77 mg of the desired product in a white amorphous form.

$^1$H-NMR (CDCl$_3$) δ: 3.09 (3H, s), 7.04 (1H, s), 7.15 (2H, t, J=8.2 Hz), 7.63 (1H, d, J-3.3 Hz), 7.96 (1H, dd, J=1.7, 8.6 Hz), 8.0-8.1 (3H, m), 8.20 (1H, d, J=1.7 Hz), 8.36 (1H, d, J=8.6 Hz).

EXAMPLE 22

1-(4-Fluorobenzyl)-5-methanesulfonyl-2-(5-methyl-[1,2,4]triazol-3-yl)indole

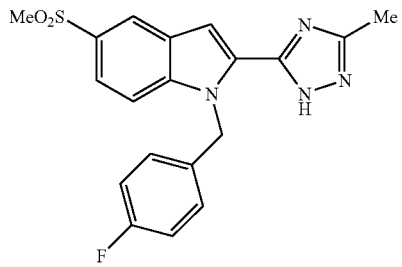

(1) Preparation of 1-benzenesulfonyl-5-methylthioindole-2-carboxylic acid methyl ester A mixture of 1-benzenesulfonyl-5-methylthioindole-2-carboxylic acid (3.5 g), sulfuric acid (10 ml) and methanol (10 ml) was heated, under reflux for 12 hours. The reaction mixture was poured into ice-water and the mixture was extracted with dichloromethane. The organic layer was washed with water, dried over sodium sulfate and concentrated under reduced pressure. The resulting residue was subjected to silica gel column chromatography (dichloromethane) to obtain 3.4 g of the desired product as a white crystal.

$^1$H-NMR (CDCl$_3$) δ: 2.51 (3H, s), 3.93 (3H, s), 7.10 (1H, s), 7.37 (1H, dd, J=2.0, 8.9 Hz), 7.44 (1H, d, J=2.0 Hz), 7.48 (2H, t, J=7.9 Hz), 7.58 (1H, t, J=7.9 Hz), 8.01 (2H, d, J=7.9 Hz), 8.05 (1H, d, J=8.9. Hz).

(2) Preparation of 5-methanesulfonylindole-2-carboxylic acid methyl ester

To a mixture of the compound obtained in Example 22 (1) (3.4 g), tetrahydrofuran (90 ml) and water (45 ml), OXONE (registered trademark) (8.7 g) was added at 0° C. and the mixture was stirred for 20 minutes and at 15 to 30° C. for 1 hour. The mixture was diluted with ethyl acetate. The organic layer was washed with water and dried over sodium-sulfate. The solvent was distilled off under reduced pressure to obtain 3.5 g of a white amorphous 1-benzenesulfonyl-5-methanesulfonylindole-2-carboxylic acid methyl ester as a crude product, which was used in the next reaction without; further purification.

To a mixture of the resulting 1-benzenesulfonyl-5-methanesulfonylindole-2-carboxylic acid methyl ester (3.5 g), tetrahydrofuran (45 ml) and methanol (12 ml), potassium hydroxide (0.79 g) was added at 0° C. and the mixture was stirred at the same temperature for 3 hours. 2N, hydrochloric acid was added, and the mixture was extracted with dichloromethane. The organic layer was washed with water and dried over sodium sulfate. The solvent was distilled off under reduced pressure to obtain 2.2 g of a white amorphous 5methanesulfonylindole-2-carboxylic acid methyl ester as a crude product.

$^1$H-NMR (CDCl$_3$) δ: 3.10 (3H, s), 3.99 (3H, s), 7.35 (1H, d, J=1.7 Hz), 7.58 (1H, d, J=8.6 Hz), 7.86 (1H, dd, J=1.7, 8.6 Hz), 8.38 (1H, s), 9.24 (1H, brs).

(3) Preparation of 1-(4-fluorobenzyl)-5-methanesulfonylindole-2-carboxylic acid methyl ester To a mixture of the compound obtained in Example 22 (2) (1.2 g) and N,N-dimethylformamide (23 ml), 60% sodium hydride (204 mg) was added at 0° C. and the mixture was stirred at the same temperature for 20 minutes. To the reaction mixture was added 4-fluorobenzyl bromide (0.65 ml) at 0° C. and the mixture was stirred at 15 to 30° C. for 2 hours. 2N hydrochloric acid was added thereto, and the mixture was extracted with ethyl acetate. The organic layer was washed with water, dried over sodium sulfate and concentrated under reduced pressure. The resulting residue was subjected to silica gel column chromatography (dichloromethane) to obtain 1 g of the desired product in a white amorphous form.

$^1$H-NMR (CDCl$_3$) δ: 3.09 (3H, s), 3.92 (3H, s), 5.86 (2H, s), 6.9-7.1 (4H, m), 7.50 (1H, s), 7.50 (1H, d, J=8.6 Hz), 7.83 (1H, dd, J=2.0, 8.6 Hz), 8.38 (1H, d, J=2.0 Hz).

(4) Preparation of 1-(4-fluorobenzyl)-5-methanesulfonylindole-2-carboxylic acid

To a mixture of the compound obtained in Example 22 (3) (0.26,g), tetrahydrofuran (5 ml) and methanol (10 ml), a 1N aqueous sodium hydroxide solution (5 ml) was added at 15 to 30° C. and the mixture was stirred for 2 hours. 1N hydrochloric acid was added thereto and the mixture was extracted with dichloromethane. The organic layer was washed with water, dried over sodium sulfate and concentrated under reduced pressure to obtain 0.25 g of the desired product as a white crystal.

$^1$H-NMR (CDCl$_3$) δ: 3.10 (3H, s), 5.86 (2H, s), 6.9-7.1 (4H, m), 70.52 (1H, d, J=8.9 Hz), 7.64 (1H, s), 7.86 (1H, dd, J=1.6, 8.9 Hz), 8.41 (1H, d, J=1.6 Hz).

(5) Preparation of 1-(4-fluorobenzyl)-5-methanesulfonylindole-2-carboxamide

To a mixture of the compound obtained in Example 22 (4) (0.23 g) and tetrahydrofuran (7 ml), triethylamine (0.19 ml) and ethyl chlorocarbonate (0.1 ml) were added at 0° C. and the mixture was stirred at the same temperature for 20 minutes. An ammonia gas was blown into the mixture at 0° C. and the mixture was stirred at the same temperature for 30 minutes. Water was added thereto and the mixture was extracted with ethyl acetate. The organic layer was washed with water, dried over sodium sulfate and concentrated under reduced pressure. The resulting residue was recrystallized (ethyl acetate) to obtain 0.06 g of the desired product as a white crystal.

$^1$H-NMR (CDCl$_3$) δ: 3.09 (3H, 5), 5.4-6.2 (2H, m), 5.86 (2H, s), 6.9-7.0 (2H, m), 7.0-7.2 (3H, m), 7.50 (1H, d, J=8.9 Hz), 7.79 (1H, dd, J=1.7, 8.9 Hz), 8.35 (1H, d, J=1.7 Hz).

(6)-Preparation of 1-(4-fluorobenzyl)-5-methanesulfonyl-2-(5-methyl-[1,2,4]triazol-3-yl)indole A mixture of the compound obtained in Example 22 (5) (55 mg) and dimethylacetamide dimethylacetal (11 ml) was stirred at 110° C. for 1 hour. The reaction mixture was concentrated under reduced pressure. A mixture of the resulting residue, hydrazine monohydrate (0.05 ml) and acetic acid (0.5 ml) was stirred at 90° C. for 2 hours. Water was added thereto and the mixture was extracted with ethyl acetate. The organic layer was washed with water, dried over sodium sulfate and concentrated under reduced pressure. The resulting residue was subjected to silica gel column chromatography (hexane ethyl acetate=1:2) to obtain 25 mg of the desired product as a white powder.

$^1$H-NMR (CDCl$_3$) δ: 2.56 (3H, s), 3.09 (3H, s), 6.00 (2H, s), 6.92 (2H, t, J=8.6 Hz), 7.00 (2H, m), 7.37 (1H, s), 7.39 (1H, d, J=8.9 Hz), 7.71 (1H, dd, J=1.7, 8.9 Hz), 8.32 (1H, d, J=1.7 Hz).

EXAMPLE 23

1-(4-Fluorobenzyl)-5-methanesulfonyl-2-(3-methyl-[1,2,4]oxadiazol-5-yl)indole

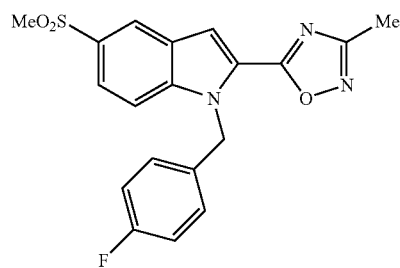

A mixture of 1-(4-fluorobenzyl)-5-methanesulfonylindole-2-carboxamide (63 mg) and dimethylacetamide dimethylacetal (1 ml) was stirred at 110° C. for 1 hour. The reaction mixture was concentrated under reduced pressure. A mixture of the resulting residue, hydroxylamine hydrochloride (25 mg), a 2N aqueous sodium hydroxide solution (0.18 ml), 1,4-dioxane (0.4 ml) and acetic, acid (0.4 ml) was stirred at 90° C. for 2 hours. Water was added thereto and the mixture was extracted with ethyl acetate. The organic layer was washed with water, dried over sodium sulfate and concentrated under reduced pressure. The resulting residue was subjected to silica gel column chromatography (hexane:ethyl acetate=1:1) to obtain 50 mg of the desired product as a white crystal.

$^1$H-NMR (CDCl$_3$) δ: 2.47 (3H, s), 3.10 (3H, s), 6.02 (2H, s), 6.9-7.1 (4H, m), 7.50 (1H, d, J=8.9 Hz), 7.64 (1H, s), 7.84 (1H, dd, J=1.7, 8.9 Hz), 8.41 (1H, d, J=1.7 Hz).

EXAMPLE 24

1-(4-Fluorobenzyl)-5-methanesulfonyl-2-(5-methyl-[1,2,4]oxadiazol-3-yl)indole

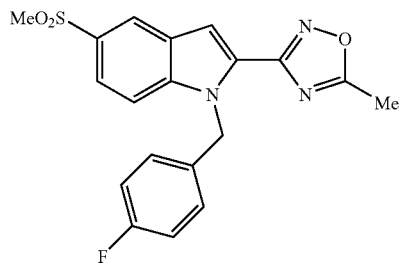

(1) Preparation of 2-cyano-1-(4-fluorobenzyl)-5-methanesulfonylindole

To a mixture of 1-(4-fluorobenzyl)-5-methanesulfonylindole-2-carboxamide (100 mg) and dichloromethane (2 ml), triethylamine (0.09 ml) and anhydrous trifluoroacetic acid (0.09 ml) were added at 15 to 30° C. and the mixture was stirred at the same temperature for 2 hours. Water was added therto, and the mixture was extracted with dichloromethane. The organic layer was washed with water, dried over sodium sulfate and concentrated under reduced pressure. The resulting residue was subjected to silica gel column chromatography (hexane:ethyl acetate=2:1) to obtain 68 mg of the desired product as a white crystal.

$^1$H-NMR (CDCl$_3$) δ: 53.08 (3H, s), 5.51 (2H, s), 6'.9-7.1 (2H, m), 7.1-7.2 (2H, m), 7.39 (1H, s), 7.49 (1H, d, J=8.9 Hz), 7.88 (1H, dd, J=1.6, 8.9 Hz), 8.37 (1H, d, J=1.6 Hz).

(2) Preparation of 1-(4-fluorobenzyl)-5-methanesulfonyl-2-(5-methyl-[1,2,4]oxadiazol-3-yl)indole A mixture of the compound obtained in Example 24 (1) (68 mg), hydroxylamine hydrochloride (22 mg), potassium hydroxide (18 mg) and ethanol (1 ml) was heated under reflux for 2 hours. After the insolubles were filtered off, the reaction mixture was concentrated under reduced pressure. A mixture of the resulting residue and dimethylacetamide dimethylacetal (1-ml) was stirred at 100° C. for 1 hour. Water was added thereto, and the mixture was extracted with ethyl acetate. The organic layer was washed with water, dried over sodium sulfate and concentrated under reduced pressure. The resulting residue was subjected to silica gel column chromatography (hexane ethyl acetate=1:1) to obtain 50 mg of the desired product as a white crystal.

$^1$H-NMR (CDCl$_3$) δ: 2.66 (3H, s), 3.10 (3H, s), 5.92 (2H, s), 6.9-7.1 (4H, m), 7.46 (1H, d, J=8.9 Hz), 7.52 (1H, s), 7.80 (1H, dd, J=1.7, 8.9 Hz), 8.37 (1H, d, 1.7 Hz).

EXAMPLE 25

1-(4-Fluorobenzyl)-5-methanesulfonyl-2-(tetrahydropyran-4-yl)indole

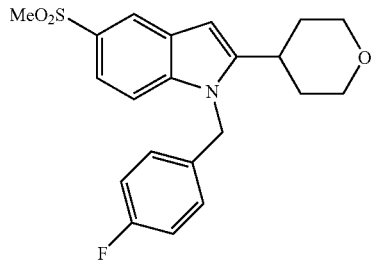

A mixture of 2-(5,6-dihydro-2H-4-pyranyl)-1-(4-fluorobenzyl)-5-methanesulfonyl-indole (83 mg), 10% palladium carbon (15 mg) and ethanol (5 ml) was stirred at 15 to 30° C. for 24 hours under hydrogen atmosphere. The mixture was filtered and the mother liquid was concentrated under reduced pressure. The resulting residue was subjected to silica gel column chromatography (hexane:ethyl acetate=0.2:1) to obtain 40 mg of the desired product as a white crystal.

$^1$H-NMR (CDCl$_3$) δ: 1.7-2.0 (4H, m), 2.88 (1H, m), 3.07 (3H, s), 3.47 (2H, m), 4.05 (2H, m), 5.39 (2H, s), 6.54 (1H, s), 6.84-6.91 (2H, m), 6.99 (2H, t, J=8.6 Hz), 7.26 (1H, d, J=8.6 Hz), 7.65 (1H, dd, J=1.7, 8.6 Hz), 8.22 (1H, d, J=1.7 Hz).

EXAMPLE 26

5-Methanesulfonyl-2-(1-oxy-2-pyridyl)-1-(4-fluorobenzyl)-1H-pyrrolo[2,3-b]pyridine

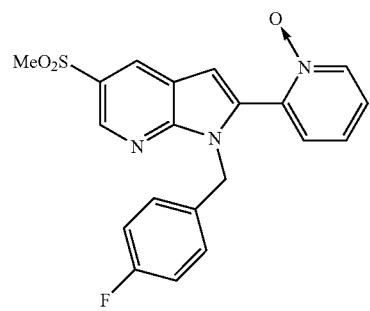

To a mixture of 5-methanesulfonyl-2-(2-pyridyl)-1-(4-fluorobenzyl)-1H-pyrrolo[2,3-b]pyridine (10 mg) and dichloroethane (0.3 ml), m-chloroperbenzoic acid (10 mg) was added at 0° C. and the mixture was stirred at 15 to 30° C. for 3 hours. The reaction mixture was diluted with dichloromethane, washed with a 1N aqueous sodium hydroxide solution, dried over sodium sulfate and concentrated under reduced pressure. The resulting residue was subjected to silica gel preparative thin-layer chromatography (dichloromethane:methanol=95:5) to obtain 2 mg of the desired product as a yellow-white powder.

$^1$H-NMR (CDCl$_3$) δ: 3.16 (3H, s), 5.76 (2H, s), 6.7-6.9 (5H, m), 7.08-7.21 (2H, m), 7.35 (1H, m), 8.35 (1H, d, J=6.6 Hz), 8.56 (1H, d, J=2.3 Hz), 8.97 (1H, d, J=2.3 Hz).

EXAMPLE 27

1-(4-Fluorobenzyl)-5-methanesulfonyl-2-(2-thiazolylmethyl)indole

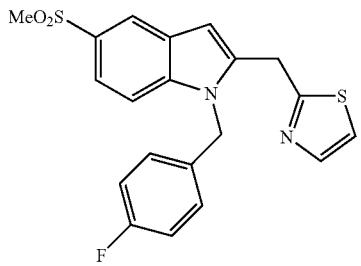

(1) Preparation of 1-benzenesulfonyl-5-methylthioindole 2-carboxylic acid methyl ester A mixture of 1-benzenesulfonyl-5-methylthioindole-2-carboxylic acid (3.5 g), sulfuric acid (10 ml) and methanol (10 ml) was heated under reflux for 12 hours. The reaction mixture was poured into ice-water and extracted with dichloromethane. The organic layer was washed with water, dried overt sodium sulfate and concentrated under reduced pressure. The resulting residue, was subjected to silica, gel column chromatography (dichloromethane) to obtain 3.4 g of the desired product as a white crystal.

$^1$H-NMR (CDCl$_3$) δ: 2.51 (3H, s), 3.93 (3H), 7.10 (1H, s), 7.37 (1H, dd; J=2.0, 8.9 Hz), 7.44 (1H, d, J=2.0 Hz), 7.48 (2H, t, J=7.9 Hz), 7.58; (1H, t, J=7.9 Hz), 8.01 (2H, d J=7. Hz), 8.05 (H., id, J=8.9 Hz).

(2) Preparation of 5-methanesulfonylindole-2-carboxylic acid methyl ester

To a mixture of the compound obtained in Example 27 (1) (3.4 g), tetrahydrofuran (90 ml) and water (45 ml), OXONE (8.7 g) was added at 0° C. and the mixture was stirred for 20 minutes and at 15 to 30° C. for 1 hour. The mixture was diluted with ethyl acetate. The organic layer was washed with water and dried over sodium sulfate. The solvent was distilled off under reduced pressure to obtain 3.5 g of a white amorphous 1-benzenesulfonyl-5-methanesulfonylindole-2-carboxylic acid methyl ester as a crude product.

To a mixture of the resulting 1-benzenesulfonyl-5-methanesulfonylindole-2-carboxylic acid methyl ester (3.5 g), tetrahydrofuran (45 ml) and methanol (12 ml), potassium hydroxide (0.79 g) was added at 0° C. and the mixture was stirred at the same temperature for 3 hours. 2N hydrochloric acid was added thereto, and the mixture was extracted with dichloromethane. The organic layer was washed with water and dried over sodium sulfate. The solvent was distilled off under reduced pressure to obtain 2.2 g of a white amorphous 5-methane sulfonylindole-2-carboxylic acid methyl ester as a crude product.

$^1$H-NMR (CDCl$_3$) δ: 3.10 (3H, s), 3.99 (3H, s),7.35 (1H, d, J=1.7 Hz), 7.58 (1H, d, J=8.6 Hz), 7.86 (1H, dd, J=1.7, 8.6 Hz), 8.38 (1H, s), 9.24 (1H, brs).

(3) Preparation of 1-(4-fluorobenzyl)-5-methanesulfonylindole-2-carboxylic acid methyl ester To a mixture of the compound obtained in Example 27 (2) (1.2 g) and N,N-dimethylformamide (23 ml), 60% sodium hydride (204 mg) was added at 0° C. and the mixture was stirred at the same temperature for 20 minutes. To the reaction mixture was added 4-fluorobenzyl bromide (0.65 ml) at 0° C. and the mixture was stirred at 15 to 30° C. for 2 hours. 2N hydrochloric acid was added thereto, and the mixture was extracted with ethyl acetate. The organic layer was washed with water, dried over sodium sulfate and concentrated under reduced pressure. The resulting residue was subjected to silica gel column chromatography (dichloromethane) to obtain 1 g of the desired product in a white amorphous form.

$^1$H-NMR (CDCl$_3$) δ: 3.09 (3H, s), 3.92 (3H, s), 5.86 (2H, s), 6.9-7.1 (4H, m), 7.50 (1H, s), 7.50 (1H, d, J=8.6 Hz), 7.83 (1H, dd, J=2.0, 8.6 Hz), 8.38 (1H, d, J=2.0 Hz).

(4) Preparation of 1-(4-fluorobenzyl)-5-methanesulfonylindole-2-carbaldehyde To a solution of lithium aluminum hydride (366 mg) in tetrahydrofuran (20 ml), a solution of 1-(4-fluorobenzyl)-5-methanesulfonylindole-2-carboxylic acid methyl ester obtained in Example 27 (3) (1.86 g) in tetrahydrofuran (20 ml) was added dropwise at 0° C. under nitrogen atmosphere and the mixture was stirred at the same temperature for 30 minutes. The reaction solution was poured into water, filtered through Celite and extracted with chloroform. The organic layer was washed with water and dried. The solvent was distilled off under reduced pressure to obtain (1-(4-fluorobenzyl)-5-methanesulfonylindol-2-yl)-methanol (1.8° g). To a solution of the resulting alcohol (1.8 g) in dichloromethane (100 ml) was added manganese dioxide (15.3 g) at 15 to 30° C. and the mixture was stirred at the same temperature for 30 minutes. The reaction solution was filtered through Celite. The solvent was distilled off under reduced pressure to obtain 1.5 g (88.4%) of the desired product as a yellow powder.

$^1$H-NMR (CDCl$_3$) δ: 3.09 (3H, s), 5.83 (2H, s), 6.94 (2H, t, J=8.3 Hz), 7.03-7.15 (2H, m), 7.50 (1H, s), 7.55 (1H, d, J=8.9 Hz), 7.89 (1H, dd, J=1.7, 8.9 Hz), 8.44 (1H, s), 9.97 (1H, s).

(5) Preparation of (1-(4-fluorobenzyl)-5-methanesulfonylindol-2-yl)(thiazol-2-yl)-methanol To a mixture of 2-bromothiazole (123 mg) and tetrahydrofuran (3.5 ml), 1.61 M n-butyl lithium solution in hexane (0.51 ml) was added at −78° C. and the mixture was stirred for 30 minutes, followed by addition of a solution of 1-(4-fluorobenzyl)-5-methanesulfonylindole-2-carbaldehyde (50 mg) obtained in Example 27 (4) in tetrahydrofuran (3.5 ml) at the same temperature, and the mixture was stirred as such for 30 minutes. The reaction mixture was poured into a saturated aqueous ammonium chloride solution, extracted with chloroform, washed with water, dried over anhydrous magnesium sulfate and concentrated under reduced pressure. The resulting residue was subjected to silica gel preparative thin-layer chromatography (hexane:ethyl acetate=1:1) to obtain 18 mg of the desired product as a yellow oil.

$^1$H-NMR (CDCl$_3$) δ: 3.09 (3H, s), 5.56 (1H, d, J=17.5 Hz)., 5.67 (1H, d, J=16.2 Hz), 6.27 (1H, s), 6.63 (1H, s), 6.90-7.02 (4H, m), 7.41 (1H, d, J=8.9 Hz), 7.54 (1H, d, J=3.3 Hz), 7.62-7.70 (2H, m), 8.20 (1H, d, J=11.3 Hz).

(6) Preparation of 1-(4-fluorobenzyl)-5-methane-sulfonyl-2-(2-thiazolylcarbonyl)indole To absolution of the compound obtained in Example 27 (5) (110 mg) in dichloromethane (20 ml), manganese dioxide (900 mg) was added at 15 to 30° C. and the mixture was stirred for 30 minutes. The reaction solution was then filtered through Celite and concentrated under reduced pressure. The resulting residue was subjected to silica gel preparative thin-layer chromatography (hexane:ethyl acetate=1:1) to obtain 50 mg of the desired products as a yellow powder.

$^1$H-NMR (CDCl$_3$) δ: 3.10 (3H, s), 5.91 (2H, s), 6.96 (2H, t, J=8.6 Hz), 7.07-7.13 (2H, m), 7.55 (1H, d, J=8.9 Hz), 7.75 (1H, d, J=3.0 Hz), 7.89 (1H, dd, J=1.7, 8.9 Hz), 8.13 (1H, d, J=3.0 Hz), 8.49 (1H, s), 8.61 (1H, s).

(7) Preparation of 1-(4-fluorobenzyl)-5-methane-sulfonyl-2-(2-thiazolylmethyl)indole To a mixture of the compound obtained in Example 27 (6) (88 mg), potassium hydroxide. (25 mg) and ethylene glycol (2.5 ml), hydrazine. (65-mg) was added and the mixture was stirred at 120° C. for 3 hours. The reaction mixture was poured into water, extracted with chloroform, dried over anhydrous magnesium sulfate and concentrated under reduced pressure. The resulting residue was separated and purified twice with silica gel preparative thin-layer chromatography (hexane:ethyl acetate=1:1) and (chloroform:methanol=15:1) to obtain 39 mg of the desired product as a yellow oil.

$^1$H-NMR (CDCl$_3$) δ: 3.08 (3H, s), 4.48 (2H, S), 5.39 (2H, s), 6.70 (1H, s), 6.81-6.96 (4H, m), 7.23 (1H, d, J=3.3 Hz), 7.32 (1H, d, J=8.6 Hz), 7.65 (1H, d, J=3.3 Hz), 7.69 (1H, dd, J=1.7, 8.6 Hz), 8.23 (1H, d, J=1.7 Hz).

EXAMPLE 28

6-(1-(4-Fluorobenzyl)-5-methanesulfonyl-1H-pyrrolo[2,3-b]pyridin-2-yl)nicotinic acid methylamide

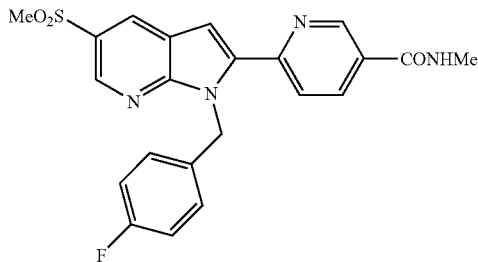

(1) Preparation of 6-(1-benzenesulfonyl-5-methylthio-1H-pyrrolo [2,3-b]pyridin-2-yl)nicotinic acid ethyl ester To a solution of 2-benzenesulfonylamino-5-methylthio-3-iodo-pyridine (100 mg) in 1,4-dioxane (2.5 ml), 5-ethoxycarbonyl-2-trimethylsilylethynylpyridine (185 mg), bistriphenylphosphine palladium dichloride (9 mg), cuprous iodide (5 mg) and potassium acetate (37 mg) were added successively and the mixture was stirred in a sealed tube at 100° C. for 15 hours. After cooling, the reaction solution was poured into water, extracted with ethyl acetate, dried over anhydrous magnesium sulfate, filtered and concentrated under reduced pressure. The resulting residue was separated using silica gel preparative thin-layer chromatography (hexane:ethyl acetate=2:1) to obtain 110 mg of the desired product as an orange oil.

$^1$H-NMR (CDCl$_3$) δ: 1.45 (3H, t, J=7.3 Hz), 2.49 (3H, s), 4.46 (2H, q, J=7.3 Hz), 6.76 (1H, s), 7.43-7.63 (3H, m), 7.73-7.79 (2H, m), 8.17-8.21 (2H, m), 8.40 (1H, d, J=8.3 Hz), 8.44 (1H, s), 9.30 (1H, s).

(2) Preparation of 6-(1-benzenesulfonyl-5-methane-sulfonyl-1H-pyrrolo[2,3-b]pyridin-2-yl)nicotinic acid ethyl ester To a solution of the compound obtained in Example 28 (1) (110 mg) in a mixture of dichloromethane/methanol, (5:1, 9 ml), magnesium monoperoxyphthalate (314 mg, 80% purity) was added at 0° C. and the mixture was stirred at the same temperature for 30 minutes and at 15 to 30° C. for 1 hour. The reaction solution was poured into a saturated aqueous sodium hydrogencarbonate solution, extracted with chloroform, dried over anhydrous magnesium sulfate, filtered and concentrated under reduced pressure. The resulting residue was separated using silica gel preparative thin-layer chromatography (hexane chloroform:acetone=6:3:1) to obtain 50 mg of the desired product as a yellow oil.

$^1$H-NMR (CDCl$_3$) δ: 1.47 (3H, t, J=7.3 Hz), 3.13 (3H, s), 4.49 (2H, q, J=7.3 Hz), 6.88 (1H, s), 7.54-7.70 (3H, m), 7.77. (1H, d, J=7.9 Hz), 8.35-8.43 (2H, m), 8.45-8.50 (2H, m), 9.04 (1H, s), 9.34 (1H, s).

(3) Preparation of (1-(4-fluorobenzyl)-5-methane-sulfonyl-1H-pyrrolo[2,3-b]pyridin-2-yl) nicotinic acid methylamide To a solution of the compound obtained in Example 28 (2) (50 mg) in methanol (6 ml), a 1N aqueous potassium hydroxide solution (0.3 ml) was added and the mixture was stirred at 60° C. for 1 hour. The reaction solution was then poured into water. After pH was adjusted to 7.0, the mixture was filtered off. The residue was washed with water and ether and dried to obtain 11 mg of a compound as a white powder. The resulting compound (11 mg) was dissolved in N,N-dimethylformamide (1.0 ml). 60% Sodium hydride (1.8 mg) was added thereto at 0° C. and the mixture was stirred for 30 minutes, followed by addition of 4-fluorobenzyl bromide (11 mg), and the reaction solution was stirred at 15 to 30° C. for 1 hour. The reaction solution was poured into a saturated aqueous ammonium chloride solution, extracted with chloroform, dried over anhydrous magnesium sulfate, filtered and concentrated under reduced pressure. The resulting residue was separated using silica gel thin-layer chromatography (hexane:ethyl acetate=1:1) to obtain 3 mg of a compound as a white powder. Further, to this compound (3 mg) was added a solution of methylamine in 40% methanol (1.0 ml) and the mixture was stirred at 15 to 30° C. for 30 minutes. The reaction solution was concentrated under reduced pressure. The resulting residue was washed with ether to obtain 3 mg of the desired product as a white powder.

$^1$H-NMR (CDCl$_3$) δ: 3.08 (3H, d, J=4.6 Hz), 3.17 (3H, s), 6.21 (2H, s), 6.79-7.04(4H, m), 7.08 (1H, s), 7.65 (1H, s), 7.78 (1H, d, J=8.3 Hz), 8.15 (1H, dd, J=2.0, 7.9 Hz), 8.54 (1H, d, J=2.3 Hz), 8.94 (1H, d, J=2.3 Hz), 9.04 (1H, d, J=2.0 Hz).

EXAMPLE 29

2-(2-Carboxyfuran-5-yl)-1-(4-fluorobenzyl)-5-methanesulfonyl-indole

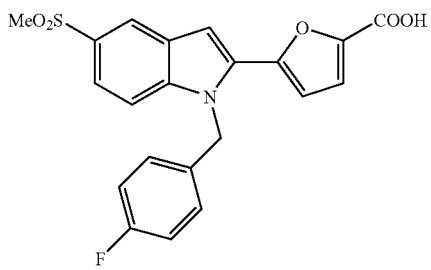

(1) Preparation of 2-bromo-5-ethoxycarbonyl-furan

To absolution of 2-bromo-5-carboxyfuran (10 g) in dimethyl sulfoxide (100 ml), potassium carbonate (7.96 g) was added at 15 to 30° C. and ethyl iodide (16.8 ml) was added dropwise thereto. The mixture was stirred for 15 hours. The reaction solution was then poured into water and extracted with chloroform. The organic layer was washed with water, a saturated aqueous sodium hydrogencarbonate solution and a saturated aqueous NaCl solution, dried over anhydrous sodium sulfate, filtered and concentrated under reduced pressure. The resulting residue was separated using silica gel column chromatography (hexane:ethyl acetate=2;1) to obtain 11.34 g of the desired product as an oil.

$^1$H-NMR (CDCl$_3$) δ: 1.36 (3H, t, J=7.0 Hz), 4.34 (2H, q, J=7.0 Hz), 6.43 (1H, d, J=3.6 Hz), 7.10 (1H, d,J=3.6 Hz).

(2) Preparation of 2-ethoxycarbonyl-5-trimethylsilylethynyl-furan

To a solution of the compound obtained in Example 29 (1) (0.5 g) in N,N-dimethylformamide (5 ml), trimethylsilylacetylene (0.65 ml), bistriphenylphosphine palladium dichloride (0.16 g), cuprous iodide (0.04 g) and triethylamine (0.64 ml) were added successively and the mixture was stirred in a sealed tube at 100° C. for 2 hours. After cooling, the reaction solution was poured into water, extracted with ethyl acetate, washed with a saturated aqueous NaCl solution, dried over anhydrous sodium sulfate, filtered and concentrated under reduced pressure. The resulting residue was separated using silica gel column chromatography (hexane:ethyl acetate=4:1) to obtain 0.3782 g of the desired product as a brown oil.

$^1$H-NMR (CDCl$_3$): 0.25 (9H, s), 1.37 (3H, t, J=7.2 Hz), 4.36 (4H, q, J=7.2 Hz), 6.35 (1H, d, J=3.6 Hz), 7.26 (1H, d, J=3.6 Hz).

(3) Preparation of 2-(2-ethoxycarbonylfuran-5-yl)-5-methanesulfonyl-indole

To a solution of the compound obtained in Example 29' (2) (0.1 g) in N,N-dimethylformamide (1 ml) 2-benzenesulfonylamino-3-iodo-5-methanesulfonylbenzene (0.0925 g), bistriphenylphosphine palladium dichloride (0.015 g), cuprous iodide (0.004 g) and potassium acetate (0.04 g) were added successively and the mixture was stirred in a sealed tube at 100° C. for 2 hours. After cooling, the reaction solution was poured into water, extracted with ethyl acetate, washed with a saturated aqueous NaCl solution, dried over anhydrous magnesium sulfate, filtered and concentrated under reduced pressure. The resulting residue was separated using silica gel column chromatography (hexane:ethyl acetate=1:1) to obtain 0.0462 g of the desired product as a brown solid.

$^1$H-NMR (CDCl$_3$) δ: 1.41 (3H,t, J=6.9 Hz), 3.09 (3H, s), 4.17 (2H, q, J=6.9 Hz), 6.8 (1H, d, J=3.6 Hz), 7.00 (1H, s), 7.28 (1H, d, J=3.6 Hz), 7.54 (1H, d, J=8.9 Hz), 7.77 (1H, d, J=8.9 Hz), 9.15 (1H, brs).

(4) Preparation of 2-(2-ethoxycarbonylfuran-5-yl)-1-(4-fluorobenzyl)-5-methanesulfonyl-indole To a solution of the compound obtained in Example 29 (3) (0.0457 g) in N,N-dimethylformamide (1.4 ml), 60% sodium hydride (0.006 g) was added at 0° C. under nitrogen atmosphere and the mixture was stirred for 15 minutes, followed by addition of 4-fluorobenzyl bromide (0.02 ml), and the mixture was stirred for 1 hour. The reaction solution was then poured into water and extracted with ethyl acetate. The organic layer was washed with a saturated aqueous NaCl solution, dried over anhydrous magnesium sulfate, filtered and concentrated under reduced pressure. The resulting residue was separated using silica gel column chromatography (hexane ethyl acetate=1:1) to obtain 0.0403 g of the desired product as a white solid.

$^1$H-NMR (CDCl$_3$). δ: 1.37 (3H, t, J=7.2 Hz), 3.09 (3H, s), 4.36 (2H, q, J=7.2 Hz), 5.66 (2H, s), 6.45 (1H, d, J=3.6 Hz), 6.91-7.06 (4H, m), 7.11 (1H, s), 7.20 (1H, d, J=3.6 Hz), 7.46 (1H, d, J=8.9 Hz), 7.76 (1H, d, J=8.9 Hz), 8.29 (1H, s).

(5) Preparation of 2-(2-carboxyfuran-5-yl)-71-(4-fluorobenzyl)-5-methanesulfonyl-indole To a solution of the compound obtained in Example 29 (4) (0.0306 g) in 1,4-dioxane (0.5 ml), 10% lithium hydroxide aqueous solution (0.5 ml) was added at −5° C. under argon atmosphere and the mixture was stirred for 2 hours. To the reaction solution was then added 10% hydrochloric acid and the mixture was extracted with chloroform. The organic layer was washed with a saturated aqueous NaCl solution, dried over anhydrous magnesium sulfate, filtered and concentrated under reduced pressure to obtain 0.0285 g of the desired product as a white powder.

$^1$H-NMR (CDCl$_3$) δ: 3.11 (3H, s), 5.69 (2H, s), 6.67 (1H, d, J=3.6 Hz), 6.91-7.06 (4H, m), 7.16 (1H,s), 7.34 (1H, d, J=3.6 Hz), 7.49 (1H, d, J=8.9 Hz), 7.78 (1H, d, J=8.9 Hz), 8.32 (0.1H, s).

EXAMPLE 30

2-(2-Carboxyfuran-5-ylmethyl)-1-(4-fluorobenzyl)-5-methanesulfonylindole

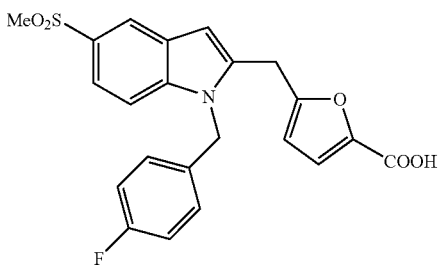

(1) Preparation of ethyl 5-formyl-2-furancarboxylate

To a solution of 5-formyl-2-furancarboxylic acid (0.5 g), in ethanol (35 ml), sulfuric acid (3.5 ml) was added at 0° C. and the mixture was heated under reflux for 5 hours. After cooling, the reaction solution was poured into water and extracted with ethyl acetate. The organic layer was washed with a saturated aqueous sodium hydrogencarbonate solution and water, dried over anhydrous magnesium sulfate, filtered and concentrated under reduced pressure. The resulting residue was separated using silica gel column chromatography (hexane:ethyl acetate=1:1) to obtain 0.5316 g of the desired product.

$^1$H-NMR (DMSO-$d_6$) δ: 1.31 (3H, t, J=7.2 Hz), 4.34 (2H, q, J=7.2 Hz), 7.47 (1H, d, J=3.6 Hz), 7.61 (1H, d, J=3.6 Hz), 9.74 (1H, s).

(2) Preparation of 1-benzenesulfonyl-2-(2-ethoxycarbonylfurtan-5-yl-hydroxymethyl)-5-methylthioindole To a solution of 1-benzenesulfonyl-5-methylthioindole (0.5178 g) in tetrahydrofuran (17 ml), n-butyl lithium (1.3 ml, 1.59 M) was added dropwise at −78° C. and the mixture was stirred for 30 minutes, followed by addition of the compound obtained in Example 30 (1) (0.3444 g), and the mixture was stirred at −50° C. for 40 minutes. The reaction solution was poured into a saturated aqueous ammonium chloride solution and extracted with ethyl acetate. The organic layer was washed with a saturated aqueous NaCl solution, dried over anhydrous magnesium sulfate, filtered and concentrated under reduced pressure. The resulting residue was separated using silica gel column chromatography (hexane:ethyl acetate=1:1) to obtain 0.593 g of the desired product.

$^1$H-NMR (CDCl$_3$) δ: 1.36 (3H, t, j=6.9 Hz), 2.46 (3H, s), 3.68 (1H, brs), 4.35 (2H, q, J=6.9 Hz), 6.44 (1H, s), 6.52 (1H, d, J=3.6 Hz), 7.14-7.56 (6H, m), 7.80 (2H, d, J=7.5 Hz), 7.96 (1H, d, J=8.9 Hz).

(3) Preparation of 1-benzenesulfonyl-2-(2-ethoxycarbonylfuran-5-yl-methyl)-5-methylthioindole To a solution of the compound obtained in Example 30 (2) (0.3586 g) in ethanol (8 ml), acetic acid (1 ml) and 10% palladium carbon (0.3586 g) were added and the mixture was stirred at 50° C. for 15 hours under hydrogen atmosphere. The reaction solution was filtered. The filtrate was concentrated under reduced pressure. The resulting residue was separated using silica gel column chromatography (hexane:ethyl acetate 1:1) to obtain 0.183 g of the desired product.

$^1$H-NMR (CDCl$_3$) δ: 1.36 (2H, t, J=7.2 Hz), 2.48 (3H, s), 4.35 (2H, q, J=7.2 Hz), 4.47 (2H, s), 6.24 (1H, d, J=3.3 Hz), 6.30 (1H, s), 7.09 (1H, d, J=3.3 Hz), 7.16-7.54 (5H, m), 7.69 (2H, d, J=8.5 Hz), 8.04 (1H, d, J=8.5 Hz).

(4) Preparation of 1-benzenesulfonyl-2-(2-ethoxycarbonylfuran-5-yl-methyl)-5-methanesulfonylindole To a solution of the compound obtained in Example 30 (3) (0.183 g) in a mixture of tetrahydrofuran (2 ml) and water (2 ml), OXONE (registered trademark) (0.4939 g) was added under ice-cooling and the mixture was stirred for 30 minutes and at 15 to 30° C. for 1.5 hours. A saturated aqueous sodium hydrogencarbonate solution was added thereto, and the mixture was extracted with ethyl acetate, dried over anhydrous magnesium sulfate, filtered and concentrated under reduced pressure. The resulting residue was separated using silica gel column chromatography (hexane:ethyl acetate=1:1) to obtain 0.1722 g of the desired product.

$^1$H-NMR— (CDCl$_3$) δ: 1.37 (3H, t, J=6.9 Hz), 3.06 (3H, s), 4.36 (2H, q, J=6.9 Hz), 4.52 (2H, s), 6.28 (1H, d, J=3.6 Hz), 6.46 (1H, s), 7.10 (1H, d, J=3.6 Hz), 7.46 (2H, t, J=7.9 Hz), 7.60 (1H, t, J=7.5 Hz), 7.75 (2H, d, J=7.2 Hz), 7.83 (1H, d, J=8.9 Hz), 8.04 (1H, s), 8.32 (1H, d, J=8.9 Hz).

(5) Preparation of 2-(2-ethoxycarbonylfuran-5-yl-methyl)-5-methanesulfonylindole To a solution of the compound obtained in Example 30 (4) (0.1722 g) in ethanol (14 ml), potassium hydroxide (0.047 g) was added and the mixture was stirred at 15 to 30° C. for 30 minutes. To the mixture was added 10% aqueous hydrochloric acid solution, and the mixture was extracted with ethyl acetate, dried over anhydrous magnesium sulfate, filtered and concentrated under reduced pressure. The resulting residue was separated using silica gel column chromatography (hexane:ethyl acetate=0.1:1) to obtain 0.07.48 g of the desired product.

$^1$H-NMR, (CDCl$_3$) δ: 1.37 (3H, t, J=7.2 Hz), 3.06 (3H, s), 4.24 (2H, s), 4.36 (2H, q, J=7.2 Hz), 6.27, (H, d, J=3.3 Hz), 6.51 (1H, s), 7.11 (1H, d, J=3.3 Hz), 7.45 (1H, d, J=8.5 Hz), 7.69 (1H, d, J=8.5 Hz), 8.18 (1H, s), 8.65 (1H, brs).

(6) Preparation of 2-(2-ethoxycarbonylfuran-5-yl-methyl)-1-(4-fluorobenzyl)-5-methanesulfonylindole To a solution of the compound obtained in Example 30 (5) (0.0592 g) in tetrahydrofuran (2 ml), 2.0 M lithium diisopropylamide solution (0.0852 ml) was added dropwise at −78° C. and the mixture was stirred for 30 minutes. 4-Fluorobenzyl bromide (0.02 ml) was then added to the mixture, followed by stirring at the same temperature for, 30 minutes. The reaction solution was poured into a saturated aqueous ammonium chloride solution and extracted with ethyl acetate. The organic layer was washed with a saturated aqueous NaCl solution, dried over anhydride magnesium sulfate, filtered and concentrated under reduced pressure. The resulting residue was separated using silica gel preparative thin-layer chromatography (hexane:ethyl acetate=1:1) to obtain 0.005 g of the desired product.

$^1$H-NMR (CDCl$_3$) δ: 1.36 (3H, t, J=6.9 Hz), 3.08 (3H, s), 4.15 (2H, s), 4.35 (2H, q, J=6.9 Hz), 5.34 (2H, s), 6.08 (1H, d, J=3.3 Hz), 6.60 (1H, s), 6.82-6.98 (4H, m), 7.03 (1H, d, J=3.3 Hz), 7.32 (1H, d, J=8.9 Hz), 7.70 (1H, d, J=8.5 Hz), 8.22 (1H, s).

(7) Preparation of 2-(2-carboxyfuran-5-yl-methyl)-1-(4-fluorobenzyl)-5-methanesulfonylindole To a solution of the compound obtained in Example 30 (6) (0.003 g) in 1,4-dioxane (0.5;ml), a 10% aqueous lithium hydroxide solution (0.5 ml) was added at −5° C. under argon atmosphere and the mixture was stirred for 2 hours. To the reaction solution was then added a 10% aqueous hydrochloric acid solution and the mixture was extracted with chloroform. The organic layer was washed with a saturated aqueous NaCl solution, dried over anhydrous magnesium sulfate, filtered and concentrated under reduced pressure. The resulting residue was separated using silica gel preparative thin-layer chromatography (chloroform:methanol=9:1) to obtain 0.001 g of the desired product.

$^1$H-NMR (CDCl$_3$) δ: 1.36 (3H, t; J=6.9 Hz), 3.08. (3H, s), 4.15 (2H, s), 4.35 (2H, q, J=6.9 Hz), 5.34 (2H, s); 6.16 (1H, d,

J=3.3 Hz), 6.60 (1H, s), 6.82-6.98 (4H, m), 7.16 (1H, d, J=3.3 Hz), 7.32 (1H, d, J=8.9 Hz), 7.70 (1H, d, J=8.5 Hz), 8.22 (1H, s).

EXAMPLE 31

1-(4-Fluorobenzyl)-5-methanesulfonyl-2-(4-pyridyl) indole

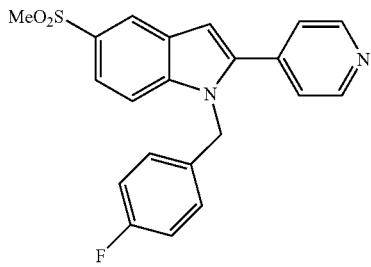

(1) Preparation of 5-methanesulfonyl-2-(4-pyridyl)-indole

To a mixture of 1-(4-methanesulfonyl-phenyl)-hydrazine hydrochloride (1.0 g) and polyphosphoric acid (15 g), 4-acetylpyridine (0.47 ml) was added and the mixture was stirred at 150° C. for 1 hour. The reaction solution was poured into a saturated aqueous sodium hydrogencarbonate solution and extracted with chloroform. The organic layer was concentrated under reduced pressure. The resulting residue was washed with n-hexane to obtain 0.9591 g of the desired product as a white solid.

$^1$H-NMR (DMSO-$d_6$) δ: 3.19 (3H, s), 7.43 (1H, s), 7.65 (1H, d, J=5.9 Hz), 7.70 (1H, d, J=5.9 Hz), 7.87 (2H, d, J=5.6 Hz), 8.21 (1H, s), 8.67 (2H, d, J=5.6 Hz).

(2) Preparation of 1-(4-fluorobenzyl)-5-methanesulfonyl-2-(4-pyridyl)indole

To a solution of the compound obtained in Example 31 (1) (0.4 kg) in N,N-dimethylformamide (160 ml), 60% sodium hydride (0.065 g) was added at 0° C. under nitrogen atmosphere and the mixture was stirred for 20 minutes, followed by addition of 4-fluorobenzyl bromide (0.2 ml), and the mixture was stirred at 15 to 30° C. for 15 hours. The reaction solution was then poured into water and extracted with ethyl acetate. The organic layer was washed with a saturated aqueous NaCl solution, dried over anhydrous magnesium sulfate, filtered and concentrated under reduced pressure. The resulting residue was separated using silica gel column chromatography (hexane:ethyl acetate=1:3) to obtain 0.3882 g of the desired product.

$^1$H-NMR (CDCl$_3$) δ: 3.10 (3H, s), 5.42 (2H, s), 6.88-7.05 (5H, m), 7.30-7.38 (3H, m), 7.74 (1H, d, J=10.5 Hz), 8.34 (1H, s), 8.66 (2H, d, J=5.9 Hz).

EXAMPLE 32

1-(4-Fluorobenzyl)-5-methanesulfonyl-2-(1-oxy-4-pyridyl) indole

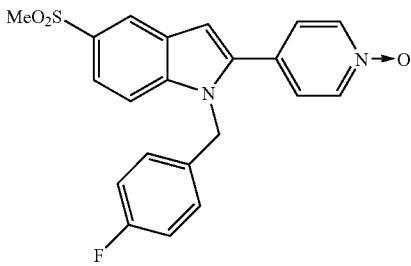

To a solution of 1-(4-fluorobenzyl)-5-methanesulfonyl-2-(4-pyridyl)indole (0.1975 g) in chloroform (20 ml), m-chloroperbenzoic acid (0.1688 g, 80% purity) was added and the mixture was stirred at 15 to 30° C. for 3 days. The reaction solution was poured into water and extracted with chloroform. The organic layer was washed with a saturated aqueous sodium hydrogencarbonate solution, dried over anhydrous magnesium sulfate, filtered and concentrated tinder reduced pressure. The resulting residue was separated using silica gel column chromatography (chloroform:methanol=9:1) to obtain 0.150 g of the desired product.

$^1$H-NMR (CDCl$_3$) δ: 3.10 (3H, s), 5.40 (2H, s), 6.90-7.06 (5H, m), 7.27-7.38 (3H, m), 7.78 (1H, d, J=8.5 Hz), 8.21 (2H, d, J=7.2 Hz), 8.33 (1H, s).

EXAMPLE 33

1-(4-Fluorobenzyl)-5-methanesulfonyl-2-([1,3,4] oxadiazol-2-yl)-1H-pyrrolo[2,3-b]pyridine

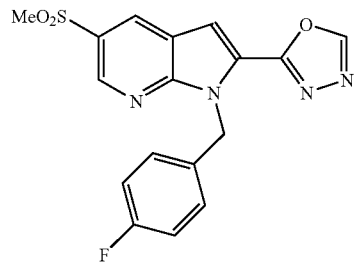

(1) Preparation of. 1-benzenesulfonyl-2-trimethylsilyl-5-methylthio-1H-pyrrolo[2,3-b]pyridine A mixture of trimethylsilylacetylene (0.41 g), 2-benzenesulfonylamino-3-iodo-5-methylthiopyridine (0.82 g), triethylamine (0.42 g), cuprous iodide (30 mg), dichlorobis (triphenylphosphine) palladium. (75 mg) and dioxane (2 ml) was stirred at 70° C. for 16 hours under nitrogen atmosphere. To the reaction solution were then added water and ethyl acetate. The insolubles were filtered off. To the filtrate was added a saturated aqueous sodium hydrogencarbonate solution, and the mixture was extracted with ethyl acetate, dried over anhydrous sodium sulfate, filtered and concentrated. The resulting residue was subjected to silica gel column chromatography (hexane:ethyl acetate=10:1) to obtain 0.61 g of the desired product.

$^1$H-NMR (CDCl$_3$) δ: 0.51 (9H, s), 2.46, (3H, s), 6.78 (1H, s), 7.42-7.58 (3H, m), 7.75 (1H, d, J=2.0 Hz), 8.10-8.14 (2H, m), 8.33 (1H, d, J=2.0 Hz).

(2) Preparation of 1-benzenesulfonyl-5-methylthio-1H-pyrrolo[2,3-b]pyridine

A mixture of 1-benzenesulfonyl-2-trimethylsilyl-5-methylthio-1H-pyrrolo[2,3-b]pyridine obtained in Example 33 (1) (0.60 g), tetrabutylammonium fluoride/tetrahydrofuran solution (1.0 M, 0.8 ml) and tetrahydrofuran (100 ml) was stirred under nitrogen atmosphere at −25° C. for 30 minutes. To the reaction solution was added a saturated aqueous ammonium chloride solution, and the mixture was extracted with ethyl acetate, dried over anhydrous sodium sulfate, filtered and concentrated. The resulting residue was subjected to silica gel column chromatography (hexane:ethyl acetate=5:1) to obtain 0.40 g of the desired product.

$^1$H-NMR (CDCl$_3$) δ: 2.49 (3H, s), 6.54 (1H, d, J=4.0 Hz), 7.45-7.62 (3H, m), 7.71 (1H, d, J=4.0 Hz), 7.80 (1H, d, J=2.0 Hz), 8.15-8.20 (2H, m)>8.39 (1H, d, J=2.0 Hz).

(3) Preparation of 1-benzenesulfonyl-5-methylthio-1H-pyrrolo[2,3-b]pyridine-2-carboxylic acid methyl ester To a mixture of 1-benzenesulfonyl-5-methylthio-1H-pyrrolo[2,3-b]pyridine obtained in Example 33 (2) (0.80 g) and tetrahydrofuran (30 ml), a lithium diisopropylamide (5.81 mmol) solution in tetrahydrofuran was added dropwise at −78° C. under nitrogen atmosphere, and the mixture was heated to −30° C. and stirred for 20 minutes, followed by dropwise addition of a mixture of dimethyl carbonate (0.91 g) and tetrahydrofuran (2 ml) at −78° C., and the mixture was stirred at −78° C. for 6 hours. To the reaction solution was added a saturated aqueous ammonium chloride solution, and the mixture was extracted with ethyl acetate, dried over anhydrous sodium sulfate, filtered and concentrated. The resulting residue was subjected to silica gel column chromatography (hexane ethyl acetate=1:1) to obtain 0.54 g of the desired product.

$^1$H-NMR (CDCl$_3$) δ: 2.51 (3H, s), 3.99 (3H, s), 6.98 (1H, s), 7.52-7.68. (3H, m), 7.83 (1H, d, J=2.3 Hz), 8.37-8.42 (2H, m), 8.53 (1H, d, J=2.3 Hz).

(4) Preparation of 1-benzenesulfonyl-5-methanesulfonyl-1H-pyrrolo[2,3-b]pyridine-2-carboxylic acid methyl ester A mixture of 1-benzenesulfonyl-5-methylthio-1H-pyrrolo[2,3-b]pyridine-2-carboxylic acid methyl ester obtained in Example 33 (3) (0.18 g), m-chloroperbenzoic acid (0.24 g) and dichloromethane (10 ml), was stirred at 15 to 30° C. for 1 hour under nitrogen atmosphere. To the reaction solution was added a saturated aqueous sodium hydrogencarbonate solution, and the mixture was extracted with dichloromethane, dried over anhydrous sodium sulfate, filtered and concentrated. The resulting residue was subjected to silica gel column chromatography (hexane:ethyl acetate 1:1) to obtain 0.19 g of the desired product.

$^1$H-NMR (CDCl$_3$) δ: 3.13 (3H, 5), 4.04 (3H, s), 7.12 (1H, 5s), 7.57-7.73 (3H, m), 8.44-8.51 (3H, m), 9.09 (1H, d, J=2.3° Hz).

(5) Preparation of 1-(4-fluorobenzyl)-5-methanesulfonyl-1H-pyrrolo[2,3-b]pyridine-2-carboxylic acid methyl ester A mixture of 1-benzenesulfonyl-5-methanesulfonyl-1H-pyrrolo[2,3-b]pyridine-2-carboxylic acid methyl ester obtained in Example 33 (4) (0.19 g), potassium hydroxide (90 mg) and methanol (20 ml) was stirred at 15 to 30° C. for 1 hour under nitrogen atmosphere. To the reaction solution was added water and the mixture was neutralized with hydrochloric acid. The precipitated crystal was filtered off. To the resulting crude crystal were added sodium hydride (16 mg), 0.4-fluorobenzyl bromide (80 mg) and N,N-dimethylformamide (5 ml) and the mixture was stirred at 15 to 30° C. for 1 hour. To the reaction solution was then added water and the mixture was neutralized with hydrochloric acid. The precipitated crystal was filtered off. There were obtained 110 mg of the desired product as a crystal.

$^1$H-NMR (CDCl$_3$) δ: 3.17 (3H, s), 3.93 (3H, s), 5.99 (2H, s), 6.90-6.98 (2H, m), 7.24-7.30 (2H, m), 7.41 (1H, s), 8.62 (1H, d, J=2.0 Hz), 9.02 (1H, d, J=2.0 Hz).

(6) Preparation of 1-(4-fluorobenzyl)-5-methanesulfonyl-2-([1,3,4]oxadiazol-2-yl)-1H-pyrrolo[2,3-b]pyridine To a solution of 1-(4-fluorobenzyl)-5-methanesulfonyl-1H-pyrrolo[2,3-b]pyridine-2-carboxylic acid methyl ester obtained in Example 33 (5) (0.3 g) in ethanol (9 ml), hydrazine monohydrate (0.22 g) was added at 15 to 30° C. and the mixture was heated under reflux for 6 hours, followed by further addition of hydrazine monohydrate (0.11 g), and the mixture was heated under reflux for 4 hours. Furthermore, hydrazine, monohydrate (0.1 g) was added to the mixture, followed by heating under reflux for 16 hours. The reaction solution was concentrated under reduced pressure. To the resulting crude product was added orthoformic acid triethyl ester (25 ml) and the mixture was heated under reflux for 18 hours. The reaction solution was separated using silica gel column chromatography (ethyl acetate:hexane=1:1) to obtain 220 mg of the desired product.

$^1$H-NMR (DSMO-d$_6$) δ: 3.15 (3H, s) 6.07 (2H, s), 7.09 (2H, t, J=8.9 Hz) 7.22 (2H, dd, J=5.6, 8.9 Hz), 7.65 (1H, s) 8.80 (1H, d, J=2.3 Hz), 8.97 (1H, d, J=2.3 Hz), 9.47 (1H, s).

EXAMPLE 34

5-(4-Fluorobenzyl)-2-methanesulfonyl-6-(thiazol-2-yl)-5H-pyrrolo[2,3-b]pyrazine

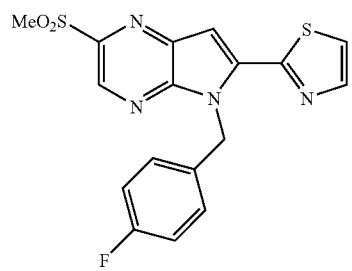

(1) Preparation of 2-amino-5-methylthiopyrazine

A suspension of 2-amino-5-bromopyrazine (100 mg), 95% methanethiol sodium salt (84.8 mg) and tetrakistriphenylphosphine palladium (66.4 mg) in N,N-dimethylformamide (2.9 ml) was stirred at 60° C. for 15 hours. After completion of the reaction, the reaction solution was poured into a saturated aqueous sodium hydrogencarbonate solution, extracted with toluene, washed with a saturated aqueous NaCl solution, dried over anhydrous sodium sulfate, filtered and concentrated. The resulting residue was separated using silica gel column chromatography. (ethyl acetate:hexane 1:2) to obtain 67.8 mg (84%) of the desired product as a white powder.

H-NMR (CDCl$_3$) δ: 2.52 (3H, s), 4.42 (2H, brs), 7.91 (1H, d, J=1.2 Hz), 7.98 (1H, d, J=1.2 Hz).

(2) Preparation of 2-amino-3-bromo-5-methylthiopyrazine

To a solution of the compound obtained in Example 34 (1) (100 mg) in chloroform (18 ml), pyridine (56.0 mg) was added and then a solution of bromine (113 mg) in chloroform (18 ml) was added dropwise at 15 to 30° C. over 1 hour under light-shielding and the mixture was stirred at the same temperature for 30 minutes. After completion of the reaction, the reaction solution was washed with water, dried over anhydrous sodium sulfate, filtered and concentrated. The resulting residue was separated using silica gel column chromatography (ethyl acetate:hexane=1:4) to obtain 112 g (72%) of the desired product as a white powder.

H-NMR (CDCl$_3$) δ: 2.52 (3H, s), 4.90 (2H, brs), 7.91 (1H, s).

(3) Preparation of 3-(2-amino-5-methylthiopyrazin-3-yl)-2-propyn-1-ol

To a solution of the compound obtained in Example 34 (2) (440 mg) in dioxane (10 ml), 2-propyn-1 ol (168 mg), bis-triphenylphosphine palladium dichloride (72 mg), copper(I) iodide (38 mg) and triethylamine (304 mg) were added successively and the mixture was stirred in a sealed tube at 70° C. for 2 hours. After cooling, the reaction solution was poured into water, and the mixture was extracted with chloroform, dried over anhydrous magnesium sulfate, filtered and concentrated. The resulting residue was separated using silica gel column chromatography (chloroform:methanol 10:1) to obtain 347 mg (88.9%) of the desired product as a brown oil.

$^1$H-NMR (CDCl$_3$) δ: 2.53 (3H, s), 4.57 (2H, s), 4.90 (2H, brs), 7.95° (1H, s).

(4) Preparation of (2-methylthio-5H-pyrrolo[2,3-b]pyrazin-6-yl)methanol

To a solution of the compound obtained in Example, 34 (3) (381 mg) in N,N-dimethylformamide (110 ml), copper(I) iodide (111 mg) was added and the mixture was stirred at –109 150° C. for 2 hours. The reaction solution was poured into water, and the mixture was extracted with chloroform, washed with water, dried over magnesium sulfate and concentrated under reduced pressure. The resulting residue was separated using silica gel preparative thin-layer chromatography (chloroform:methanol=20:1) to obtain 155 mg (40.7%) of the desired product as a yellow powder.

$^1$H-NMR (CDCl$_3$) δ: 2.65 (3H, s), 4.93 (2H, s), 6.48 (1H, s), 8.12 (1H, s).

(5) Preparation of 2-methylthio-5H-pyrrolo[2,3-b]pyrazine-6-carbaldehyde

To a solution of the compound obtained in Example 34 (4) (123 mg) in acetone (40 ml), manganese dioxide (1.86 g) was added and the mixture was stirred at –15 to 30° C. for-1 hour. The reaction solution was filtered through Celite and concentrated under reduced pressure to obtain 60 mg (49.3%) of the desired product as a yellow powder.

$^1$H-NMR (CDCl$_3$) δ: 2.67 (3H, s), 7.31 (1H, s), 8.37 (1H, s), 9.96 (1H, 5).

(6) Preparation of 5-(4-fluorobenzyl)-2-methylthio-5H-pyrrolo[2,3-b]pyrazine-6-carbaldehyde To a solution of the compound obtained in Example 34 (5) (10 mg) in N,N-dimethylformamide (0.5 ml), 60% sodium hydride (3 mg) was added at 0° C. and the mixture was stirred for 20 minutes. To the resulting mixture was added dropwise 4-fluorobenzyl bromide (15 mg) and the mixture was stirred at 15 to 30° C. for 30 minutes. The reaction solution was poured into a saturated aqueous ammonium chloride solution, extracted with chloroform, washed with water, dried over magnesium sulfate and concentrated under reduced pressure. The resulting residue was separated using silica gel preparative thin-layer chromatography (hexane:ethyl acetate=5:1) to obtain 15 mg (99.6%) of the desired product as an orange powder.

$^1$H-NMR (CDCl$_3$) δ: 2.66 (3H, s), 5.84 (2H, s), 6.93 (2H, t, J=8.6 Hz), 7.27-7.33 (3H, m), 8.36 (1H, s), 9.96 (1H, s).

(7) Preparation of 5-(4-fluorobenzyl)-2-methylthio-5H-pyrrolo[2,3-b]pyrazine-6-carboxylic acid methyl ester To the compound obtained in Example 34 (6) (15 mg), methanol (2.8 ml), manganese dioxide (22 mg) and sodium cyanide (13 mg) were added at 0° C. and the mixture was stirred at 15 to 30° C. for 15 hours. The reaction solution was then filtered through Celite, extracted with chloroform, washed with water, dried over magnesium sulfate and concentrated under reduced pressure. The resulting residue was separated using silica gel preparative thin-layer chromatography (chloroform:methanol=100:1) to obtain 11 mg (66.4%) of the desired product as a white powder.

$^1$H-NMR (CDCl$_3$) δ: 2.66 (3H, s), 3.91 (3H, s), 5.88 (2H, s), 6.93 (2H, t, J=8.9 Hz), 7.20-7.25 (2H, m), 7.32 (1H, s), 8.30 (1H, s).

(8) Preparation of 5-(4-fluorobenzyl)-2-methanesulfonyl-5H-pyrrolo[2,3-b]pyrazine-6-carboxylic acid methyl ester To a suspension of the compound obtained in Example 34 (7) (1.06 g) in tetrahydrofuran (40 ml), methanol (40 ml) and water (20 ml), OXONE. (2.16 g) was added at 0° C. and the mixture was stirred at 15 to 30° C. for 4 hours. Further, OXONE (1.08 g) was added thereto and the mixture was stirred at 15 to 30° C. for 1 hour. After completion of the reaction, the reaction solution was concentrated and poured into a saturated aqueous sodium hydrogencarbonate solution. The mixture was extracted with ethyl acetate, washed with a saturated aqueous NaCl solution, dried over anhydrous magnesium sulfate, filtered and concentrated. The resulting residue was then separated using silica gel column chromatography (ethyl acetate:hexane=1':2 and 2:1) to obtain 852 mg (73%) of the desired product as a pale yellow crystal.

H-NMR (CDCl$_3$) δ: 3.32 (3H, s), 3.98 (3H,s), 5.98 (2H,s), 6.96 (2H, t, J=8.5 Hz), 7.2-7.4 (2H, m), 7.52 (1H, s), 9.19 (1H, s).

(9) Preparation of 5-(4-fluorobenzyl)-2-methane-sulfonyl-5H-pyrrolo[2,3-b]pyrazine-6-thioamide To a solution of 5-(4-fluorobenzyl)-2-methanesulfonyl-5H-pyrrolo[2,3-b]pyrazine-6-carboxylic acid methyl ester obtained in Example 34 (8) (0.31 g) in dioxane (7 ml), 30% aqueous potassium hydroxide solution (7 ml) was added at 15 to 30° C. and the mixture was stirred at 80° C. for 30 minutes. Ice-water and hydrochloric acid, were added thereto. The resulting crystal was filtered off. The mixture of the resulting crystal (0.11 g) and thionyl chloride (1 ml), was stirred at 70° C. for 5 hours. Toluene was added thereto and the reaction solution was concentrated. An ammonia gas was blown into a solution of the resulting residue in tetrahydrofuran (30 ml) at 15 to 30° C. The reaction solution was concentrated, diluted with ethyl acetate, washed with water and dried. The solvent was distilled off under reduced pressure. To the mixture of the resulting residue (0.15 g), benzene (3 ml) and tetrahydrofuran (2 ml) was added Lawesson's reagent at 15 to 30° C. and stirred at 70° C. for 3 hours. The reaction solution was separated using silica gel column chromatography (hexane:ethyl acetate=1:1) to obtain the desired product (90 mg).
$^1$H-NMR (CDCl$_3$) δ: 3.26 (3H, s), 6.09 (2H, s), 6.93 (2H, t, J=8.9 Hz), 7.00 (1H, s), 7.20 (2H, dd, J=5.3, 8.9 Hz), 7.40 (1H, brs), 7.70 (1H, brs), 9.08 (1H, s).

(10) Preparation of 5-(4-fluorobenzy)-2-methane-sulfonyl-6 -(thiazol-2-yl)-5H-pyrrolo[2,3-b]pyrazine A mixture of 5-(4-fluorobenzyl)-2-methanesulfonyl-5H-pyrrolo[2,3-b]pyrazine-6-thioamide (90 mg), bromoacetaldehyde dimethylacetal (0.06 ml), p-toluenesulfonic acid (4 mg) and acetic acid (1 ml) was stirred at 100° C. for 1.5 hours. The reaction solution was separated using silica gel column chromatography (hexane:ethyl acetate=0.2:1).to obtain the desired product (30 mg).
$^1$H-NMR (CDCl$_3$) δ: 3.30 (3H, s), 6.19 (2H, s), 6.89 (2H, t, J=8.9 Hz), 7.23 (2H, dd. J=5.3, 8.9 Hz), 7.25 (1H, s), 7.55 (1H, d, J=3.0 Hz), 8.04 (1H, d, J=3.0 Hz), 9.08 (1H, s).

EXAMPLE 35

5-(4-Fluorobenzyl)-2-methanesulfonyl-6-(oxazol-2-yl)-5H-pyrrolo[2,3-b]pyrazine

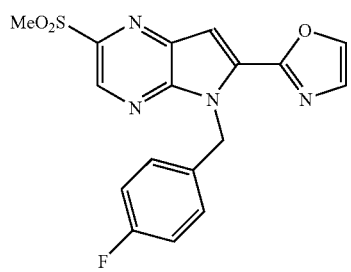

To a solution of 5-(4-fluorobenzyl)-2-methanesulfonyl-5H-pyrrolo[2,3-b]pyrazine-6-carboxylic acid methyl ester (0.31 g) in dioxane (7 ml), 30% aqueous potassium hydroxide solution (7 ml) was added at 15 to 30° C. and the mixture was stirred at 80° C. for 30 minutes. Ice-water and hydrochloric acid were added thereto to collect the resulting crystal by filtration. The mixture of the resulting crystal (0.11 g) and thionyl chloride (1 ml) was stirred at 70° C. for 5 hours. Toluene was added thereto and the reaction solution was concentrated. A solution of the resulting crude product and 2-trimethylsilyl-1H-1,2,3-triazole (45 mg) in toluene (5 ml) was heated under reflux for 40 hours. The mixture was diluted with ethyl acetate, washed with water and dried. The solvent was distilled off under reduced pressure. The resulting residue was separated using silica gel column chromatography (hexane:ethyl acetate=1:1) to obtain the desired product (66 mg).
$^1$H-NMR (CDCl$_3$) δ: 3.31 (3H, s), 6.18 (2H, s), 6.93 (2H, t, J=8.9 Hz), 7.35 (2H, dd, J=5.3, 8.9 Hz), 7.41 (1H, d, J=0.7 Hz), 7.44 (1H, s), 7.85 (1H, d, J=0.7 Hz), 9.10 (1H, s).

EXAMPLE 36

1-(4-Fluorobenzyl)-5-methanesulfonyl-2-(5-fluoro-pyrimidin-4-yl)-1H-pyrrolo[2,3-b]pyridine

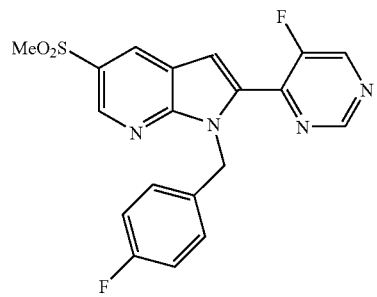

(1) Preparation of (1-(4-fluorobenzyl)-5-methane-sulfonyl-1H-pyrrolo[2,3-b]pyridin-2-yl)methanol To a mixture of 1-(4-fluorobenzyl)-5-methanesulfonyl-1H-pyrrolo[2,3-b]pyridine-2-carboxylic acid methyl ester (0.49 g) and tetrahydrofuran (14 ml), lithium aluminum hydride (77 mg) was added at 0° C. and the mixture was stirred at the same temperature for 15 minutes. The mixture was diluted with ethyl acetate and a saturated aqueous NaCl solution was added thereto. The mixture was dried over sodium sulfate and concentrated under reduced pressure. The resulting residue was separated using silica gel column chromatography (hexane:ethyl acetate=1:1) to obtain the desired product (0.39 g) as a white powder.
$^1$H-NMR (Acetone-d$_6$) δ: 3.20 (3H, s), 4.63 (1H, t, J=5.3 Hz), 4.7.9 (2H, d, J=5.3 Hz), 5.72 (2H, s), 6.73 (1H, s), 7.07 (2H, t, J=80.9 Hz), 7.25-7:31 (2H, m), 8.248: (1, (1H, d J=2.0 Hz), 8.77 (1H, d, J=2.0 Hz).

(2) Preparation of (1-(4-fluorobenzyl)-5-methane-sulfonyl-1 H-pyrrolo[2,3-b]pyridin-2-yl)carbaldehyde To a mixture of (1-(4-fluorobenzyl)-5-methanesulfonyl-1H-pyrrolo[2 3-b]pyridin-2-yl)methanol obtained in Example 36 (1) (0.39 g) and acetone (11 ml), manganese dioxide (816 mg) was added at 15 to 30° C. and the mixture was stirred at 15 to 30° C. for 0.2 hours. Manganese dioxide was filtered through Celite and the resulting filtrate was concentrated under reduced pressure to obtain the desired product (0.37 g) as a yellowish-white powder.
$^1$H-NMR (Acetone-d$_6$) δ: 3.27 (3H, s), 5.97 (2H, s), 7.04 (2H, t, J=6.9 Hz), 7.34-7.40 (2H, m), 7.76 (1H, s), 8.83 (1H, d, J=2.3 Hz), 9.05 (1H, d, J=2.3 Hz), 10.08 (1H, s).

(3) Preparation of 2-fluoro-3-(1-(4-fluorobenzyl)-5-methanesulfonyl-1H-pyrrolo[2,3-b]pyridin-2-yl)-3-oxopropionic acid ethyl ester A mixture of (1-(4-flubrobenzyl)-5-methanesulfonyl-1 H-pyrrolo[2,3-b]pyridin-2-yl)carbaldehyde obtained in Example 36 (2) (100 mg), ethyl bromofluoroacetate (0.05 ml), zinc-powder (28 mg) and tetrahydrofuran (3 ml) was heated under reflux for 15 minutes. The mixture was diluted with ethyl acetate, washed with a saturated aqueous sodium hydrogencarbonate solution, water and a saturated aqueous NaCl solution successively, dried and concentrated under reduced pressure. The resulting residue was separated using silica gel column chromatography (hexane:ethyl acetate=1:2) to obtain 2-fluoro-3-(1-(4-fluorobenzyl)-5-methanesulfonyl-1H-pyrrolo[Z, 3-b]pyridin-2-yl)-3-hydroxypropionic acid ethyl ester (100 mg) in a yellow amorphous form. To a mixture of the resulting 2-fluoro-3-(1-(4-fluorobenzyl)-5-methanesulfonyl-1H-pyrrolo[2,3-b]pyridin-2-yl)-3-hydroxypropionic acid ethyl ester (90 mg) and dichloromethane (2 ml) was added Dess Martin reagent (190 mg) at 15 to 30° C. and the mixture was stirred at the same temperature for 30 minutes. The mixture was diluted with ethyl acetate, washed with 5% aqueous sodium thiosulfate solution, a saturated aqueous sodium hydrogencarbonate solution, water and a saturated aqueous NaCl solution successively, dried and concentrated under reduced pressure. The resulting residue was separated using silica gel column chromatography (hexane ethyl acetate=1:1) to obtain the desired product (80 mg) in a white amorphous form.
$^1$H-NMR (CDCl$_3$) δ: 1.20 (3H, t, J=7.3 Hz), 3.17 (3H, s), 4.18-4.32 (2H, m), 5.71 (1H, d, J=48.8 Hz), 5.98 (2H, dd, 14.8, 17.8 Hz), 6.93 (2H, t, J=8.9 Hz), 7.22-7.27 (2H, m), 8.70 (1H, d, J=2.0 Hz), 9.10 (1H, d, J=2.0 Hz).

(4) Preparation of 5-fluoro-6-(1-(4-fluorobenzyl)-5-methanesulfonyl-1H-pyrrolo[2,3-b]pyridin-2-yl)-3H-pyrimidin-4-one To a mixture of 2-fluoro-3-(1-(4-fluorobenzyl)-5-methanesulfonyl-1H-pyrrolo[2,3-b]pyridin-2-yl)-3-oxopropionic acid ethyl ester obtained in Example 36 (3) (88 mg), formamidine acetate (42 mg) and methanol (1.2 ml), sodium methoxide (0.6 ml, 1 mol/l solution in methanol) was added at 15 to 30° C. and the mixture was stirred at the same temperature for 18 hours. The mixture was neutralized with acetic acid and diluted with ethyl acetate. The organic layer was washed with water, dried and concentrated under reduced pressure. The resulting residue was separated using silica gel column chromatography (methanol:dichloromethane=5:95) to obtain the desired product (23 mg) in a white amorphous form.
$^1$H-NMR (Acetone-d$_6$) δ: 2.60-3.05 (1H, brs), 3.25 (3H, s), 6.09 (2H, s), 6.97 (2H, t, J=8.9 Hz), 7.14-7.20 (2H, m), 7.32 (1H, d, J=:2.6 Hz), 8.28 (1H, s), 8.68 (1H, d, J=2.0 Hz), 8.91 (1H, d, J=2.0 Hz).

(5) Preparation of 1-(4-fluorobenzyl)-5-methanesulfonyl-2-(6-chloro-5-fluoropyrimidin-4-yl)-1H-pyrrolo[2,3-b]pyridine A mixture of 5-fluoro-6-(1-(4-fluorobenzyl)-5 methanesulfonyl-1H-pyrrolo[2,3-b]pyridin-2-yl)-3H-pyrimidin-4-one obtained in Example 36 (4) (20 mg) and phosphorus oxychloride (1 ml) was heated, under reflux for 3 hours. The mixture was concentrated under reduced pressure, diluted with dichloromethane, washed with water, dried and concentrated under reduced pressure. The resulting residue was separated using silica gel column chromatography (methanol:dichloromethane=1:99) to obtain the desired product (13 mg) as a white powder.
$^1$H-NMR (CDC1$_3$) δ: 3.18 (3H, s), 6.24 (2H, s), 6.87 (2H, t, J=8.6 Hz), 6.96-7.03 (2H, m), 8.64 (1H, d, J=2.0 Hz), 8.82 (1H, s), 9.02 (1H, d, J=2.0 Hz).

(6) Preparation of 1-(4-fluorobenzyl)-5-methanesulfonyl-2-(5-fluoropyrimidin-4-yl)-1H-pyrrolo[2,3-b]pyridine A mixture of 1-(4-fluorobenzyl)-5-methanesulfonyl-2-(6-chloro-5-fluoropyrimidin-4-yl)-1H-pyrrolo[2,3-b]pyridine obtained in Example 36 (5) (12 mg), ethanol (1 ml), ethyl acetate (1 ml) and 10% palladium on carbon (10 mg) was stirred under hydrogen stream at 15 to 30° C. for 1.5 hour. The catalyst was filtered through Celite. The filtrate was concentrated under reduced pressure. The resulting residue was separated using silica gel column chromatography (methanol:dichloromethane=1:99) to obtain the desired product (9 mg) as a white powder.
$^1$H-NMR (CDCl$_3$) δ: 3.18 (3H, s), 6.27 (2H, s), 6.85 (2H, t, J-8.6 Hz), 6.98-7.04 (2H, m), 7.49 (1H, d, J=3.0 Hz), 8.62 (1H, d, J=2.3 Hz), 8.68 (1H, d, J=3.0 Hz), 9.01 (1H, d, J=2.3 Hz), 9.08 (1H, d, J=3.0 Hz).

EXAMPLE 37

1-(2,4-Difluorobenzyl)-5-methanesulfonyl-2-([1,3,4] oxadiazol-2-yl)-1H-pyrrolo[2,3-b]pyridine

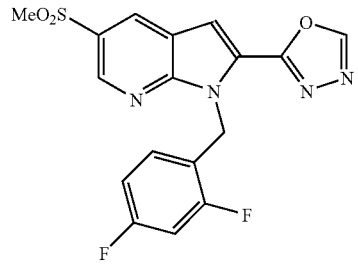

(1) Preparation of 1-(2,4-difluorobenzyl)-5-methanesulfonyl-1H-pyrrolo[2,3-b]pyridine-2-carboxylic acid methyl ester The procedures, were carried out in a similar manner to those in Example 33 (5) replacing 4-fluorobenzyl bromide with 2,4-difluorobenzyl bromide to obtain the desired product as a yellow crystal.
$^1$H-NMR (CDCl$_3$) δ: 3.16 (3H, s), 3.91 (3H, s), 6.04 (2H, s), 6.65-6.70 (2H, m)., 6.78-6.86 (1H, m), 7.45 (1H, s), 8.64 (1H, d, J=2.3 Hz), 9.00 (1H, d, J=2.3 Hz).

(2) Preparation of 1-(2,4-difluorobenzyl)-5-methanesulfonyl-2-([1,3,4]oxadiazol-2-yl)-1H-pyrrolo[2,3-b] pyridine The procedures were carried out in a similar manner to those in Example 33 (6) replacing 1-(4-fluorobenzyl)-5-methanesulfonyl-1H-pyrrolo[2,3-b]pyridine-2-carboxylic acid methyl ester with 1-(2,4-difluorobenzyl)-5-methanesulfonyl-1H-pyrrolo[2,3-b]pyridine-2-carboxylic acid methyl ester to obtain the desired product as a white crystal.

$^1$H-NMR (CDCl$_3$) δ: 3.17 (3H, s), 6.23 (2H, s), 6.60-6.83 (3H, m), 7.44 (1H, s), 8.52 (1H, s), 8.64 (1H, d, J=2.0 Hz), 8.99 (1H, d, J=2.0 Hz).

Test Example 1

Method for Measuring Inhibitory Activity Against Human COX-1 and COX-2 using Peripheral Blood 1 μl of a solution of the compound of the present invention in DMSO was added to 500 μl of peripheral blood collected from a healthy volunteer.

In the case of measuring COX-1 activity, after incubating at 37° C. for 4.5 hours, calcium ionophore A23187 was added to a final concentration of 500 μM followed by additional incubation at 37° C. for 30 minutes and transferring to ice to stop the reaction.

In the case of measuring COX-2 activity, LPS (*E. coli* 026:B6) was added onto blood to which the compound had been addded to a concentration of 10 gg/ml followed by incubating at 37° C. for 5 hours and transferring onto ice to stop the reaction.

After centriifuging (150G×10 minutes), the amount of thromboxane B2 contained in the supernatant was measured with a thromboxane B2 EIA.kit (Cayman), and the concentration at which 50% inhibitory activity is demonstrated was indicated below as the IC$_{50}$ value by taking the value of the solvent control (prepared by performing the same procedure as above but not adding the compound) to be 100%.

TABLE 1

| Example Compound | IC$_{50}$ COX-2 | COX-1 |
|---|---|---|
| 1 | 0.15 μM | >20 μM |
| 2 | 0.5 μM | >20 μM |
| 3 | 0.3 μM | >20 μM |
| 4 | 4 μM | >20 μM |
| 5 | 0.4 μM | >20 μM |
| 7 | 1.5 μM | >20 μM |
| 8 | 0.8 μM | >20 μM |
| 9 | 2 μM | >20 μM |
| 10 | 1.5 μM | >20 μM |
| 11 | 0.2 μM | >20 μM |
| 12 | 0.15 μM | >20 μM |
| 13 | 4 μM | >10 μM |
| 14 | 0.1 μM | >20 μM |
| 17 | 0.8 μM | >20 μM |
| 33 | 0.2 μM | >20 μM |

INDUSTRIAL APPLICABILITY

The present invention provides a compound which has COX-2 inhibitory action and is useful as a pharmaceutical, such as an anti-inflammatory drug.

What is claimed is:

1. A compound according to formula (1):

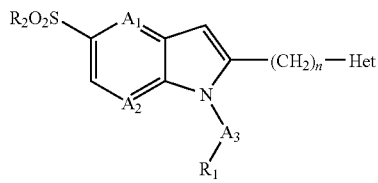

Wherein Het represents an optionally substituted heterocyclic group selected from the group consisting of oxetane, furan, dihydrofuran; tetrahydrofuran; pyran; dihydropyran; tetrahydropyran; dioxole; thiophene; dihydrothiophene; tetrahydrothiophene; thiopyran; dihydrothiopyran; tetrahydrothiopyran; pyrrole; dihydropyrrole; pyrrolidine; pyridine; dihydropyridine; tetrahydropyridine; piperidine; pyrazole; 2-pyrazoline; pyrazolidine; imidazole; imidazolidine; pyrimidine; pyrazine; oxazoline; piperazine; 1,2,3-triazole; 1,2,4-triazole; tetrazole; isoxazole; 1,3-oxadiazole; 1,2,3-oxadiazole; 1,2,4-oxadiazole; 1,2,5-oxadiazole; 1,3,4-oxadiazole; 1,2-thiazole; 1,3-thiazole; 1,2,3-thiadiazole; 1,2,4-thiadiazole; 1,2,5-thiadiazole; 1,3,4-thiadiazole; 1,3-dioxolan, oxazolidine, and morpholine;

Wherein A$^1$ and A$^2$ each represents —N═;

A$^3$ represents —CH$_2$—, —(C═O)—, or —SO$_2$—;

R$^1$ represents a group selected from the following formulae:

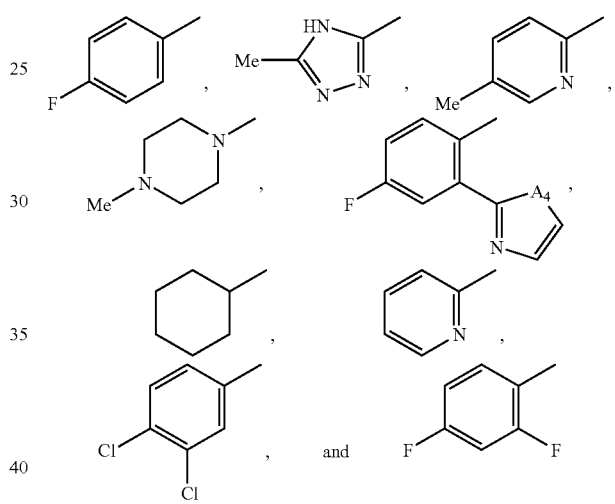

Wherein A$^4$ represents —O—, —S—, or —NH—;

R$^2$ represents a straight or branched alkyl group having 1 to 3 carbon atoms;

n is 0, 1, or 2;

Or an addition salt thereof with a pharmaceutically acceptable acid or base.

2. The compound according to claim 1 wherein Het is an optionally substituted group selected from the group consisting of furan; 1,3-thiazole; 1,3-oxazole; 1,3,4-oxadiazole; pyridine; pyrimidine; and 5,6-dihydropyran; or an addition salt thereof with a pharmaceutically acceptable acid or base.

3. The compound according to claim 1 wherein Het is substituted with a carboxyl group; or a nitrogen atom of the nitrogen atom-containing heterocyclic group of Het is N-oxide; or an addition salt thereof with a pharmaceutically acceptable acid or base.

4. The compound according to claim 1 wherein n is 0 or 1; or an addition salt thereof with a pharmaceutically acceptable acid or base.

5. The compound according to claim 1 wherein the group R$^1$-A$^3$ is a 4-fluorobenzyl group; or an addition salt thereof with a pharmaceutically acceptable acid or base.

6. A compound selected from the group consisting of:
5-(4-fluorobenzyl)-2-methanesulfonyl-6-(thiazol-2-yl)-5H-pyrrolo[2,3-b]pyrazine;
5-(4-fluorobenzyl)-2-methanesulfonyl-6-(oxazol-2-yl)-5H-pyrrolo[2,3-b]pyrazine; and an addition salt thereof with a pharmaceutically acceptable acid or base.

7. The compound according to claim 1 wherein $R^1$ is phenyl, pyridine, or cyclohexyl and Het is furan, thiazole, oxazole, oxadiazole, pyrimidine, pyran, or triazole.

8. A pharmaceutical composition containing as the active ingredient a compound according to claim 1 with a pharmaceutically acceptable ingredient.

9. A method for treating inflammation induced by cyclooxygenase-2 in a patient in need thereof comprising administering to said patient an effective amount of a compound according to claim 1.

* * * * *

UNITED STATES PATENT AND TRADEMARK OFFICE
CERTIFICATE OF CORRECTION

| | | |
|---|---|---|
| PATENT NO. | : 7,612,070 B2 | Page 1 of 1 |
| APPLICATION NO. | : 11/058597 | |
| DATED | : November 3, 2009 | |
| INVENTOR(S) | : Matsuoka et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1114 days.

Signed and Sealed this

Nineteenth Day of October, 2010

David J. Kappos
*Director of the United States Patent and Trademark Office*